(12) United States Patent
Bowman et al.

(10) Patent No.: US 9,932,590 B2
(45) Date of Patent: Apr. 3, 2018

(54) CONTROL OF VARROA MITE INFESTATION

(71) Applicants: THE UNIVERSITY COURT OF THE UNIVERSITY OF ABERDEEN, Aberdeen, Aberdeenshire (GB); THE SECRETARY OF STATE FOR ENVIRONMENT, FOOD AND RURAL AFFAIRS, York, Yorkshire (GB)

(72) Inventors: Alan Stuart Bowman, Aberdeen (GB); Ewan McInnes Campbell, Aberdeen (GB); Giles Elliott Budge, York (GB)

(73) Assignees: The University Court of the University of Aberdeen, Aberdeen (GB); The Secretary of State for Enviroment Food and Rural Affairs, York (GB)

( * ) Notice: Subject to any disclaimer, the term of this patent is extended or adjusted under 35 U.S.C. 154(b) by 0 days.

(21) Appl. No.: 14/902,505

(22) PCT Filed: Jul. 2, 2014

(86) PCT No.: PCT/GB2014/052004
§ 371 (c)(1),
(2) Date: Dec. 31, 2015

(87) PCT Pub. No.: WO2015/001336
PCT Pub. Date: Jan. 8, 2015

(65) Prior Publication Data
US 2016/0355823 A1    Dec. 8, 2016

(30) Foreign Application Priority Data

Jul. 2, 2013 (GB) .................................. 1311840.1

(51) Int. Cl.
| | | |
|---|---|---|
| *C12N 15/113* | (2010.01) | |
| *A01N 57/10* | (2006.01) | |
| *A23K 20/153* | (2016.01) | |
| *A23K 50/90* | (2016.01) | |
| *A01N 57/16* | (2006.01) | |

(52) U.S. Cl.
CPC .......... *C12N 15/1137* (2013.01); *A01N 57/16* (2013.01); *A23K 20/153* (2016.05); *A23K 50/90* (2016.05); *C12N 15/113* (2013.01); *C12N 15/1136* (2013.01); *C12N 15/1138* (2013.01); *C12Y 104/03004* (2013.01); *C12Y 204/01016* (2013.01); *C12Y 207/0104* (2013.01); *C12Y 301/01007* (2013.01); *C12Y 306/03014* (2013.01); *C12N 2310/11* (2013.01); *C12N 2310/14* (2013.01); *C12N 2310/51* (2013.01); *C12N 2320/30* (2013.01); *C12N 2320/31* (2013.01); *C12Y 205/01018* (2013.01); *C12Y 306/01003* (2013.01)

(58) Field of Classification Search
None
See application file for complete search history.

(56) References Cited

U.S. PATENT DOCUMENTS

2012/0258646 A1* 10/2012 Sela .................... A61K 31/713
449/2

FOREIGN PATENT DOCUMENTS

| WO | 2011/045796 | 4/2011 |
|---|---|---|
| WO | 2011/057825 | 5/2011 |

OTHER PUBLICATIONS

Campbell et al. Parasites & Vectors 2010, 3:73 (11 pages).*
Floris, I. et al., "Effectiveness, persistence, and residue of amitraz plastic strips in the spiary control of Varroa destructor," (2001) Apidologie 32(6):577-585.
Garbian, Y. et al., "Bidirectional transfer of RNAi between Honey Bee and Varroa destructor: Varroa gene silencing reduces Varroa population," (2012) Pathogens 8(12):1-9.
International Search Report and Written Opinion for International Patent Application No. PCT/GB2014/052004 dated Jan. 15, 2015 (14 pages).

* cited by examiner

*Primary Examiner* — Tracy Vivlemore
(74) *Attorney, Agent, or Firm* — Andrus Intellectual Property Law, LLP

(57) ABSTRACT

Nucleic acid agents for reducing or removing infestations of the *Varroa destructor* mite are described. Compositions comprising the nucleic acid agents and methods for controlling mite infestations using the nucleic acid agents and compositions are also disclosed.

24 Claims, 16 Drawing Sheets

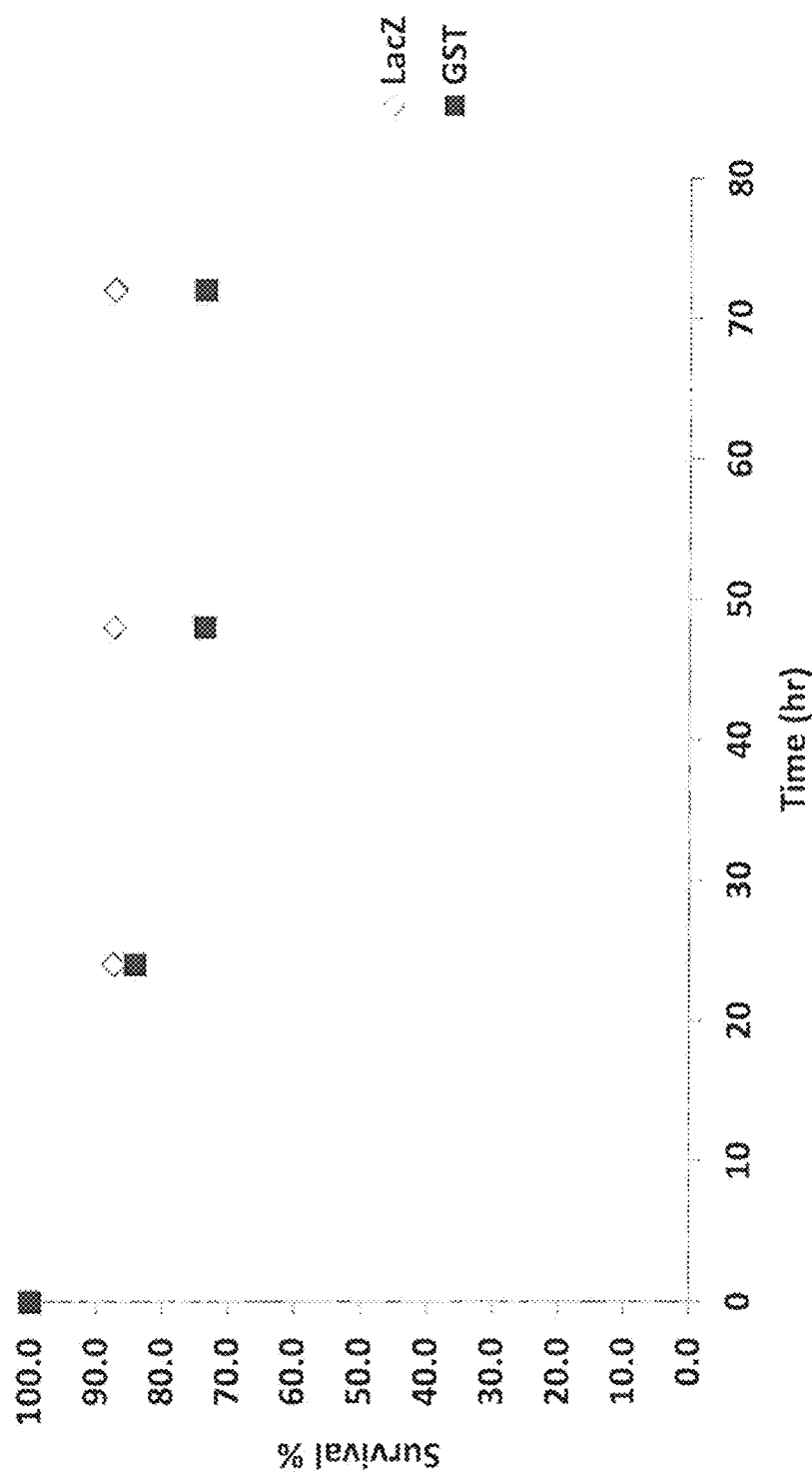
Figure 1. V.destructor mite survival following GST-μ1 knockdown via dsRNA soaking (LacZ control).

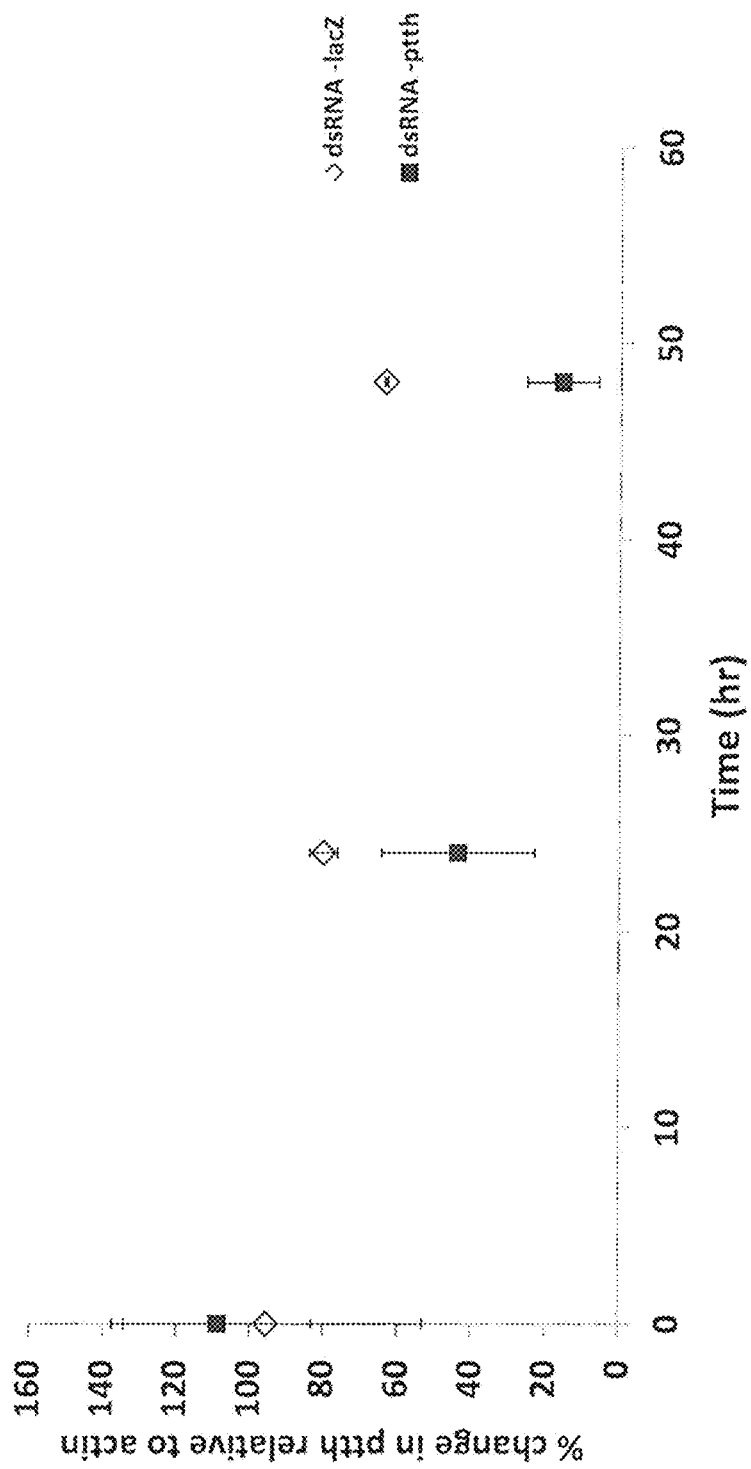
Figure 2. Knockdown of PTTH expression via dsRNA soaking (LacZ control).

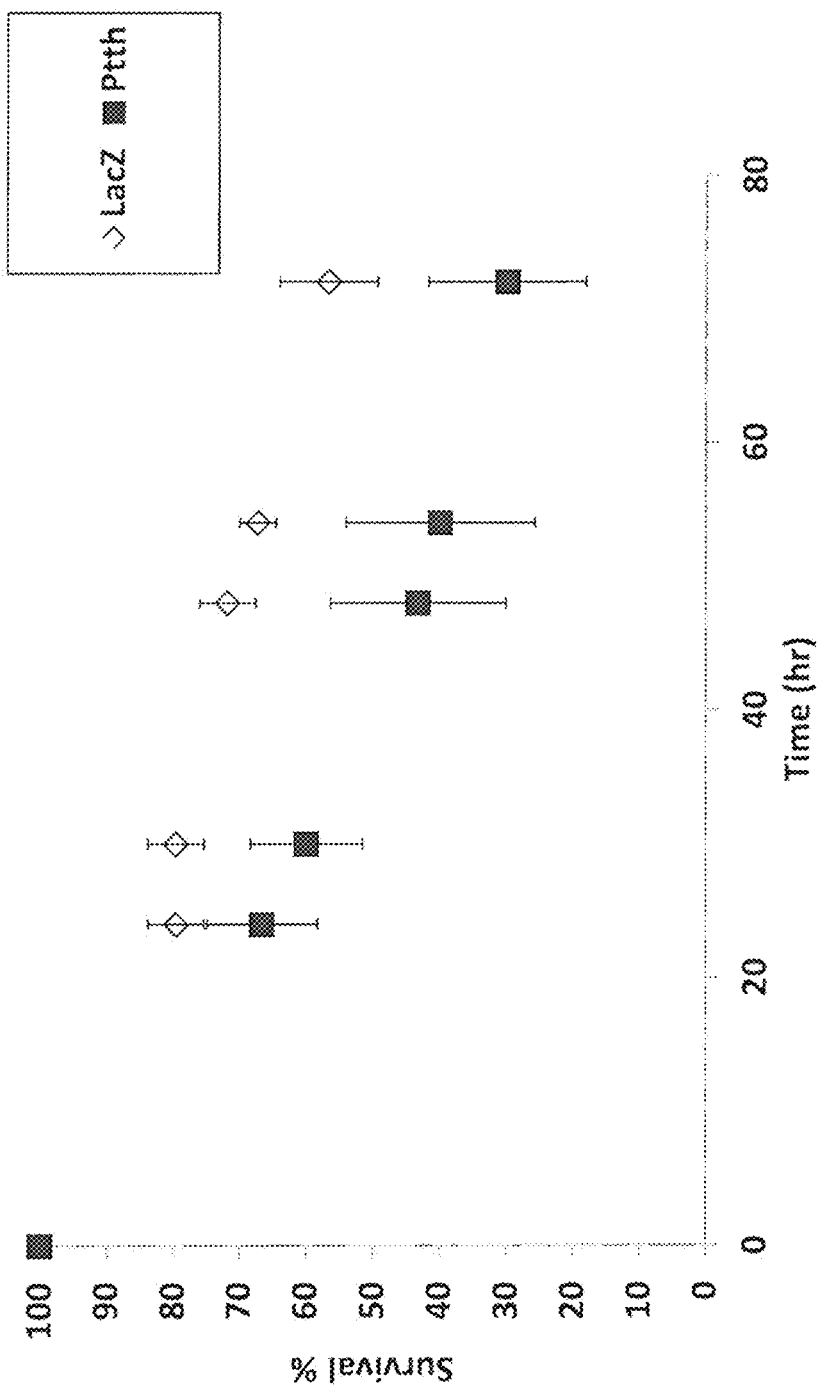
Figure 3. V. destructor mite survival following PTTH knockdown via dsRNA soaking (LacZ control).

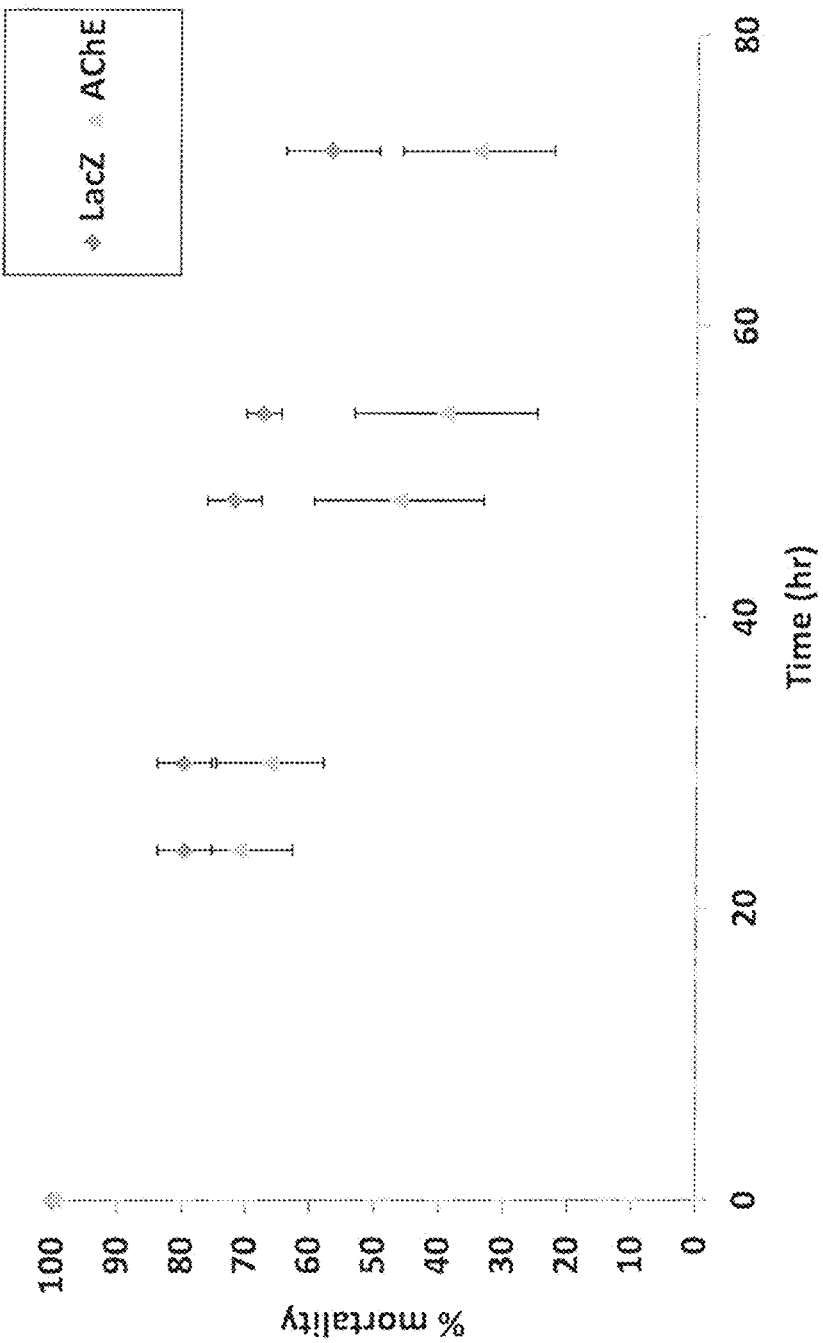
Figure 4. *V. destructor* mite survival following AChE knockdown via dsRNA soaking (LacZ control

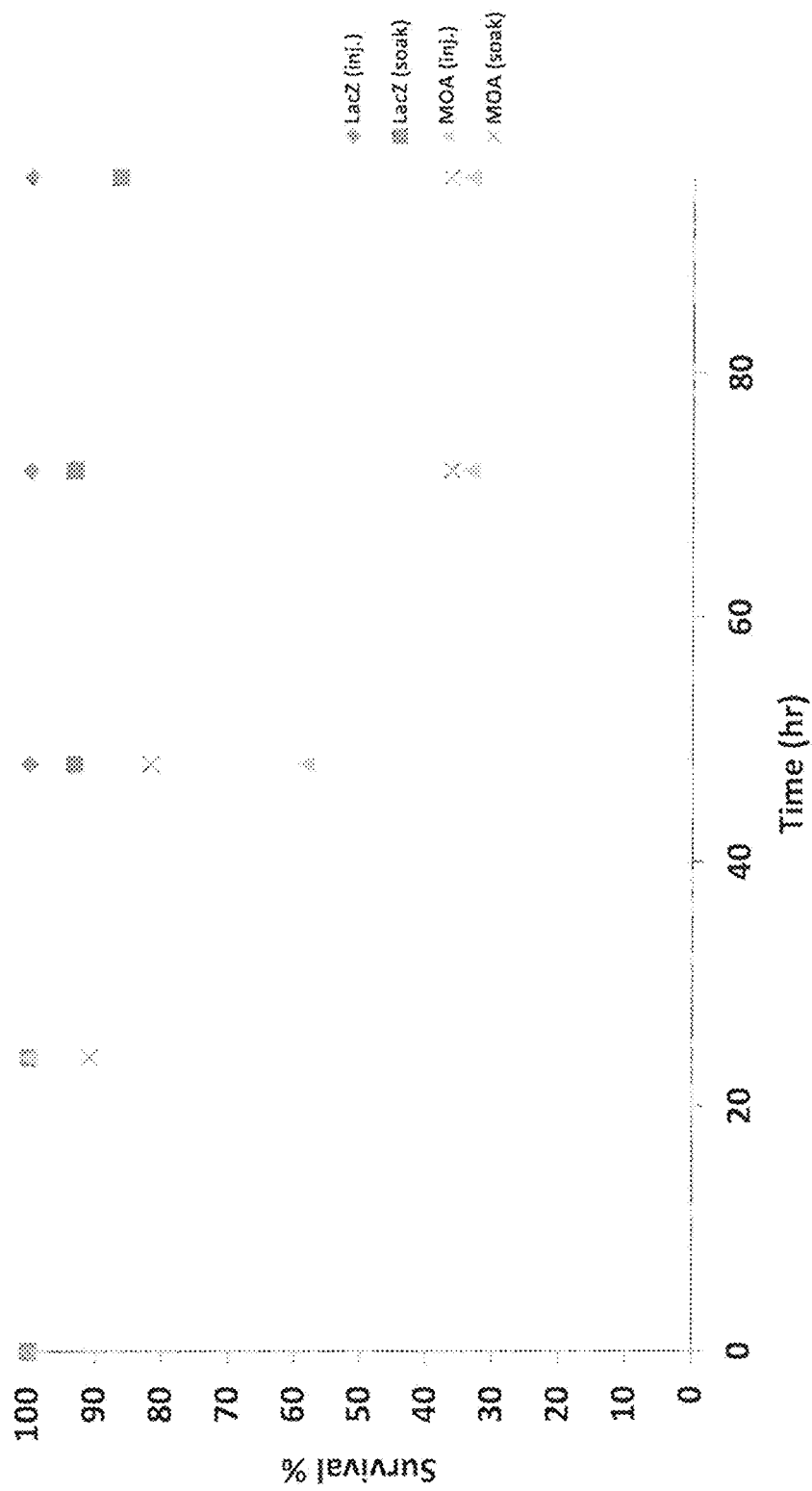
Figure 5. *V. destructor* mite survival following MOA knockdown (LacZ control).

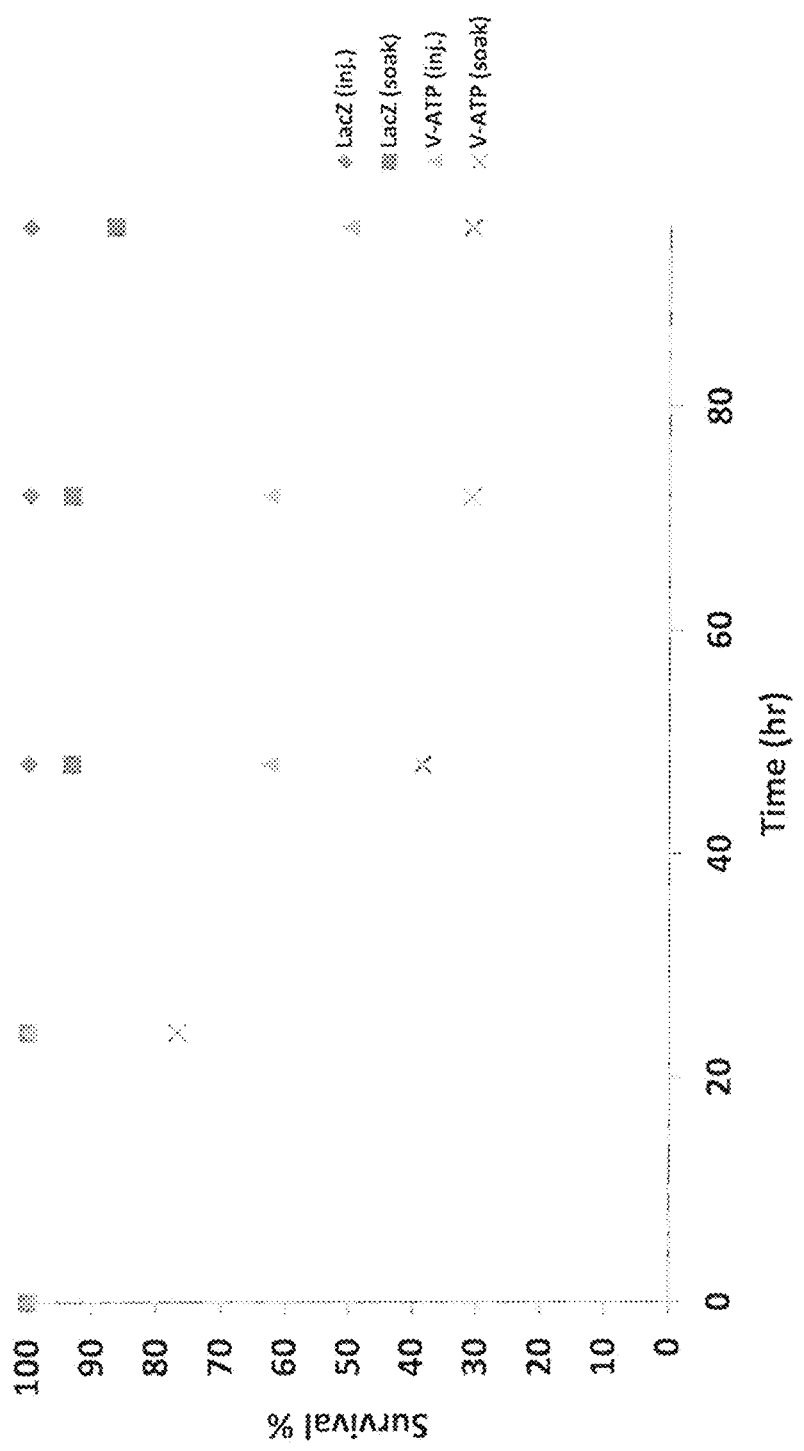
Figure 6. *V. destructor* mite survival following vATPase knockdown (LacZ control).

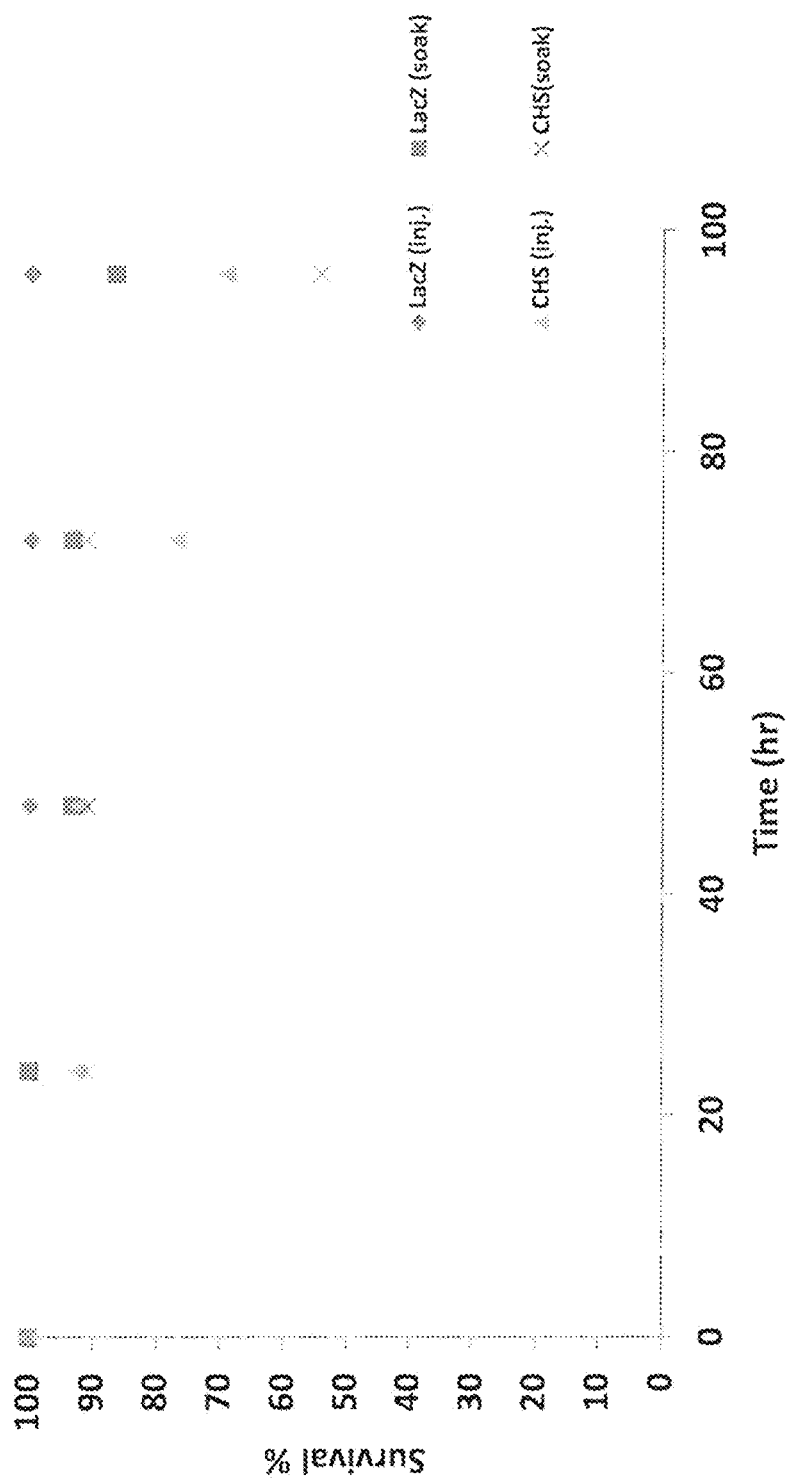
Figure 7. *V. destructor* mite survival following CHS knockdown (LacZ control).

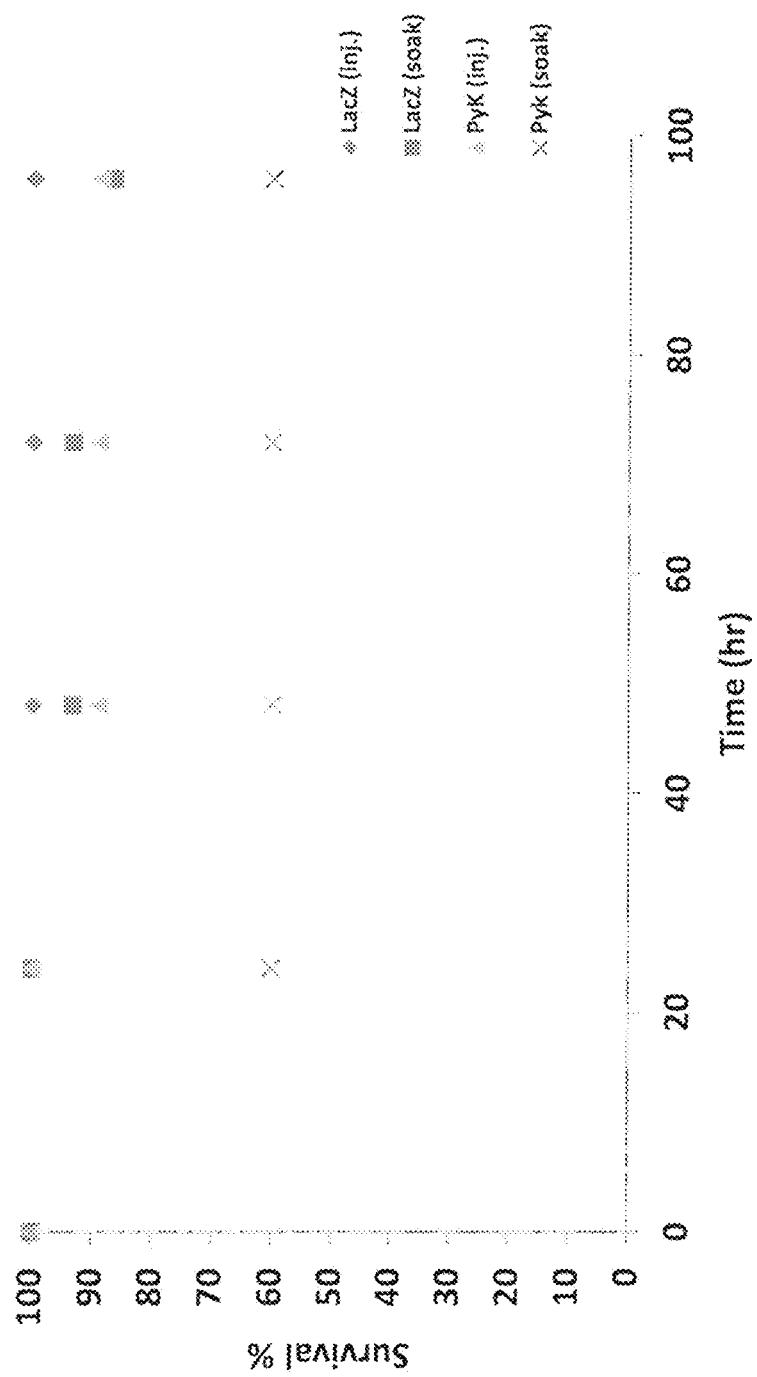
Figure 8. *V. destructor* mite survival following PyK knockdown (LacZ control).

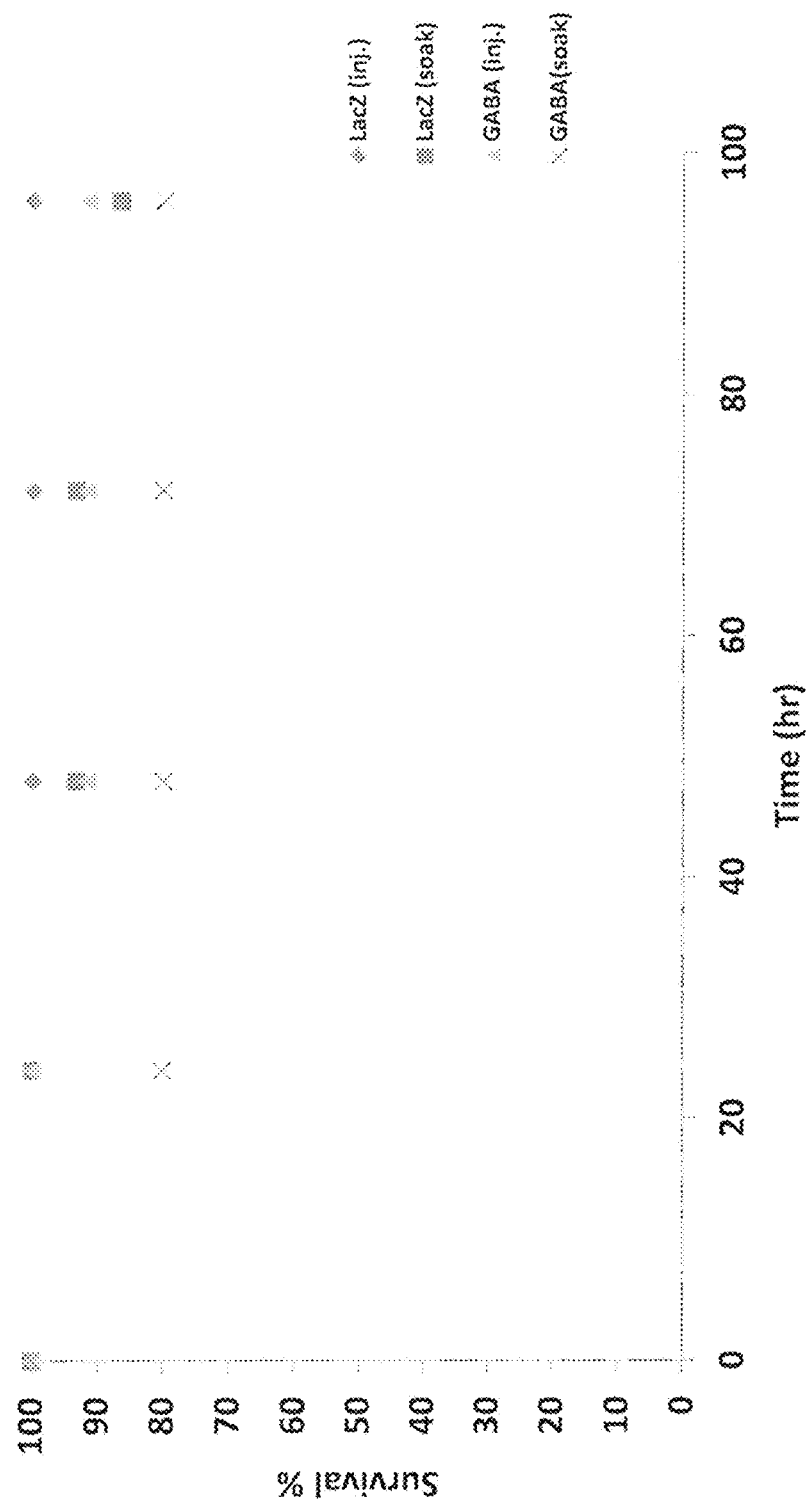
Figure 9. *V. destructor* mite survival following GABA knockdown (LacZ control).

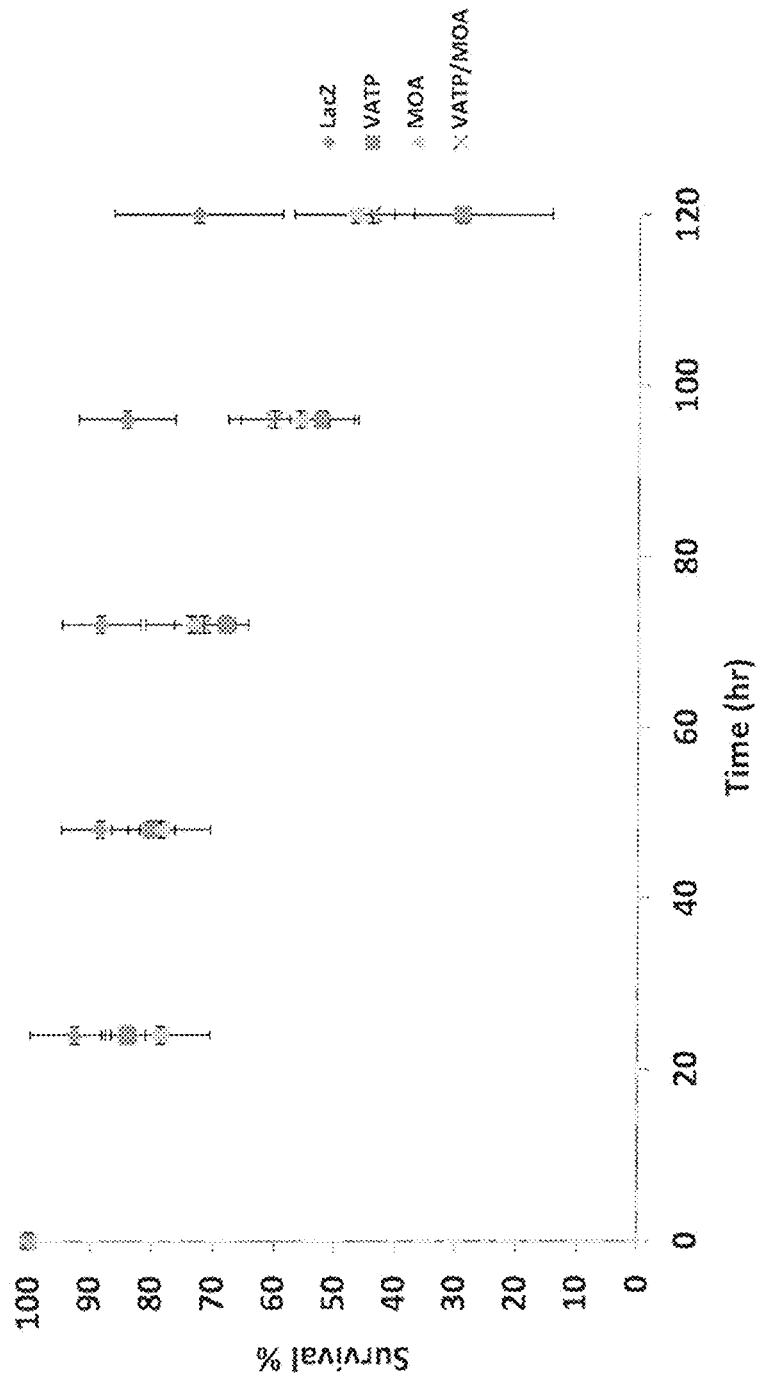
Figure 10A. *V. destructor* mite survival following knockdown of vATPase and/or MOA (LacZ control). All challenges had a final concentration of 1.25ug/μl dsRNA.

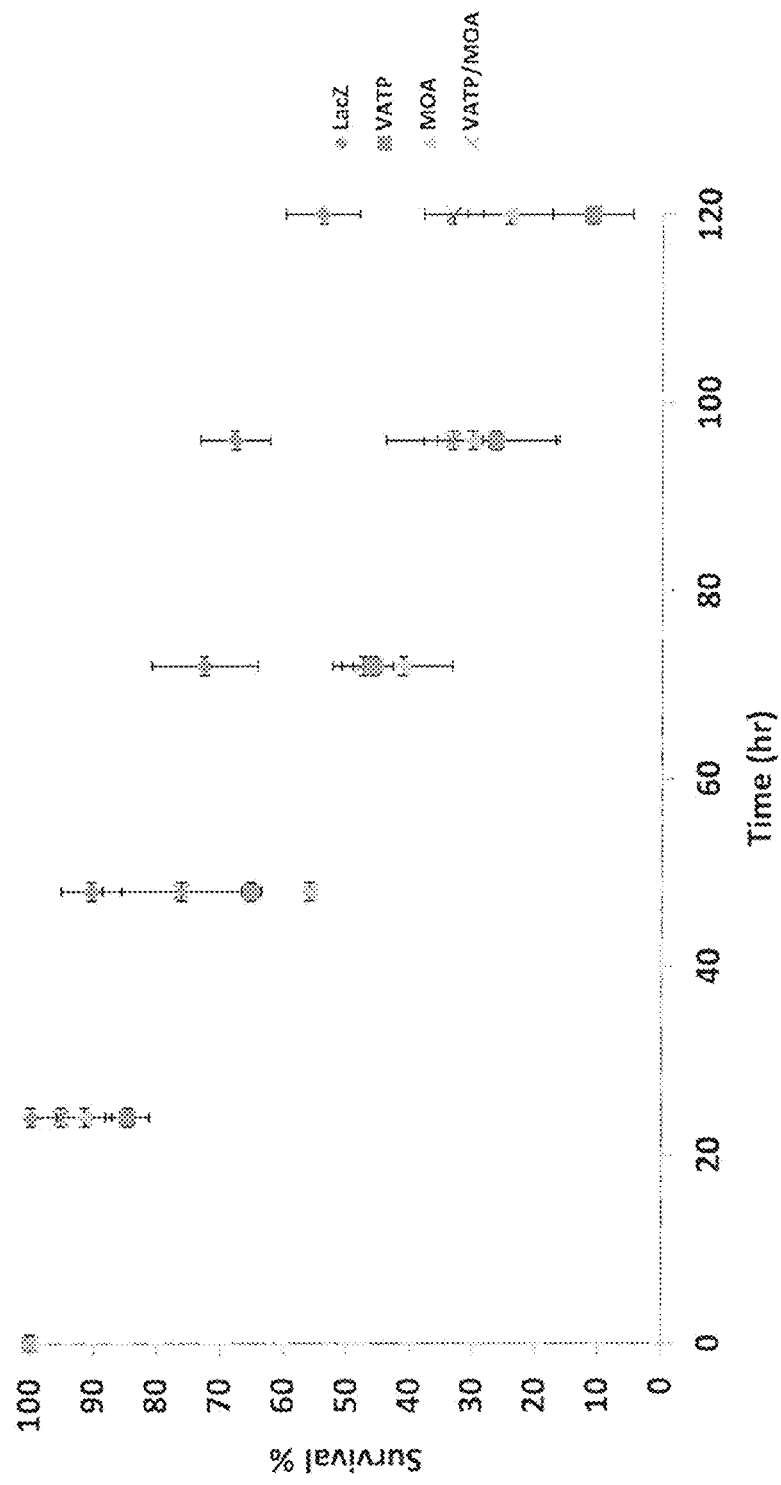
Figure 10B. *V. destructor* mite survival following knockdown of vATPase and/or MOA (LacZ control). All challenges had a final concentration of 1.25ug/μl dsRNA (repeat of 10A).

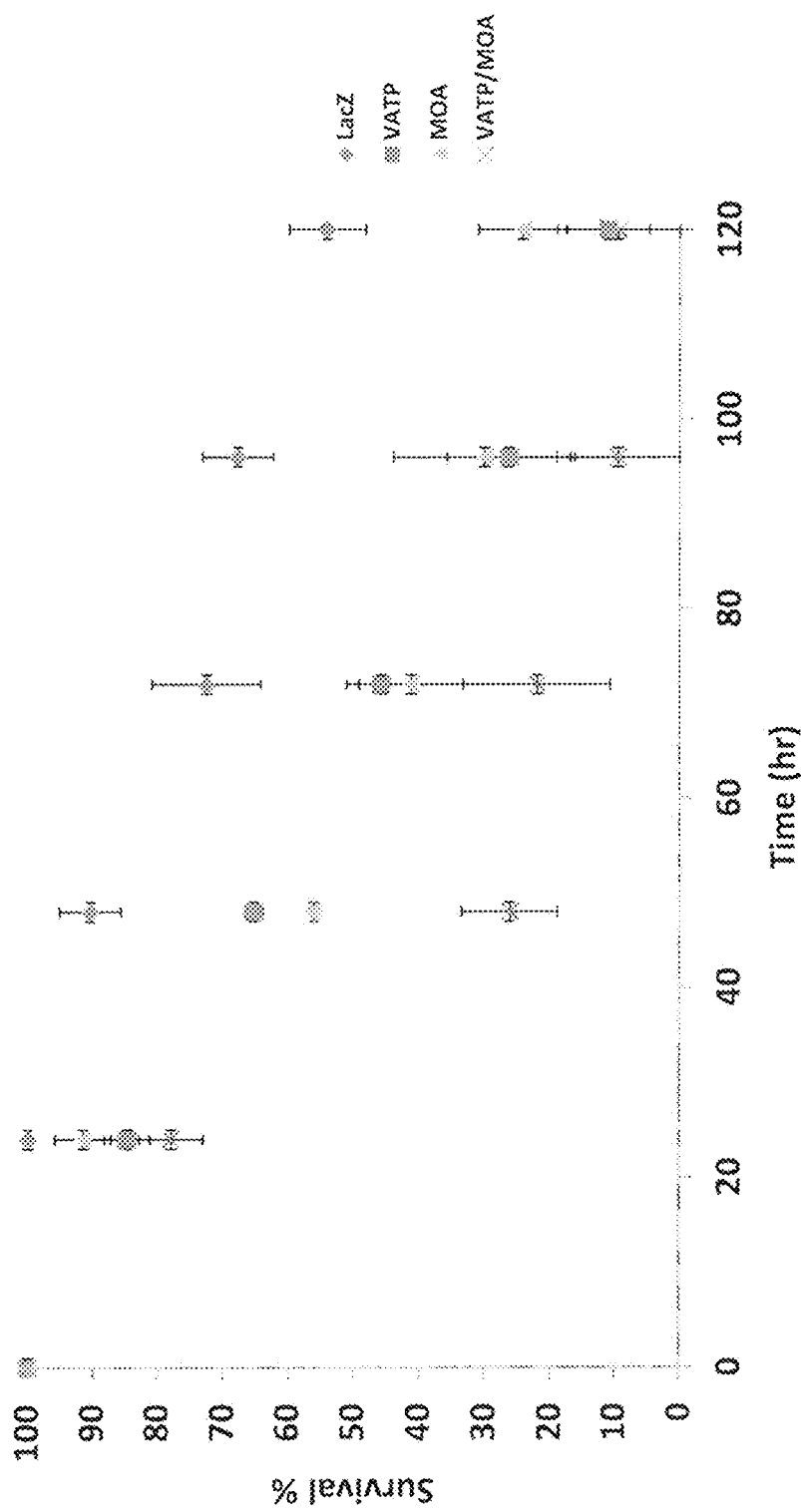
Figure 11. *V. destructor* mite survival following knockdown of vATPase and/or MOA (LacZ control). Each dsRNA had a final concentration of 1

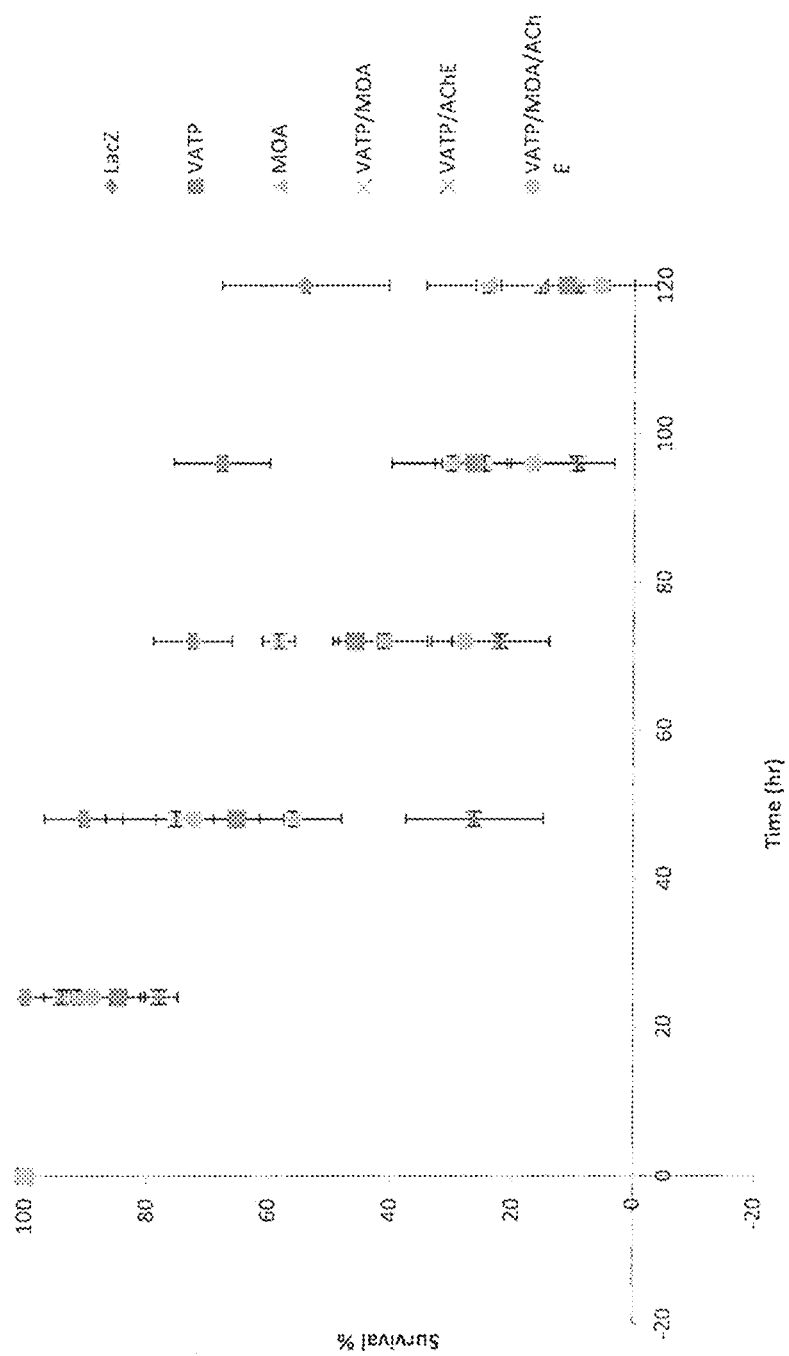
Figure 12. *V. destructor* mite survival following knockdown of vATPase and/or MOA and/or AChE (LacZ control). Each dsRNA had a final concentration of 1.25ug/μl dsRNA.

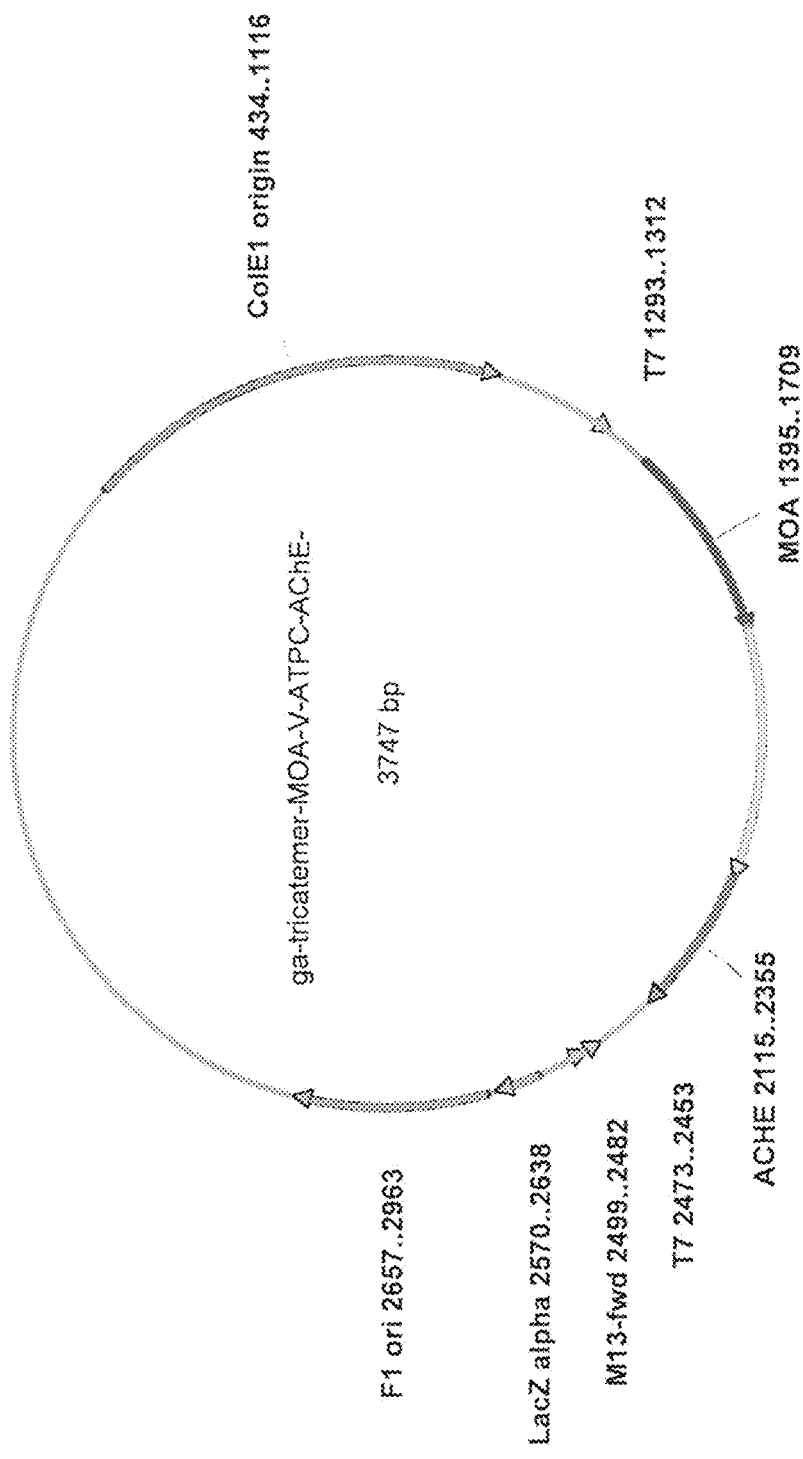
Figure 13. L4440-MOA-V-ATPC-ACHE-Tricatemer plasmid map: MOA, V-ATP-C, and AChE targets are indicated

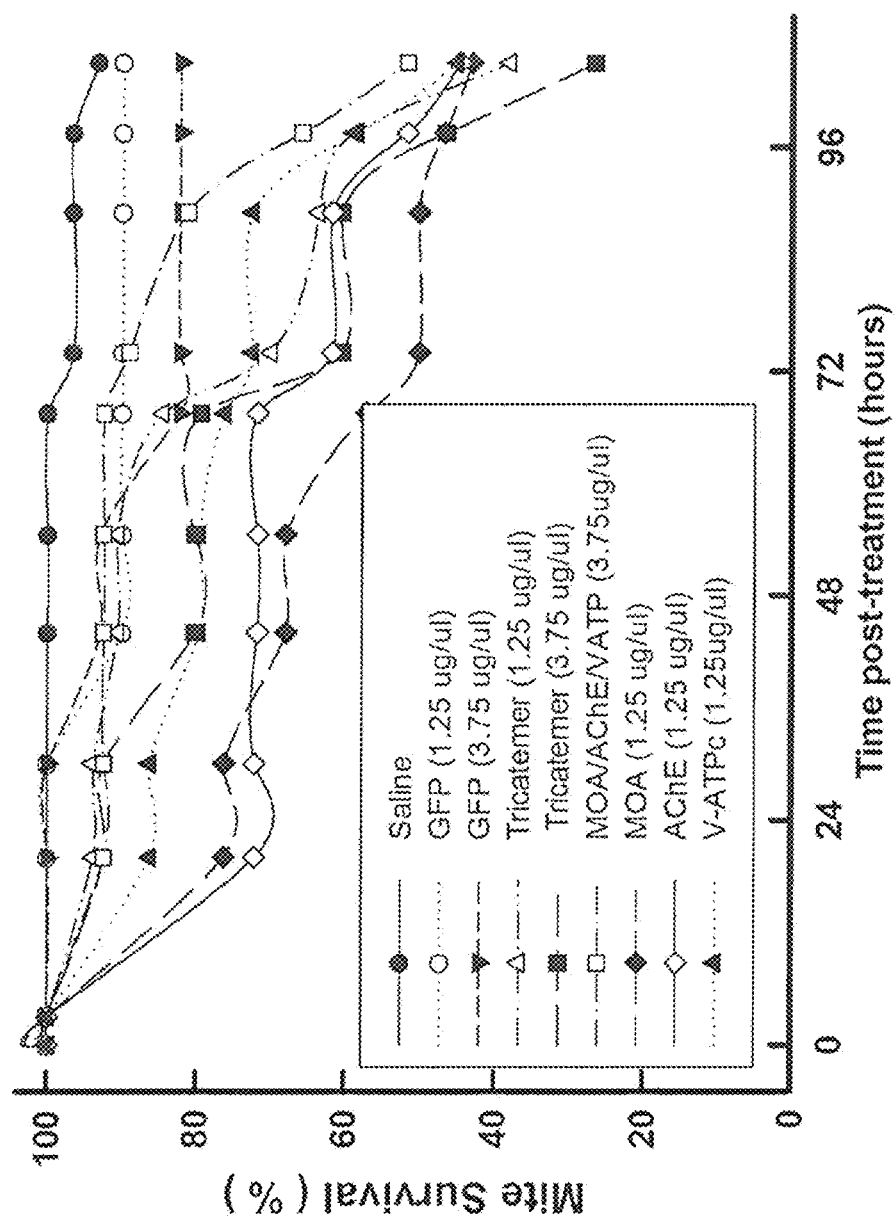
Figure 14. Effect of different dsRNA treatment on Varroa mite mortality.

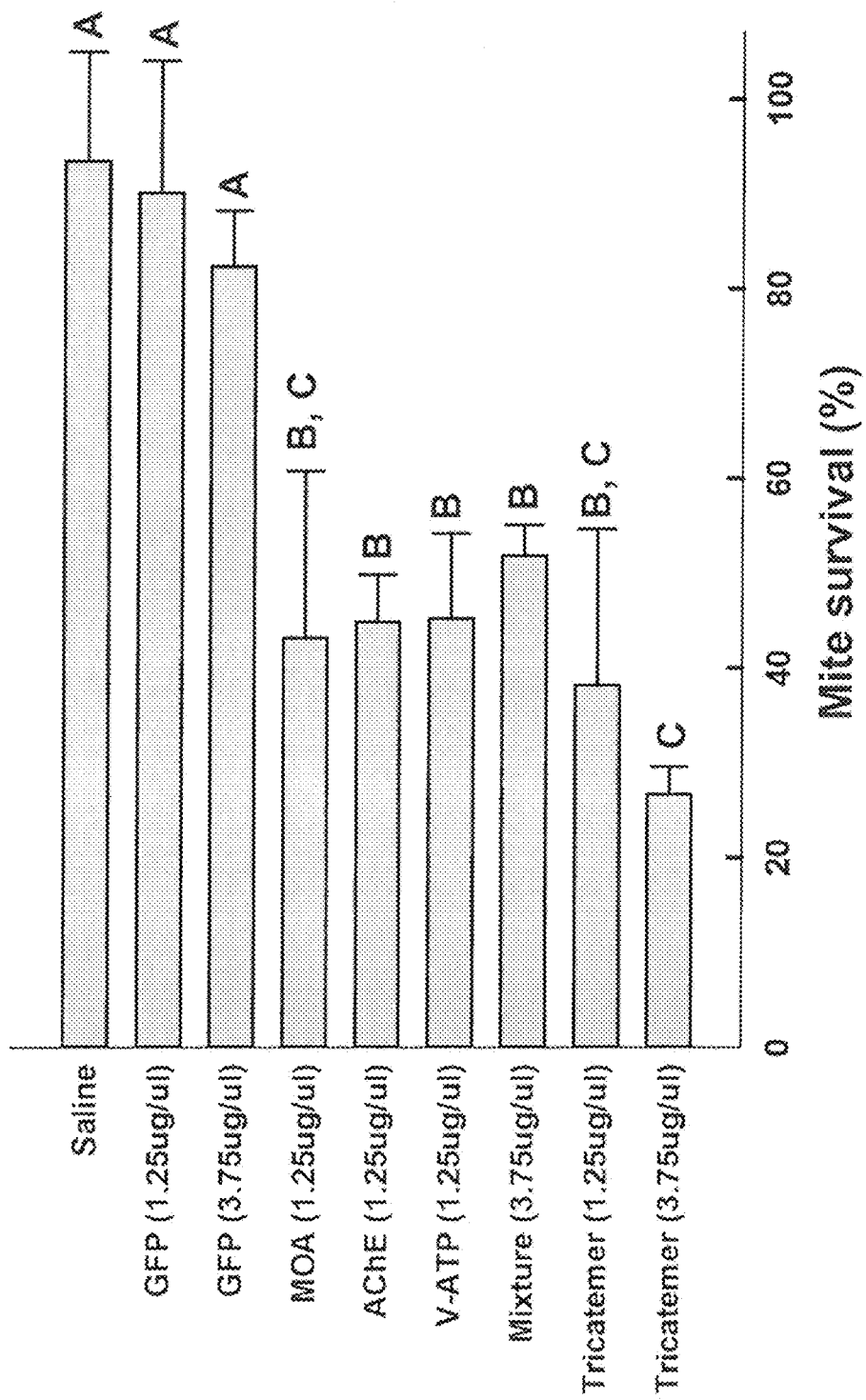
Figure 15. Effect of different dsRNA treatment on Varroa mite mortality.

US 9,932,590 B2

CONTROL OF VARROA MITE INFESTATION

CROSS-REFERENCE TO RELATED APPLICATIONS

This patent application is a national stage filing under 35 U.S.C. 371 of International Application No. PCT/GB2014/052004, filed Jul. 2, 2014, which claims the benefit of priority of Great Britain Application No. GB1311840.1, filed Jul. 2, 2013, both of which are incorporated herein by reference in their entireties.

TECHNICAL FIELD

The present invention relates to nucleic acid agents for reducing or removing infestations of the *Varroa destructor* mite. Compositions comprising the nucleic acid agents and methods for controlling mite infestations using the nucleic acid agents and compositions are also disclosed.

BACKGROUND

The European honey bee, *Apis mellifera*, is vital to the pollination of agricultural and wild plants [1]. There is widespread concern about the worldwide decline in the abundance of *A.meffifera* [2]. The ectoparasitic *Varroa* mite (*Varroa destructor*) is the most important pest of *A.meffifera* and plays a central role to honey bee losses [3].

*V.destructor* originally parasitized the Asian bee (*A.cerana*) where it nearly exclusively parasitized the male bees (drones), thus making little impact on the bee colony the European honey bee (*A.meffifera*) upon which it parasitizes both the drones and female bees (workers). This shift in parasitized caste is significant because the workers make up the bulk of the adult bee population within a colony [4].

*V.destructor* entered mainland Europe in the 1970's, the USA in 1987 and the UK in 1992 and subsequently has been associated with the loss of millions of colonies [3]. The mite causes damage by feeding on the haemolymph of both the developing bee within brood cells and the adult bee, thus weakening the immune systems of their hosts. Moreover, wound sites caused by mite feeding harbour bacterial infections, such as *Melissococcus pluton*, and mites transmit viral pathogens such as deformed wing virus (DWV), Kashmir bee virus (KBV), acute bee paralysis virus (ABPV), and black queen cell virus (BQCV).

In terms of both the number of enterprises affected and the impact of global food production, varroosis is arguably the most serious disease of livestock in any species. Previous control of *V.destructor* by chemical treatment is increasingly ineffective due to the development of widespread resistance in mites to the limited available acaricides [5]. Thus, there is an urgent need to harness modern molecular techniques for research into the biology and, ultimately, the control of this non-model organism, *V.destructor*.

RNA interference (RNAi) is a gene silencing technique that is becoming an ever more powerful tool in investigating the functional role of specific genes that may be potential targets for chemotherapeutic intervention. The RNAi mechanism involves the in vivo production of small interfering RNA molecules (siRNAs) from larger introduced double-stranded RNA (dsRNA). siRNA molecules target and destroy specific mRNA, silencing the target gene at the post-transcriptional stage.

Whyard et al. 2009 discuss the use of RNAi based gene suppression as a species-specific insecticide [6], with other studies showing that *V.destructor* is susceptible to the suppression of gene expression via the administration of dsRNA [7]. The dsRNA can be effectively delivered to *V.destructor* both directly, for example by via intrahaemocoelic injection or immersion/spraying in solutions containing dsRNA [7], or indirectly, for example by feeding dsRNA to *A.meffifera* hosts which are subsequently parasitized by the *V.destructor* mites [8], [9].

This transfer of dsRNA from *A.meffifera* hosts to *V.destructor* mites has been reported to lead to a decrease in mite population in tested mini-hives [9]. The authors report a maximum reduction in *V.destructor* mite numbers of 61%, as recorded at the end of a 60-day trial period during which mites were exposed to a dsRNA mix containing 14 *V.destructor* sequences. The 60-day trial period allowed for two reproductive cycles of *V.destructor*, and the authors of [9] did not directly measure *V.destructor* mite mortality; thus, the 61% figure represents the combined effects of mortality and reduced fecundity over two generations of *V.destructor* mite.

DISCLOSURE

The present inventors herein identified target genes whose reduced expression leads to significantly increased mortality of *V.destructor* mites. The inventors further provide nucleic acid constructs suitable for reducing the expression of the identified genes.

The identified group of target *V.destructor* genes contain genes that are either critical housekeeping genes, targets for an existing pesticide, neural peptides/hormones (a critical group in arthropods), or complementary in activity to one of the previous target classes. The identified target genes include, Acetylcholinesterase (AChE), Monoamine Oxidase (MOA), v-ATPase subunit C (vATPc), the GABA receptor (GABA), Chitin Synthase (CHS), Pyruvate Kinase (PyK), α-Tubulin (αTUB), pro-thoracicotropic hormone (PTTH), crustacean hyperglycemic hormone (CHH), and glutathione S-transferase mu-1 (GSTµ1). Reducing the expression of each of these genes in isolation results in an increase in *V.destructor* mortality of up to 70%.

Accordingly, in one aspect the present invention provides a nucleic acid agent comprising a nucleic acid sequence that is capable of downregulating the expression of a gene of the *Varroa destructor* mite, wherein the gene encodes Acetylcholinesterase (AChE; GenBank accession number ADDG01069748.1) (SEQ ID NO: 16), Monoamine Oxidase (MOA; GenBank accession number ADDG01053234.1), (SEQ ID NO: 15) vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PITH; GenBank accession number ADDG01000788.1) (SEQ ID NO: 22), Crustacean hyperglycaemic hormone (CHH; GenBank accession number ADDG01078386.1) (SEQ ID NO: 23) or Glutathione transferase mu1 (GSTµ1; GenBank accession number ADDG01001667.1) (SEQ ID NO: 24).

In preferred embodiments the gene encodes Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), or vATPase subunit C (vATPc; GenBank accession number ADDG01035752.1 (SEQ ID NO: 17). In even more preferred embodiments, the gene encodes Monoamine Oxidase (MOA; GenBank accession number ADDG01053234.1) (SEQ ID NO: 15).

There are several different mechanisms through which downregulation of gene expression occurs.

Gene expression can be downregulated by the repression of mRNA translation. In this mechanism, small (~22 nucleotide), non-coding, non-perfectly complementary RNA molecules (often called micro RNAs, or miRNAs) to mRNA molecules. The binding of this type of miRNA inhibits the translation of the mRNA, so reducing the expressed level of the encoded protein gene product. miRNAs inducing translational repression are imperfectly complementary to their target mRNAs; that is, the miRNAs have sufficiently high sequence identity to their target mRNAs that they can specifically bind to them, but have regions in which there are mismatches in base pairing. There is often a pattern to regions of match and mismatch, with perfect or good base pairing typically seen for nucleotides 2 to 8 and 13-16 of a ~22 nucleotide miRNA, with mismatches seen in the central and 3' sections.

Accordingly, in one aspect the nucleic acid agent according to the present invention comprises a nucleic acid sequence that has at least 50% sequence identity to at least 18 contiguous nucleotides of an mRNA encoded by the gene of the *Varroa destructor* mite, and wherein the nucleic acid agent inhibits translation of the mRNA. In some embodiments the nucleic acid sequence has at least 50% sequence identity to at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10 (preferably SEQ ID NO.1, SEQ ID NO.2, or SEQ ID NO.3; most preferably SEQ ID NO.2). In some embodiments the nucleic acid sequence has at least 50%, 60%, 70%, 80%, 90% or at least 95% sequence identity to at least 18, 19, 20, 21, 22, 23, 24, 25, 26, 27, 28, 29 or at least 30 contiguous nucleotides. In preferred embodiments the nucleic acid sequence has at least 50% sequence identity to at least 22 contiguous nucleotides. In some embodiments the nucleic acid sequence contains at least 5, at least 6, or at least 7 contiguous nucleotides having 100% sequence identity to the mRNA.

In one embodiment the nucleic acid agent according to the present invention comprises a nucleic acid sequence that has at least 50% sequence identity to at least 22 contiguous nucleotides of an mRNA encoded by the gene of the *Varroa destructor* mite, wherein the nucleic acid inhibits translation of the mRNA and wherein the nucleic acid sequence contains at least 7 contiguous nucleotides having 100% sequence identity to the mRNA. In another embodiment the nucleic acid agent according to the present invention comprises a nucleic acid sequence that has at least 50% sequence identity to at least 22 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10 (preferably SEQ ID NO.1, SEQ ID NO.2, or SEQ ID NO.3; most preferably SEQ ID NO.2), wherein the nucleic acid agent inhibits translation of the mRNA and wherein the nucleic acid sequence contains at least 7 contiguous nucleotides having 100% sequence identity to the mRNA.

Gene expression can also be downregulated by the targeted degradation of mRNA. Targeted degradation of mRNA can be achieved by a ribozyme molecule capable of specifically cleaving an mRNA encoded by the gene of the *Varroa destructor* mite. Thus, in one aspect the nucleic acid agent according to the present invention is a ribozyme.

Targeted degradation of mRNA can be achieved through post-translational gene silencing (PTGS), also known as RNA interference (RNAi).

RNA Interference

RNAi is an RNA-dependent gene silencing process that is controlled by the RNA-induced silencing complex (RISC) and is initiated by short double-stranded RNA molecules in a cell's cytoplasm, where they interact with the catalytic RISC component argonaute.

When the dsRNA is exogenous (for example, coming from infection by a virus with an RNA genome), the RNA is imported directly into the cytoplasm and cleaved to short fragments by the argonaute enzyme.

The initiating dsRNA can also be endogenous (originating in the cell), as in pre-microRNAs expressed from RNA-coding genes in the genome. The primary transcripts from such genes are first processed to form the characteristic stem-loop structure of pre-miRNA in the nucleus, then exported to the cytoplasm to be cleaved by Dicer. Thus, the two dsRNA pathways, exogenous and endogenous, converge at the RISC complex.

dsRNA initiates RNAi by activating the ribonuclease protein Dicer, which binds and cleaves double-stranded RNAs (dsRNAs) to produce double-stranded fragments of 20-25 base pairs with a 2-nucleotide overhang at the 3' end. Bioinformatics studies on the genomes of multiple organisms suggest this length maximizes target-gene specificity and minimizes non-specific effects. These short double-stranded fragments are called small interfering RNAs (siRNAs). These siRNAs are then separated into two single-stranded (ss) ssRNAs, namely the passenger strand and the guide strand. The passenger strand is degraded, and the guide strand is incorporated into the RNA-induced silencing complex (RISC). After integration into the RISC, siRNAs base-pair to their target mRNA and induce cleavage of the mRNA, thereby preventing it from being used as a translation template. In some organisms, this process is known to spread systemically, despite the initially limited molar concentrations of siRNA.

A key feature required for the RNAi effect is a short stretch (~21 nucleotides) of duplex RNA having 100% sequence identity to the downregulated mRNA. Any nucleic acid which will be processed into, or lead to the generation of, an siRNA with this feature can lead to RNAi suppression of the target mRNA. Thus in addition to dsRNA (which is processed into siRNA by the activity of Dicer and the RISC complex), short hairpin RNAs (shRNAs) and some miRNAs may also initiate RNAi suppression.

Accordingly, in one aspect the nucleic acid agent according to the present invention comprises a nucleic acid sequence that has 100% sequence identity to at least 18 contiguous nucleotides of an mRNA encoded by the gene of the *Varroa destructor* mite, and wherein the nucleic acid agent induces the degradation of the mRNA. In some embodiments the nucleic acid sequence has 100% sequence identity to at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10 (preferably SEQ ID NO.1, SEQ ID NO.2, or SEQ ID NO.3; most preferably SEQ ID NO.2). In some embodiments the nucleic acid sequence has 100% sequence identity to at least 18, 19, 20, 21, 22, 23, 24, 25, 26, 27, 28, 29 or at least 30 contiguous nucleotides. In some embodiments the nucleic acid sequence has 100% sequence identity to at least 21 contiguous nucleotides. In some embodiments the nucleic acid sequence has 100% sequence identity to at least 25 contiguous nucleotides. In some embodiments the nucleic acid sequence has 100% sequence identity to at least 27 contiguous nucleotides. In some embodiments the nucleic acid sequence has 100% sequence identity to at least 30 contiguous nucleotides. In some embodiments the nucleic acid sequence has 100% sequence identity to at least 50 contiguous nucleotides. In some embodiments the nucleic acid sequence has 100% sequence identity to at least 100 contiguous nucleotides. In some embodiments the nucleic acid sequence has 100% sequence identity to at least 200 contiguous nucleotides. In some embodiments the nucleic acid sequence has 100% sequence identity to at least 30, 40, 50, 60, 70, 80, 90, 100, 150, 200, 250, 300, 350, 400, 450, 500, 550, 600, 650, 700, 750 or 800 contiguous nucleotides In some embodiments of the nucleic acid agent according to the present invention comprises, consists essentially of, or consists of a nucleic acid sequence that has 100% sequence identity to the full-length encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10 (preferably SEQ ID NO.1, SEQ ID NO.2, or SEQ ID NO.3; most preferably SEQ ID NO.2).

Simultaneous Gene Repression
Parallel Gene Repression

As noted above, reducing the expression of each of the identified genes in isolation results in an increase in *V.destructor* mortality of up to 70%. However, the present inventors observed that even higher levels of *V.destructor* mortality were observed when two or more of the genes are targeted simultaneously.

Simultaneous gene targeting can be achieved through using a nucleic acid composition which is a mixture of at least two nucleic acid agents as described herein. An example of such a mixture is a nucleic acid composition which comprises a mixture of: (i) a nucleic acid agent capable of down-regulating the expression of AChE (such as at least 21 base pairs of SEQ ID NO:1), (ii) a nucleic acid agent capable of down-regulating the expression of MOA (such as at least 21 base pairs of SEQ ID NO:2), and (iii) a nucleic acid agent capable of down-regulating the expression of vATPc (such as at least 21 base pairs of SEQ ID NO:3).

Thus, in one aspect the present invention provides a nucleic acid composition comprising at least two nucleic acid agents according to the present invention. In some embodiments the nucleic acid composition comprises 2, 3, 4, 5, 6, 7, 8, 9, 10, 15, 20, 25, 30, 35, 40, 45, 50 or more than 50 nucleic acids according to the present invention.

The at least two nucleic acid agents may be capable of downregulating the expression of the same gene. However, preferably the at least two nucleic acid agents are capable of downregulating the expression of two different genes from *Varroa destructor*. Similarly, nucleic acid compositions comprising 2, 3, 4, 5, 6, 7, 8, 9, 10, 15, 20, 25, 30, 35, 40, 45, 50 or more than 50 nucleic acid agents according to the present invention are preferable capable of downregulating the expression of 2, 3, 4, 5, 6, 7, 8, 9, 10, 15, 20, 25, 30, 35, 40, 45, 50 or more than 50 different genes from *Varroa destructor.*

Thus, in one embodiment the present invention provides a nucleic acid composition comprising two nucleic acid agents according to the present invention, wherein the two nucleic acid agents are capable of downregulating the expression of two of the genes from *Varroa destructor*. In another embodiment the present invention provides a nucleic acid composition comprising three nucleic acids agents according to the present invention, wherein the three nucleic acid agents are capable of downregulating the expression of three of the genes from *Varroa destructor.*

In one embodiment, the nucleic acid composition comprises nucleic acid agents that are capable of down-regulating the expression of AChE and vATPc, for example at least 21 base pairs of the nucleic acid agents encoded by SEQ ID NO:1 and SEQ ID NO:3. In another embodiment the nucleic acid composition comprises nucleic acid agents that are capable of down-regulating the expression of MOA and vATPc, for example at least 21 base pairs of the nucleic acid agents encoded by SEQ ID NO:2 and SEQ ID NO:3. In another embodiment the nucleic acid composition comprises nucleic acid agents that are capable of down-regulating the expression of AChE, MOA and vATPc, for example at least 21 base pairs of the nucleic acid agents encoded by SEQ ID NO:1, SEQ ID NO:2 and SEQ ID NO:3.

Concatemer Gene Repression

The present inventors have found that concatenating separate nucleic acid agents into a isolated nucleic acid concatemer unexpectedly increases the effectiveness of the agents in killing *Varroa* mites relative to an equivalent amount of the separate agents delivered simultaneously as a mixture (see Example 5, and FIGS. 13, 14 & 15). Without wishing to be limited by theory, it is believed this increased mortality is because the concatemer reliably targets multiple genes within an individual cell, as opposed to targeting different genes in several cells. This is theorised to increase the likelihood that a targeted cell dies, or is no longer able to function, as opposed to being merely functionally impaired.

The term "isolated nucleic acid concatemer" is used herein to refer to a two or more nucleic acid sequences capable of down-regulating gene expression which have been joined ('concatenated') such that they form a single, contiguous nucleic acid molecule. In this sense the term "isolated nucleic acid concatemer" is intended to refer to concatenates not naturally occurring in nature. Preferably each of the constituent nucleic acid sequences of an "isolated nucleic acid concatemer" targets a different gene such that the concatemer is capable of down-regulating the expression of at least two different genes simultaneously.

Typically, the constituent nucleic acid sequences of an isolated nucleic acid concatemer are found sequentially on the nucleic acid molecule with only short, or no, intervening sequence ('spacer sequence') between the sequences capable of down-regulating gene expression. In some embodiments there is no more than 500 base pairs of spacer sequence between each sequence capable of down-regulating gene expression, such as no more than 400, 300, 200, 100, 50, 20, 10 or 5 base pairs of spacer sequence.

An example of an "isolated nucleic acid concatemer" is shown in FIG. 13. In this Figure, a isolated nucleic acid concatemer according to the present description extends from the first base of MOA (base 1395) to the last base of AChE (base 2355) to give a total concatemer length of 960 bases. The concatemer is composed of three nucleic acid sequences capable of down-regulating the expression (marked MOA, ATP, AChE) which are arranged sequentially on the nucleic acid molecule with no spacer sequences. This isolated nucleic acid concatemer is capable of down-regulating three genes (MOA, vATPc, AChE) simultaneously (see Table 5 in Example 5). Such a concatemer consisting of three nucleic acid sequences capable of down-regulating the expression genes of the *Varroa destructor* mite is herein called a "tricatemer".

Accordingly, in one aspect the present invention provides a nucleic acid concatemer comprising at least a first nucleic acid sequence and a second nucleic acid sequence;
wherein the first nucleic acid sequence is capable of down-regulating the expression of a first gene of the *Varroa destructor* mite, and the second nucleic acid sequence is capable of down-regulating the expression of a second gene of the *Varroa destructor* mite. Preferably the first and second genes are different genes.

In one aspect the present invention provides a nucleic acid concatemer comprising at least a first nucleic acid sequence, a second nucleic acid sequence, and a third nucleic acid sequence;
wherein the first nucleic acid sequence is capable of down-regulating the expression of a first gene of the *Varroa destructor* mite, the second nucleic acid sequence is capable of down-regulating the expression of a second gene of the *Varroa destructor* mite, and the third nucleic acid sequence is capable of down-regulating the expression of a third gene of the *Varroa destructor* mite. Preferably the first, second and third genes are different genes.

Concatemers comprising two, three, four, five, six, seven, eight, nine, ten, fifteen, twenty or more than twenty nucleic acid sequences are envisaged (preferably capable of, respectively, down-regulating the expression of two, three, four, five, six, seven, eight, nine, ten, fifteen, twenty or more than twenty different genes of the *Varroa destructor* mite.

In some embodiments the first and/or second gene (and/or third gene, if present) are selected from the group consisting of the genes which encode: Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PTTH; GenBank accession number ADDG01000788.1) (SEQ ID NO: 22), Crustacean hyperglycaemic hormone (CHH; GenBank accession number ADDG01078386.1) (SEQ ID NO: 23) or Glutathione transferase mu1 (GSTµ1; GenBank accession number ADDG01001667.1) (SEQ ID NO: 24). In some embodiments all of the first and second gene (and third gene, if present) are selected from the above group.

In some embodiments the first and/or second nucleic acid sequence (and/or third nucleic acid sequence, if present) comprises a nucleic acid sequence that has 100% sequence identity to at least 18 contiguous nucleotides (such as at least 21, 25, 30, 50, 100, 200, or 500 nucleotides) encoded by a sequence selected from the group consisting of SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10. In some embodiments all of the first and second nucleic acid sequence (and third nucleic acid sequence, if present) are selected from the above group.

In preferred embodiments the first and second gene (and third gene, if present) are selected from the group consisting of the genes which encode for Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), and vATPase subunit C (vATPc; GenBank accession number ADDG01035752.1) (SEQ ID NO: 17). In even more preferred embodiments, the first or second gene encodes Monoamine Oxidase (MOA; GenBank accession number ADDG01053234.1) (SEQ ID NO: 15).

In preferred embodiments the first and second nucleic acid sequence (and third nucleic acid sequence, if present) comprises a nucleic acid sequence that has 100% sequence identity to at least 21 contiguous nucleotides (such as at least 25, 30, 50, 100, 200 or 500 nucleotides) encoded by a sequence selected from the group consisting of SEQ ID NO.1, SEQ ID NO.2, and SEQ ID NO.3. In even more preferred embodiments, the first or second nucleic acid sequence is SEQ ID NO.2.

In one embodiment the present invention provides a nucleic acid concatemer comprising the nucleic acid sequences SEQ IDs 12, 13 and 14.

In some embodiments, the present invention provides a single nucleic acid agent that comprises at least two nucleic acid sequences, each of which is capable of downregulating the expression of a gene from *Varroa destructor*, as described herein. In preferred embodiments, each of the sequences is capable of downregulating the expression of a different gene from *Varroa destructor*.

Nucleic Acids, Concatemers and Constructs

Nucleic acid agents and concatemers according to the present invention will be recombinant and may be provided isolated and/or purified, in substantially pure or homogeneous form, or free or substantially free of other nucleic acid. The term "isolated" encompasses all these possibilities.

Nucleic acids may be ribonucleic acids or deoxy ribonucleic acids. In some embodiments the nucleic acid agent is a dsRNA, such as siRNA, shRNA or miRNA. In other embodiments the nucleic acid agent is antisense RNA, or a ribozyme.

Since nucleic acid may be double stranded, where nucleic acid agent (or nucleotide sequence) of the invention is referred to herein, use of the complement of that nucleic acid agent (or nucleotide sequence) will also be embraced by the invention. The 'complement' in each case is the same length as the reference, but is 100% complementary thereto whereby by each nucleotide is base paired to its counterpart i.e. G to C, and A to T or U.

In some embodiments the nucleic acid agent is less than 2000 bases (or base pairs) long. For example, in some embodiments the nucleic acid is less than 1800 bases long, such as less than 1600, 1400, 1200 or less than 1000 bases (or base pairs) long. In some embodiments the nucleic acid is less than 950 bases long, such as less than 900, 850, 800, 750, 700, 650, 600, 550, 500, 450, 400, 300, 250, 200, 150, 100 or less than 50 bases long. In some preferred embodiments the nucleic acid is less than 200 bases long. For clarity, it should be noted that a double-stranded nucleic acid consisting of two perfectly complementary strands, each 500 bases long, may be correctly described either as "500 bases long" or "500 base pairs long".

In some embodiments the total length of the nucleic acid concatemer is less than 10,000 bases (or base pairs) long. For example, in some embodiments the nucleic acid concatemer is less than 5000 bases long, such as less than 4000, 3000, 2000, 1500, 1000, 500, 400, 300, 200 or less than 100 bases (or base pairs) long. In some embodiments the nucleic acid concatemer is less than 950 bases long, such as less than 900, 850, 800, 750, 700, 650, 600, 550, 500, 450, 400, 300, 250, 200, 150, 100 or less than 50 bases long. In preferred embodiments the total length of the nucleic acid concatemer less than 1000 bases (or base pairs) long. In more preferred embodiments the total length of the nucleic acid concatemer less than 500 bases (or base pairs) long. (The "total length of the concatemer" as used herein is measured from the first base of the 5'-most sequence capable of down-regulating gene expression to the last base of the 3'-most sequence capable of down-regulating gene expression.)

The present invention also provides nucleic acid constructs encoding nucleic acid agents (or concatemers) according to the present invention. Such vectors may include, in addition to the sequence encoding the nucleic acid agent of the invention, a promoter, a terminator and/or other regulatory sequence such as to define an expression cassette comprising the sequence encoding the nucleic acid agent of the invention. One such vector according to the present invention has the nucleic acid sequence shown in SEQ ID NO. 11.

Generally speaking, in the light of the present disclosure, those skilled in the art will be able to construct vectors according to the present invention. For further details see, for example, Molecular Cloning: a Laboratory Manual: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Protocols in Molecular Biology, Second Edition, Ausubel et al. eds., John Wiley & Sons, 1992.

Genes and Gene Expression

"Gene of the *Varroa destructor* mite" is a term used to mean a coding sequence in the genome of the *Varroa destructor* which is, or may be, expressed as a functional gene product. For example, via transcription to mRNA and translation to a protein according to well established principles.

Expression of a gene is a term used to describe the process by which the information from, a gene is used to synthesise a gene product, such as an mRNA or polypeptide.

"Capable of downregulating the expression" is a term generally used to refer to the ability to reduce the levels of a gene product in response to the presence of the agent. Reduction is measured compared to an otherwise identical gene expression system which has not been exposed to the agent in question. The degree of reduction may be so as to totally abolish production of the encoded gene product, but may also be such that the abolition of expression is not complete, with some small degree of expression remaining. The term should not therefore be taken to require a complete absence of expression. It is used herein where convenient because those skilled in the art well understand this. Examples of downregulated expression are (i) reduced transcription of the gene, (ii) reduced mRNA amount, stability or translatability, and (iii) reduced amount of polypeptide product.

The ability to downregulate expression can be assayed, for example, via direct detection of gene transcripts (e.g. via PCR) or polypeptides (e.g. via Western blot), via polypeptide activity (e.g. enzyme activity) or via observation of *Varroa destructor* mite behaviour (e.g. via mortality). Thus, whether a particular agent inhibits translation of mRNA, or induces degradation of mRNA, can be readily assayed using the above methods, or other methods well-known in the art. In some embodiments, translation of an mRNA is considered "inhibited" if the amount of expressed protein is at least 10% lower than in an otherwise identical system not exposed to the agent; for example, at least 20% lower, at least 30% lower, at least 40% lower, at least 50% lower, at least 60% lower, at least 70% lower, at least 80% lower, or at least 90% lower than in an otherwise identical system not exposed to the agent. Similarly, in some embodiments, degradation of mRNA is "induced" if the amount of mRNA (µg/µl) is at least 10% lower than in an otherwise identical system not exposed to the agent; for example, at least 20% lower, at least 30% lower, at least 40% lower, at least 50% lower, at least 60% lower, at least 70% lower, at least 80% lower, at least 90% lower, at least 95% lower, at least 98% lower, or at least 99% lower than in an otherwise identical system not exposed to the agent.

Thus, in some embodiments the mRNA levels of the targeted genes in treated *Varroa destructor* mites are at least 10% lower than in mites treated with a control agent (for example, GFP dsRNA). For example, mRNA levels (µg/µl) of the targeted genes may be at least 20% lower, at least 30% lower, at least 40% lower, at least 50% lower, at least 60% lower, at least 70% lower, at least 80% lower, at least 90%, at least 95%, at least 98%, or at least 99% lower than in mites treated with a control agent (for example, GFP dsRNA).

In some embodiments the amount of protein or mRNA is measured 24 hours after the system is first exposed to the agent. In other embodiments the amount of protein or mRNA is measured 48 or 72 hours after the system is first exposed to the agent, composition or concatemer.

In preferred embodiments, the mRNA levels of the targeted genes in treated *Varroa destructor* mites are at least 95% lower than in mites treated with a control agent (for example, GFP dsRNA) 72 hours after exposure to the agent, composition or concatemer.

*Varroa* Mite Mortality

The effectiveness of the isolated nucleic acid agent (or concatemer) disclosed herein, for example in methods of treating or preventing a *Varroa destructor* mite infestation of a beehive, may be assessed by monitoring the % mortality of *Varroa destructor* mites on bees treated with the nucleic acid agents.

For example, in some embodiments the nucleic acid agent causes greater than 30% mite mortality (=less than 70% mite survival), as measured 108 hours after a 12 hour soaking of the mite in a 1.25 µg/µl solution of the nucleic acid agent. In some embodiments the nucleic acid agent causes greater than 40% mite mortality, such as greater than 50%, greater than 60%, greater than 70%, greater than 80%, or greater than 90% mortality as measured 108 hours after a 12 hour soaking of the mite in a 1.25 µg/µl solution of the nucleic acid agent.

In preferred embodiments, the nucleic acid agent causes greater than 60% mite mortality (=less than 40% mite survival), as measured 108 hours after a 12 hour soaking of the mite in a 1.25 µg/µl solution of the nucleic acid agent In some embodiments, mite mortality is assessed as set out in Example 5.

Interaction with Non-*Varroa* Genes

The mechanisms of gene downregulation described above are widespread throughout a broad range of organisms. Thus, in situations where the nucleic acid agent will come into contact with more than one variety of organism, it is preferable to ensure that only the target organism (in this case, the *Varroa* mite) is susceptible to expression downregulation by the agent. That is, gene expression in non-target organisms exposed to the nucleic acid agent should preferably remain unaltered.

Such species-specific gene downregulation can be achieved by ensuring (i) that the nucleic acid agents selected do not possess sufficient sequence identity with any non-target organism to induce repression of gene expression in those non-target organisms, or (ii) that the nucleic acid agent are only expressed in the target organism (by, for example, through using a construct having a *Varroa* specific promoter). So, in the present case, it is desirable that any nucleic acid agent selected for its ability to downregulate a gene of *Varroa destructor* is not capable of significantly downregulating any gene in another organism, such as the bee host, or a human which may consume honey produced by the hive.

Accordingly, the nucleic acid agent (or concatemer) of the present invention is capable of specifically down-regulating the *Varroa destructor* version of a given gene (e.g. AChE, or MOA). In some embodiments the nucleic acid agent of the present invention is capable of downregulating the *Varroa destructor* gene to a significantly greater extent than the equivalent bee gene or genes; for example, the nucleic acid agent may induce a reduction in the *Varroa* gene product that is at least 2-fold greater than the reduction in an equivalent bee gene product (for example, if the nucleic acid agent causes a 70% reduction in *Varroa* mRNA levels, there will be no more than a 35% reduction in bee mRNA levels). In some embodiments the nucleic acid agent may induce a reduction in *Varroa* gene product that is at least 3-fold, 4-, 5-, 6-, 8-, 10-, 20-, 50-, 100-, 200-, 500- or 1000-fold greater than the reduction in an equivalent bee gene product. In this regard, an "equivalent bee gene product" is a bee gene product identified as fulfilling the same role or function as the targeted *Varroa* gene.

In some embodiments the nucleic acid agent (or concatemer) of the present invention is capable of downregulating the *Varroa destructor* gene to a significantly greater extent than any bee gene or human gene. For example, the nucleic acid agent may induce a reduction in the *Varroa* gene product that is at least 2-fold greater than the reduction in any bee gene product or any human gene product (for example, if the nucleic acid agent causes a 70% reduction in *Varroa* mRNA levels, there will be no more than a 35% reduction in any bee or human mRNA level). In some embodiments the nucleic acid agent may induce a reduction in *Varroa* gene product that is at least 3-fold, 4-, 5-, 6-, 8-, 10-, 20-, 50-, 100-, 200-, 500- or 1000-fold greater than the reduction in any bee gene product or human gene product.

Thus, in some embodiments the nucleic acid agents (or concatemers) of the present invention target do not comprise a nucleic acid sequence that has at least 50% sequence identity to at least 18 contiguous nucleotides encoded by the bee (e.g. *Apis mellifera*) or human genome. In some embodiments the nucleic acid agents of the present invention do not comprise a nucleic acid sequence that has at least 50% sequence identity to at least 18 contiguous nucleotides encoded by a bee (e.g. *Apis mellifera*) or human mRNA.

In some embodiments, the nucleic acid agent (or concatemer) according to the present invention does not comprise a nucleic acid sequence that has 100% sequence identity to at least 18 (for example, at least 21) contiguous nucleotides of the bee (e.g. *Apis mellifera*) or human genome.

The species specificity of gene regulation may also be assayed through monitoring the mortality of bees treated with the isolated nucleic acid agent (or concatemer). For example, in some embodiments there is less than an additional 10% bee mortality (relative to an untreated control), as measured 168 hours after the onset of treatment of the bee population with the isolated nucleic acid agent. In some embodiments there is less than an additional 5%, 2%, 1%, 0.5%, 0.2%, 0.1% bee mortality (relative to an untreated control), as measured 168 hours after the onset of treatment of the bee population with the isolated nucleic acid agent. In preferred embodiments, there is no significant additional bee mortality (relative to an untreated control, as measured 168 hours after the onset of treatment of the bee population with the isolated nucleic acid agent).

Delivery of Nucleic Acids to *Varroa destructor* Mites

In order to influence the expression of genes from *Varroa destructor* the nucleic acid agent of the present invention must be delivered to the *Varroa destructor* mite.

Delivery of the nucleic acid agents or concatemers of the present invention to the *Varroa destructor* mite can be achieved in several ways. For example, the nucleic acid agents may be delivered to the mites directly by contacting the bees or beehive with a solution of the nucleic acid agents, for example by spraying a solution of the nucleic acid agents or concatemers directly onto a beehive infested by *Varroa* mites; on contact with the mites, the nucleic acid agents or concatemers can enter the mite body via diffusion or transfer through orifices on the mite body.

Accordingly, the present invention provides a solution comprising a nucleic acid agent, nucleic acid composition, or concatemer of the invention for use in a method of treating or preventing a *Varroa destructor* mite infestation of a beehive. The present invention also provides for the use of a solution comprising a nucleic acid agent, nucleic acid composition, or concatemers of the invention in the manufacture of a medicament for the treatment or prevention of a *Varroa destructor* mite infestation of a beehive. The present invention further provides a method of treating or preventing a *Varroa destructor* mite infestation of a beehive, the method comprising spraying, or otherwise contacting, the beehive or members of the beehive with a solution comprising a nucleic acid agent, nucleic acid composition, or concatemer of the invention.

Nucleic acid agents or concatemers of the present invention may be delivered to the *Varroa destructor* mite indirectly via administering the nucleic acid to the mites' bee host. This is possible because *Varroa destructor* mites parasitize bee pupae and adults by puncturing the bee's exoskeleton and feeding on the bee's heamolymph; therefore, the *Varroa destructor* mites will ingest compounds present in the bee's heamolymph, including nucleic acid agents or concatemers of the invention. This indirect delivery method has been shown to effectively transfer dsRNAs from bees fed the dsRNAs to parasitizing *Varroa destructor* mites [8], [9].

According to another embodiment of the present invention, the nucleic acid agents or concatemers of the present invention are delivered to the *Varroa destructor* mites indirectly via bees (such as *A.meffifera*) parasitized by the mites. The nucleic acid agents or concatemers of the present invention may be delivered to the bees by, for example, spraying or otherwise contacting the beehive or members of the beehive with a solution comprising a nucleic acid agent, nucleic acid composition, or concatemer of the invention.

The nucleic acid agents or concatemers of the present invention may be delivered to the bees by feeding the nucleic acids to the bees. Supplemental feeding of bees is already well-established amongst bee-keepers for both nutritional and other needs of beehives [10], with bees known to consume a wide variety of foodstuff in addition to their preferred food of pollen and honey. These, or any other suitable, foodstuff may be supplemented with nucleic acid agents or concatemers of the invention in order to deliver the nucleic acids or concatemers to the bees.

Accordingly, the present invention provides a composition for feeding to bees comprising an isolated nucleic acid agent, a nucleic acid composition or concatemer of the invention. In addition to the isolated nucleic acid agent, nucleic acid composition, or concatemer of the invention, the composition for feeding to bees may comprise honey, pollen or non-typical foods such as Wheast (a dairy yeast grown on cottage cheese), soybean flour, yeast (e.g. brewer's yeast, torula yeast), yeast products, soybean flour, sugar and sugar-syrup. In some embodiments the sugar or sugar-syrup is made from cane or beet sugar, isomerized corn syrup, or type-50 sugar syrup. In some embodiments the composition for feeding to bees comprises protein, for example at least 10% by weight of pollen, for example 10-12%, 10-15%, 10-20%, 20-35%, 25-35% or 25-30% by weight of pollen.

The present invention further provides a composition for feeding to bees according to the present invention for use in a method of treating or preventing a *Varroa destructor* mite infestation of a beehive. The present invention also provides for the use of a composition for feeding to bees according to the present invention in the manufacture of a medicament for the treatment or prevention of a *Varroa destructor* mite infestation of a beehive. The present invention further provides a method of treating or preventing a *Varroa destructor* mite infestation of a beehive, the method comprising feeding bees with a composition for feeding to bees according to the present invention.

"Treating or Preventing a *Varroa destructor* Mite Infestation of a Beehive"

It is accepted that harm to bees and hives from *Varroa destructor* mite infestation of a beehive does not only come from the direct effect of *Varroa* mites feeding on bees. In addition to this direct effect, the feeding of *Varroa* mites weakens individual bee's immune systems and other natural defences (by, for example, piercing the bee's exoskeleton), thereby increasing the bee's susceptibility to other biological pathogens (for example, viral, bacterial, or fungal pathogens) as well as chemical agents (for example, pesticides such as neonicotinoids). The increased pathogenicity applies to both sporadically encountered pathogens, and those pandemic pathogens (such as Deformed Wing Virus, DWV) which are typically found at a low level in even 'healthy' bee colonies. This progressive weakening of a bee colony's ability to resist the onslaught from a range of environmental challenges is believed to result in a catastrophic collapse in bee numbers (often referred to as Colony Collapse Disorder (CCD) or 'Colony loss').

Accordingly, agents and/or methods of treating or preventing *Varroa destructor* mite infestation of a beehive are also be effective for treating, preventing, and/or reducing the susceptibility of honeybees (or beehives) to CCD, as well as the individual specific pathogens associated with CCD.

Thus, the terms "treating or preventing a *Varroa destructor* mite infestation of a beehive" and "treatment or prevention of a *Varroa destructor* mite infestation of a beehive" (or equivalents thereof) as used herein encompasses:

"treatment or prevention of Colony Collapse Disorder (CCD) in honeybees";
"reducing the susceptibility of honeybees to Colony Collapse Disorder (CCD)";
"treatment or prevention of honeybees colony loss";
"reducing the susceptibility of honeybees to colony loss";
"treatment or prevention of a bacterial infection (such as *Melissococcus pluton*) in a honeybee";
"reducing the susceptibility of honeybees to a bacterial infection (such as *Melissococcus pluton*)";
"treatment or prevention of a viral infection (such as deformed wing virus (DWV), Kashmir bee virus (KBV), acute bee paralysis virus (ABPV), Israel Acute Paralysis Virus (IAPV), or black queen cell virus (BQCV)) in a honeybee";
"reducing the susceptibility of honeybees to a viral infection (such as deformed wing virus (DWV), Kashmir bee virus (KBV), acute bee paralysis virus (ABPV), Israel Acute Paralysis Virus (IAPV), or black queen cell virus (BQCV)";
"treatment or prevention of a fungal infection in a honeybee";
"reducing the susceptibility of honeybees to a fungal infection;
"treatment or prevention of a nematode infection in a honeybee";
"reducing the susceptibility of honeybees to a nematode infection;
"treatment or prevention of a parasite infection (such as a protozoan or mite) in a honeybee"; and,
"reducing the susceptibility of honeybees to a parasite infection (such as a protozoan or mite).

SOME SPECIFIC EMBODIMENTS

Some specific embodiments will now be described by way of non-limiting examples of the present invention.

In one embodiment the present invention provides an isolated dsRNA less than 2000 bases long comprising a nucleic acid sequence that is capable of downregulating the expression of a gene of the *Varroa destructor* mite, wherein the gene encodes Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PITH; GenBank accession number ADDG01000788.1) (SEQ ID NO: 22), Crustacean hyperglycaemic hormone (CHH; GenBank accession number ADDG01078386.1) (SEQ ID NO: 23) or Glutathione transferase mu1 (GSTµ1; GenBank accession number ADDG01001667.1) (SEQ ID NO: 24);

wherein the nucleic acid sequence has 100% sequence identity to at least 18 contiguous nucleotides of an mRNA encoded by the gene of the *Varroa destructor* mite, and wherein the nucleic acid agent induces the degradation of the mRNA.

In one embodiment the present invention provides an isolated dsRNA less than 2000 bases long comprising a nucleic acid sequence that has 100% sequence identity to at least 18 contiguous nucleotides of an mRNA encoded by a gene of the *Varroa destructor* mite, and wherein the nucleic acid agent induces the degradation of the mRNA, wherein the at least 18 contiguous nucleotides are encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising a nucleic acid sequence that has 100% sequence identity to at least 25 contiguous nucleotides of an mRNA encoded by a gene of the *Varroa destructor* mite, and wherein the nucleic acid agent induces the degradation of the mRNA,
  wherein the at least 25 contiguous nucleotides are encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising a nucleic acid sequence that has 100% sequence identity to at least 30 contiguous nucleotides of an mRNA encoded by a gene of the *Varroa destructor* mite, and wherein the nucleic acid agent induces the degradation of the mRNA,
  wherein the at least 30 contiguous nucleotides are encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising a nucleic acid sequence that is capable of downregulating the expression of a gene of the *Varroa destructor* mite, wherein the gene encodes Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), or
  vATPase subunit C (vATPc; GenBank accession number ADDG01035752.1 (SEQ ID NO: 17);
  wherein the nucleic acid sequence has 100% sequence identity to at least 18 contiguous nucleotides of an mRNA encoded by the gene of the *Varroa destructor* mite, and wherein the nucleic acid agent induces the degradation of the mRNA.

In one embodiment the present invention provides an isolated dsRNA less than 2000 bases long comprising a nucleic acid sequence that has 100% sequence identity to at least 18 contiguous nucleotides of an mRNA encoded by a gene of the *Varroa destructor* mite, and wherein the nucleic acid agent induces the degradation of the mRNA,
  wherein the at least 18 contiguous nucleotides encoded by SEQ ID NO.1, SEQ ID NO.2, or SEQ ID NO.3.

In one embodiment the present invention provides an isolated dsRNA less than 2000 bases long comprising a nucleic acid sequence that has 100% sequence identity to at least 25 contiguous nucleotides of an mRNA encoded by a gene of the *Varroa destructor* mite, and wherein the nucleic acid agent induces the degradation of the mRNA,
  wherein the at least 25 contiguous nucleotides encoded by SEQ ID NO.1, SEQ ID NO.2, or SEQ ID NO.3.

In one embodiment the present invention provides an isolated dsRNA less than 2000 bases long comprising a nucleic acid sequence that has 100% sequence identity to at least 30 contiguous nucleotides of an mRNA encoded by a gene of the *Varroa destructor* mite, and wherein the nucleic acid agent induces the degradation of the mRNA,
  wherein the at least 30 contiguous nucleotides encoded by SEQ ID NO.1, SEQ ID NO.2, or SEQ ID NO.3.

In one embodiment the present invention provides an isolated dsRNA less than 2000 bases long comprising at least two nucleic acid sequences which are capable of downregulating the expression of at least two genes of the *Varroa destructor* mite, wherein the genes are selected from the genes which encode Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PITH; GenBank accession number ADDG01000788.1) (SEQ ID NO: 22), Crustacean hyperglycaemic hormone (CHH;
  GenBank accession number ADDG01078386.1) (SEQ ID NO: 23) or Glutathione transferase mu1 (GSTμ1; GenBank accession number ADDG01001667.1) (SEQ ID NO: 24);
  wherein each nucleic acid sequence independently has 100% sequence identity to at least 18 contiguous nucleotides of an mRNA encoded by the gene of the *Varroa destructor* mite, and wherein the nucleic acid agent induces the degradation of the mRNA.

In one embodiment the present invention provides an isolated dsRNA less than 2000 bases long comprising at least three nucleic acid sequences which are capable of downregulating the expression of at least three genes of the *Varroa destructor* mite, wherein the genes are selected from the genes which encode Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PITH; GenBank accession number ADDG01000788.1) (SEQ ID NO: 22), Crustacean hyperglycaemic hormone (CHH;
  GenBank accession number ADDG01078386.1) (SEQ ID NO: 23) or Glutathione transferase mu1 (GSTμ1; GenBank accession number ADDG01001667.1) (SEQ ID NO: 24);
  wherein each nucleic acid sequence independently has 100% sequence identity to at least 18 contiguous nucleotides of an mRNA encoded by the gene of the *Varroa destructor* mite, and wherein the nucleic acid agent induces the degradation of the mRNA.

In one embodiment the present invention provides an isolated dsRNA less than 2000 bases long comprising at least two nucleic acid sequences that independently have 100% sequence identity to at least 18 contiguous nucleotides of an mRNA encoded by a gene of the *Varroa destructor* mite, and wherein the nucleic acid agent induces the degradation of the mRNA,
  wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising at least two nucleic acid sequences that independently have 100% sequence identity to at least 25 contiguous nucleotides of an mRNA encoded by a gene of the *Varroa destructor* mite, and wherein the nucleic acid agent induces the degradation of the mRNA, wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising at least two nucleic acid sequences that independently have 100% sequence identity to at least 30 contiguous nucleotides of an mRNA encoded by a gene of the *Varroa destructor* mite, and wherein the nucleic acid agent induces the degradation of the mRNA, wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising at least three nucleic acid sequences that independently have 100% sequence identity to at least 18 contiguous nucleotides of an mRNA encoded by a gene of the *Varroa destructor* mite, and wherein the nucleic acid agent induces the degradation of the mRNA, wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising at least three nucleic acid sequences that independently have 100% sequence identity to at least 25 contiguous nucleotides of an mRNA encoded by a gene of the *Varroa destructor* mite, and wherein the nucleic acid agent induces the degradation of the mRNA, wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides an isolated dsRNA less than 2000 bases long comprising at least three nucleic acid sequences that independently have 100% sequence identity to at least 30 contiguous nucleotides of an mRNA encoded by a gene of the *Varroa destructor* mite, and wherein the nucleic acid agent induces the degradation of the mRNA, wherein the at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

In one embodiment the present invention provides a nucleic acid construct encoding either or both strands of any one of the isolated nucleic acid agents of the present invention described in this "Embodiments of the present invention" section.

In one embodiment the present invention provides a nucleic acid composition comprising at least two isolated nucleic acid agents of the present invention, wherein the dsRNA's are capable of downregulating the expression of at least two genes selected from Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), and vATPase subunit C (vATPc; GenBank accession number ADDG01035752.1 (SEQ ID NO: 17).

In one embodiment the present invention provides a nucleic acid composition comprising at least three isolated nucleic acid agents of the present invention, wherein the dsRNA's are capable of downregulating the expression of the *Varroa destructor* mite genes Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), and vATPase subunit C (vATPc; GenBank accession number ADDG01035752.1 (SEQ ID NO: 17).

In one embodiment the present invention provides a nucleic acid composition comprising at least two isolated nucleic acid agents of the present invention, wherein the composition comprises at least two of:

(1) a dsRNA comprising 18 contiguous nucleotides encoded by SEQ ID NO.1;
(2) a dsRNA comprising 18 contiguous nucleotides encoded by SEQ ID NO.2; and
(3) a dsRNA comprising 18 contiguous nucleotides encoded by SEQ ID NO.3.

In one embodiment the present invention provides a nucleic acid composition comprising at least three isolated nucleic acid agents of the present invention, wherein the composition comprises:

(1) a dsRNA comprising 18 contiguous nucleotides encoded by SEQ ID NO.1;
(2) a dsRNA comprising 18 contiguous nucleotides encoded by SEQ ID NO.2; and
(3) a dsRNA comprising 18 contiguous nucleotides encoded by SEQ ID NO.3.

In one embodiment the present invention provides a composition for feeding to bees comprising an isolated dsRNA, or a nucleic acid composition, described in this "Embodiments of the present invention" section.

Contemplated Combinations

1. An isolated nucleic acid agent according to any one of paragraphs 4 to 13, a nucleic acid composition according to either one of paragraphs 15 or 16, or a composition according to paragraph 17 for use in a method of treating or preventing a *Varroa destructor* mite infestation of a beehive.

2. Use of an isolated nucleic acid agent according to any one of paragraphs 4 to 13, a nucleic acid composition according to either one of paragraphs 15 or 16, or a composition according to paragraph 17 in the manufacture of a medicament for the treatment or prevention of a *Varroa destructor* mite infestation of a beehive.

3. A method of treating or preventing a *Varroa destructor* mite infestation of a beehive, the method comprising administering to a member of the beehive an isolated nucleic acid agent according to any one of paragraphs 4 to 13, a nucleic acid composition according to either one of paragraphs 15 or 16, or a composition according to paragraph 17.

4. An isolated nucleic acid agent comprising a nucleic acid sequence that is capable of downregulating the expression of a gene of the *Varroa destructor* mite, wherein the gene encodes Acetylcholinesterase (AChE; GenBank accession number ADDG01069748.1) (SEQ ID NO: 16), Monoamine Oxidase (MOA; GenBank accession number ADDG01053234.1) (SEQ ID NO: 15), vATPase subunit C (vATPc; GenBank accession number ADDG01035752.1 (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1)

(SEQ ID NO: 21), Prothoracicostatic peptide precursor (PITH; GenBank accession number ADDG01000788.1) (SEQ ID NO: 22), Crustacean hyperglycaemic hormone (CHH;

GenBank accession number ADDG01078386.1) (SEQ ID NO: 23) or Glutathione transferase mu1 (GSTμ1; GenBank accession number ADDG01001667.1) (SEQ ID NO: 24).

5. The isolated nucleic acid agent according to paragraph 4, wherein the nucleic acid agent comprises at least two or at least three nucleic acid sequences, wherein, optionally, the at least two or at least three nucleic acid sequences are capable of downregulating the expression of at least two or at least three different genes from *Varroa destructor*.

6. The isolated nucleic acid agent according to either one of paragraph 4 or paragraph 5, wherein the agent is less than 2000 bases long, or less than 1000 bases long, less than 500 bases long.

7. The isolated nucleic acid agent according to any one of paragraph 4 to paragraph 6 wherein the or each nucleic acid sequence independently has at least 80% sequence identity to at least 18 contiguous nucleotides of an mRNA encoded by the gene of the *Varroa destructor* mite, and wherein the nucleic acid agent inhibits translation of the mRNA.

8. The isolated nucleic acid agent according to paragraph 7 wherein the or each nucleic acid sequence independently has at least 80% sequence identity to at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

9. The isolated nucleic acid agent according to any one of paragraph 4 to paragraph 6 wherein the or each nucleic acid sequence independently has 100% sequence identity to at least 18 contiguous nucleotides of an mRNA encoded by the gene of the *Varroa destructor* mite, and wherein the nucleic acid agent induces the degradation of the mRNA.

10. The isolated nucleic acid agent according to paragraph 9 wherein the or each nucleic acid sequence independently has 100% sequence identity to at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

11. The isolated nucleic acid agent according to any one of paragraphs 4 to 10 wherein the nucleic acid agent is a dsRNA, antisense RNA, or a ribozyme.

12. The isolated nucleic acid agent according to paragraph 11 wherein the dsRNA is an siRNA, shRNA or miRNA.

13. The isolated nucleic acid agent according to any one of paragraphs 7 to 12 wherein the at least 18 contiguous nucleotides is at least 21 contiguous nucleotides, at least 25 contiguous nucleotides, or at least 30 contiguous nucleotides.

14. A nucleic acid construct encoding the isolated nucleic acid agent of any one of paragraphs 4 to 13.

15. A nucleic acid composition comprising at least two isolated nucleic acid agents according to any one of paragraphs 4 to 13.

16. The nucleic acid composition according to paragraph 15 wherein the at least two isolated nucleic acid agents are capable of downregulating the expression of at least two of the genes of the *Varroa destructor* mite.

17. A composition for feeding to bees comprising an isolated nucleic acid agent according to any one of paragraphs 4 to 13 or a nucleic acid composition according to either one of paragraphs 15 or 16.

FIGURES

FIG. 1. *V.destructor* mite survival following GST-μ1 knockdown via soaking (LacZ control).

FIG. 2. Knockdown of PTTH expression via soaking (LacZ control).

FIG. 3. *V.destructor* mite survival following PTTH knockdown via soaking (LacZ control). Significant variability was observed between experiments.

FIG. 4. *V.destructor* mite survival following AChE knockdown via soaking (LacZ control).

FIG. 5. *V.destructor* mite survival following MOA knockdown via soaking (LacZ control).

FIG. 6. *V.destructor* mite survival following vATPc knockdown via soaking (LacZ control).

FIG. 7. *V.destructor* mite survival following CHS knockdown (LacZ control).

FIG. 8. *V.destructor* mite survival following PyK knockdown (LacZ control).

FIG. 9. *V.destructor* mite survival following GABA knockdown (LacZ control).

FIGS. 10 (A & B) *V.destructor* mite survival following knockdown of vATPc and/or MOA (LacZ control). All challenges had final concentration of 1.25 ug/μl dsRNA.

FIG. 11. *V.destructor* mite survival following knockdown of vATPc and/or MOA (LacZ control). Each dsRNA had a final concentration of 1.25 ug/μl dsRNA, meaning the total dsRNA concentration of the vATPc/MOA assay was 2.5 ug/μl, whilst that of the vATPc or MOA single assay was 1.25 ug/μl.

FIG. 12. *V.destructor* mite survival following knockdown of vATPc and/or MOA and/or AChE (LacZ control). Each dsRNA had a final concentration of 1.25 ug/μl dsRNA (as in FIG. 11)

FIG. 13. L4440-MOA-V-ATPC-ACHE-Tricatemer plasmid map: MOA, vATPc, and AChE targets are indicated FIG. 14. Effect of different dsRNA treatment on *Varroa* mite mortality. In groups of 10, mites were soaked overnight at 4° C. in 40 μl 0.9% saline containing various dsRNA treatments. Subsequently, mites were maintained on *Apis mellifera* larvae in Petri dishes at 30° C. and 85% RH. Mortality was observed over 105 hours post-treatment. Each treatment consisted of three petri dishes containing 10 mites (n=3).

FIG. 15. Effect of different dsRNA treatment on *Varroa* mite mortality. In groups of 10, mites were soaked overnight at 4° C. in 40 μl 0.9% saline containing various dsRNA treatments. Subsequently, mites were maintained on *Apis mellifera* larvae in Petri dishes at 30° C. and 85% RH. Each treatment consisted of three petri dishes containing 10 mites (n=3). Effect of treatments on mite mortality at 105 hours post-treatment was assessed initially by oneway-ANOVA and pairwise comparisons determined by Fisher's LSD. Treatments that do not share a letter are significantly different ($P<0.05$).

DEFINITIONS

Bee and Beehive

As used herein, the term "bee" is used to refer to adult insects and pupal forms thereof in the superfamily Apoidea, order Hymenoptera. Example genus' include Apis, *Bombus*, *Trigona* and *Osmia*. In some embodiments the bee is selected from the following species: *Apis mellifera, Apis cerena* and *Bombus terrestris*.

As used herein, the term beehive is used to refer to a population of bees living together, normally under a single queen.

Percentage Identity

As used herein, the term "percentage sequence identity" refers to identity as measure over the entire length of the SEQ ID in question.

For example, a polypeptide comprising a sequence having 70% sequence identity to SEQ ID NO:1 would contain a contiguous polypeptide where:

(Number of amino acids identical to SEQ ID NO 1)/Total number of amino acids in SEQ ID NO 1=0.7

The percent identity of two amino acid or two nucleic acid sequences can be determined by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al., 1984, Nucl. Acids Res. 12: 387). The preferred default parameters for the 'GAP' program includes: (1) The GCG implementation of a unary comparison matrix (containing a value of 1 for identities and 0 for non-identities) for nucleotides, and the weighted amino acid comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps.

Independently

As used herein, the term "independently" is used with reference to nucleic acid sequences within a single nucleic acid agent to indicate that the features of each sequence should be considered independently of any other sequences in a particular agent.

Thus, for example, "an isolated nucleic acid agent comprising at least two nucleic acid sequences wherein each nucleic acid sequence independently has at least 80% sequence identity to at least 18 contiguous nucleotides encoded by SEQ ID NO.1, SEQ ID NO.2, SEQ ID NO.3, SEQ ID NO.4, SEQ ID NO.5, SEQ ID NO.6, SEQ ID NO.7, SEQ ID NO.8, SEQ ID NO.9, or SEQ ID NO.10" encompasses an isolated nucleic acid agent wherein (for example) one nucleic acid sequence has identity to SEQ ID NO.1 and another has identity to SEQ ID NO.2. That is, both sequences do not have to have identity to the same SEQ ID (since they are independent).

Statistical Significance

Unless stated otherwise, the significance of overall treatment effect is assessed by oneway-ANOVA and, if there a significant effect is detected, pairwise comparisons are performed by Fisher's least significant difference method. Statistical analysis is performed using Minitab Vers 16.0.

Unless stated otherwise, significance is assessed at the $P<0.05$ level

Following a description of the experimental methods employed by the present inventors, some particular embodiments of the invention will be discussed.

Materials and Methods

Mite Collection and Husbandry

*Varroa destructor* (adult female) mites were collected from capped brood cells frames from *Apis mellifera* hives in York, England that had purposefully been left untreated for *Varroa* control. Prior to harvesting mites the frames were maintained at 27° C. in a 80% relative humidity environment, 15.5 h:8.5 h, light:dark regime. Mites were attached ventral side down on double sided tape attached to Petri dishes and approximately 50 were harvested for synganglion in phosphate buffered saline (PBS) before being washed in sterile ice-cold PBS and pooled together in a 1.5 ml eppendorf tube containing 200 µl RNA-later (Sigma, Poole, UK). Prior to RNA extraction, an additional 450 µl dissection buffer was added to sample tubes and centrifuged at 14000 rpm for 15 min. Supernatant was removed and the synganglion washed with fresh PBS before a final centrifuge again at 14000 rpm for 15 min. Supernatant was again removed and 600 µl ZR extraction buffer added to each tissue sample. Total RNA was extracted using a mini-RNA isolation II Kit (Zymo Research, Orange, Calif., USA), as per manufacturer's instructions and eluted in 50 µl water. RNA was co-precipitated with 1.5 µl glycogen blue (NEB Biolabs, Ipswich, UK) and 2 µl 3M sodium acetate in 95% ethanol and resuspended in 5 µl of DEPC-treated water.

Methods to brood *Varroa* by artificial in vitro feeding have been tested. "Feeding units" utilising parafilm and artificial liquid food containing blue dye have been successful in showing that adult *Varroa* will feed as measured by the presence/absence after 48 h of blue excretions. Adult *Varroa* have successfully lived in these chambers for up to 14 days although mortality is still high compared with mites living on fresh bee larvae.

Generation of a *Varroa destructor* cDNA Library 3.5 µl (0.5 µg) of total *Varroa destructor* RNA was used for first strand cDNA synthesis. The construction of cDNA libraries was done using the SMART cDNA library construction kit (Clontech, St-Germain-en-Laye, France) according to the protocol provided by manufacturer, with some modifications. To determine optimal number of cycles, two identical amplification reactions were prepared. After the 10th amplification cycle the first reaction was stored on the ice, while the second one was used for the PCR cycle number optimization by removing 3 µl samples from the reaction every two cycles until cycle number 20. Samples were checked by visualization on a 1.1% agarose gel. The optimal number of cycles with visible and equally represented products, in this case 20 cycles, was used for primary amplification. cDNA was proteinase K treated, followed by phenol:chloroform extraction and resuspension in water. After SfiI digestion and size fractionation with Chroma Spin-400 column, the fractions were checked using agarose gel and pooled into large or medium libraries. Pooled cDNA was ethanol precipitated and eluted in 4 ul of water. 3 ul from each fraction was ligated into the λTripleEx2 vector and packed into phage using the Gigapack III Gold Packaging extract (Stratagene). Each un-amplified library was mixed with *E. coli* XL1 blue cells and top agar supplemented with X-gal and IPTG before being plated onto LB MgSO4 agar plates in serial dilutions of 1, 1:10, 1:100 and 1:1000. The large library consisted of $6.23 \times 10^6$ colony forming units (cfu)/ml and the medium library $1.07 \times 10^7$ cfu/ml with recombination of 94.3 and 96.3% respectively.

EST Sequencing and Target Selection 600 randomly selected recombinant plaques (white) were picked as agar plugs into plates of 96-wells, each well containing 100 µl of SM buffer (0.58% NaCl, 0.2% MgSO4.H2O 0.05M Tris-HCl, pH 7.5, 0.02% gelatin). Four plates were picked from the large fraction library, two from the medium fraction library and an additional 24 clones from the large fraction library for initial quality control. PCR with vector-specific primers was carried out using SM buffer/picked plaques as templates. PCR was carried out in 96-well plates containing 25 ul 2×Biomix (Bioline), 5 ul template, 1 ul (10 ng/ul) each of PT2F1 (5'-AAGTACTCTAGCAATT-GTGAGC-3'; SEQ ID NO: 25) and PT2R1 (5'-CTCT-TCGCTATTACGCCAGCTG-3'; SEQ ID NO: 26) and 18 ul water to give a 50 ul final reaction volume. Cycling conditions were 94° C. for 15 min followed by 33 cycles of 94° C. for 1 min, 49° C. for 1 min and 72° C. for 1 min 20 s. PCR products were sent to GATC (Konstanz, Germany) for PCR reaction clean up and sequenced using primer PT2F3 (5'-CTCGGGAAGCGCGCCATTGT-3'; SEQ ID NO: 27). PT2F3 is upstream from inserted cDNA and downstream from PT2F1 primer used in initial PCR reaction.

Following sequencing the Expressed sequence tags (ESTs) were modified in silico. ESTs were trimmed of primer and vector sequences, clusterized and checked for sequence quality using Lasergene Seqman (Lasergene v8.03, DNAstar, Madison, USA). BLASTn, BLASTx and tBLASTx programmes were used within the program BLAST2GO to compare the EST nucleotide sequences with the nonredundant (NR) databases of the NCBI and to the Gene Ontology (GO) database (www.blast2go.org). Following analysis of results, transcripts were primarily classified as novel sequences, putative identity or unknown function. Transcripts with a putative identity were further divided into functional categories by analysing GO identity and homology to known genes. Putative targets were chosen from the annotated sequences obtained in the EST library and were resequenced.

In addition, other putative targets were postulated based on their likelihood of having critical function in Acari and the likelihood of being fast-acting with little chance of having alternative rescue pathways. The whole genome shotgun database for *V. destructor* proved unsatisfactory to mine for targets due to the preliminary nature of the database and annotation. Such targets were obtained by designing primers around conserved regions in homologues in public databases of related species including *Ixodes scapularis*, *Dermacentor variabilis* ticks and the *Metaseiulus occidentalis* and *Tetranychus urticae* mites. Primers were designed and employed in anchored-PCR reactions with the pooled *Varroa* synganglia cDNA library as a template. Utilising the cDNA library as the template allowed anchored-PCR reactions to be employed, thus enhancing the chances of success when forward and reverse primers were not totally accurate. Further, using a cDNA library constructed from the synganglia ("brains") permitted greater success when searching for low-abundant neural targets. Resultant PCR products were then sequenced and specific *Varroa* primers designed. BLASTn was carried out against the *Varroa* whole genome shotgun database using the NCBI BLAST servers to obtain accession numbers.

Preparation of dsRNA dsRNA was prepared using a BLOCK-iT RNAi TOPO transcription kit (Invitrogen), according to the manufacturer's instructions. LacZ-dsRNA was prepared and used as a negative control. Briefly, PCR was carried out as described above using adult female *V. destructor* cDNA in conjunction with specific primers, or with control LacZ-plasmid and LacZ specific primers (LacZ-F2, ACCAGAAGCGGTGC-CGGAAA; SEQ ID NO: 28 and LacZ-R2, CCACAGCG-GTGGTTCGGAT; SEQ ID NO: 29).

Products were resolved on an agarose gel, excised and purified using a Qiagen gel extraction kit (Qiagen, Crawley, UK). TOPO-T7 linker was ligated to target and LacZ reactions before a secondary PCR was carried out to gain sense and antisense templates. T7-RNA polymerase was used in transcription reactions with target templates to generate sense and antisense RNA. Finally, RNA strands were annealed and the resultant dsRNA purified and quantified in a micro-spectrophotometer (Nanodrop Technology Ltd). dsRNA was ethanol precipitated and resuspended in DEPC-treated water to a working concentration of 2.5 µg/µl and stored at −80° C.

Protocol of dsRNA Injection and Soaking

Adult female *V. destructor* were removed from capped brood cells along with associated bee larvae. Microinjections were carried out using pulled glass capillary needles in conjunction with a Harvard micro-injector system. Mites were placed on double-sided tape ventral side up, and injected with 20 nl (2.5 µg/µl) of either VdGST-mu1-dsRNA or LacZ-dsRNA in either the soft tissue proximal to the anal region and postcoxal plate, or in the coxa IV region, as indicated in FIG. 7. Needles were left in each mite for 1-2 min to reduce the expulsion of fluid from the wound and withdrawn slowly. Mites were left for 1-2 min to allow the injection site to "seal" then returned to Petri dishes containing 1 bee larvae per 4 mites. Dead or unhealthy looking mites were removed after 1 hour and mortality was monitored over 72 h in LacZ-dsRNA, VdGSTmu1-dsRNA and non-injected mites.

To assess non-invasive techniques for dsRNA delivery, mites were either completely immersed in dsRNA or were exposed to a droplet of dsRNA on their ventral carapace. For soaking experiments, adult mites were removed from capped brood cells and placed in 500 µl microfuge tubes containing 20 µl VdGST-mu1-dsRNA or LacZ-dsRNA (2.5 µg/µl) supplemented with either nothing, 0.9% NaCl, 0.2% Triton-X100 or both. Mites were soaked at 4° C. overnight before being removed, dried and placed in Petri dishes at 27° C., 95% relative humidity with bee larvae. Alternatively, a sample of mites was exposed to dsRNA by attaching them to double-sided tape and placing a 1 µl drop of VdGST-mu1-dsRNA or LacZ-dsRNA (2.5 µl/µg) supplemented with either nothing, 0.9% NaCl, 0.2% Triton-X100 or both on the ventral carapace. Mortality was monitored for 48 h prior to collection and validation of knockdown.

Materials and Methods: Tricatemer Construction

MOA, vATPc and AChE targets were assembled into a single assembly using the Gibson Assembly cloning kit (New England Biolabs). Initial PCR reactions to add overlapping assembly regions were carried out using 25 µl Biomix (Bioline), 23 µl water, 1 µl (1 ng/µl) of PCR4.1 plasmids containing either MOA, AChE or vATPc dsRNA target sequences and 1 µl (2 mM) respective target primers containing target and L4440 overlapping regions (Table 1). The following cycling conditions were used: 1 cycle of 5 min at 94° C., followed by 35 cycles of 1 min at 94° C., 1 min at 58° C. and 45 s at 72° C. Products were resolved on an agarose gel and visualised by UV light to check product size prior to assembly. Reaction was assembled on ice with the following 2 µl MOA, 1.5 µl ATP, 1 µl AChE and 0.5 µl L4440 plasmid, 10 µl Gibson Assembly Master Mix and 5 µl RNAse-free water. Samples were incubated at 50° C. for 60 minutes.

1 µl of GA reaction was transformed into 200 µl ribonuclease-III deficient *E. coli* HT115(DE3), plated onto LB agar containing 12.5 mg/ml tetracycline and 100 mg/ml ampicillin and incubated at 37° C. for 36 hours. Multiple colonies were picked, grown overnight in LB broth containing 100 mg/ml ampicillin at 37° C. Plasmids were purified using Qiagen miniprep columns and sequenced to verify tricatemer insertion (FIG. 13). Glycerol stocks of positive clones were kept at −80° C.

TABLE 1

Gibson assembly primers

GIB-MOA-FWD:
tggatccaccggttcgaacccactagccgaaatggac SEQ ID NO: 30

GIB-MOA-REV:
tcctttcgtgacctccaccttaatagaaacg SEQ ID NO: 31

GIB-vATPc-FWD:
ggaggtcacgaaaggagcattttgtgcttgg SEQ ID NO: 32

GIB-vATPc-REV:
gcaactaattctcgacaaagagacgcagtgc SEQ ID NO: 33

GIB-AChE-FWD:
ttgtcgagaattagttgctcgccacgatatcattg SEQ ID NO: 34

GIB-AChE-REV:
cgtcacgtggctagctggcaagaggacttcccataag SEQ ID NO: 35

Insertion of Targets into L4440 Plasmid and Expression Bacteria

PCR was carried out using 25 µl Biomix (Bioline), 23 µl water, 1 µl (1ng/µl) of PCR4.1 plasmids containing either MOA, AChE, vATPc or the tricatemer dsRNA target sequences and 1 µl (2 mM) respective target primers containing restriction enzyme BglII sites at 5'ends (Table 2). The following cycling conditions were used: 1 cycle of 5 min at 94° C., followed by 35 cycles of 1 min at 94° C., 1 min at 56° C. and 45 s at 72° C. Products were resolved on an agarose gel and visualised by UV light. PCR products were purified using a Qiaquick PCR purification kit. Restriction digests were carried out on the purified PCR products, as well as dsRNA expression plasmid L4440, using BglII restriction enzymes (Promega). Digested PCR and plasmids were ligated using a quick ligation it (New England Biolabs). 1 µl (100 ng) purified L4440 plasmids, containing individual target inserts, were transformed into 200 µl ribonuclease-III deficient *E. coli* HT115(DE3), plated onto LB agar containing 12.5 mg/ml tetracycline and 100 mg/ml ampicillin and incubated at 37° C. for 36 hours. Multiple colonies were selected, grown overnight in LB broth containing 100 mg/ml ampicillin at 37° C. Plasmids were purified using Qiagen miniprep columns and sequenced to verify target insertion. Glycerol stocks of positive clones were kept at −80° C.

Production of dsRNA by *E. coli* HT115 (DE3)

Single colony stocks were grown overnight at 37° C. in 5 ml LB broth containing 12.5 mg/ml tetracycline and 100 mg/ml ampicillin. Each starter culture was diluted 100-fold with 2×YT broth containing 100 mg/ml ampicillin only and incubated at 37° C. until OD600 reached 0.4. T7 RNA polymerase was then induced by the addition of 0.4 mM IPTG and incubated again at 37° C. until OD600 reached 1.0.

Cells were harvested by centrifugation at 6000×g for 5 min and supernatant was discarded prior to dsRNA extraction with TRI-reagent (Life technologies). 1 ml Tri-reagent was used per 10$^7$ bacterial cells. Briefly, cells were disrupted in Tri-reagent by pipetting and allowed to stand for 10 minutes. 0.2 ml chloroform was added per ml Tri-reagent and samples were shaken vigorously for 20 s before incubating at room temperature for a further 10 minutes. Samples were centrifuged at 12000×g for 15 minutes and aqueous layer retained. An additional chloroform extraction was performed and RNA isolated by the addition of 0.5 ml isopropanol per ml Tri-reagent. Precipitated RNA was pelleted by centrifugation at 12000×g for 15 minutes. RNA pellets were washed in 75% ethanol and air dried prior to re-suspension in RNAse-free water. RNA was treated with RNAse A to remove endogenous bacterial ssRNA. To assess the dsRNA quality, Tri-reagent extracted dsRNA was digested with RNAse A or RNase III which specifically digest either ssRNA or dsRNA, respectively. The resultant RNAs were visualised by agarose gel electrophoresis. dsRNA purity and quantity was analysed by both Nanodrop ND-1000 and by comparison with dsRNA markers.

TABLE 2

Target L4440 insertion primers

MOA dsRNA BglII For primer:
atagatctgaacccactagccgaaatg SEQ ID NO: 36

MOA dsRNA BglII Rev primer:
atagatcttgacctccaccttaatagaaac SEQ ID NO: 37 vATPc dsRNA BglII For primer:
atagatctcgaaaggagcattttgtgct SEQ ID NO: 38 vATPc dsRNA BglII1 Rev primer:
atagatctctcgacaaagagacgcagtg SEQ ID NO: 39

ACE dsRNA BglII For primer:
atagatctaattagttgctcgccacgat SEQ ID NO: 40

ACE dsRNA BglII Rev primer:
atagatcttggcaagaggacttcccata SEQ ID NO: 41

EXAMPLES

Example 1: Suppression of GST-Mu1 Expression

Gene knockdown of GST-Mu1 was tested on mites sampled from local beekeepers over a 72 h period. Briefly, for each experiment two groups of eight mites were soaked in 2×saline solution containing 10 ul of 1.25 ug/ul Vd-GSTMu1 dsRNA for 12 h at 4° C., removed and placed on larvae in petri dishes. *Varroa* were kept incubators at 30° C. and 80% RH. Mortality was monitored and samples removed into RNAlater at 24 h intervals.

Analysis of detection PCR gel products using imageJ showed that significant knockdown was achieved after 48 h post-treatment (data not shown). As per initial studies in 2009 with GSTMu1 there was no significant mortality associated with knockdown after soaking compared with mites soaked in control LacZ dsRNA (FIG. 1).

Example 2: Suppression of Neural Target Expression—CHH and PITH

Both crustacean hyperglaecemic hormone (CHH) and prothoracicotropic hormone (PITH) are involved in ionic and energetic metabolism, molting and reproduction.

Homologues were found by BLASTing the *Varroa* genome with known tick and spider mite sequences, as well as from short reads in a synganglion EST library created in 2009. Primer sets were designed for both generation of dsRNA as well as detection of knockdown. BLAST of dsRNA sites vs the *Apis mellifera* genome did not produce highly conserved domains.

Knockdown for both PTTH and CHH was performed by the soaking method detailed above. In groups treated with dsRNA-PTTH, an 85% knockdown of target gene was achieved after 48 h (FIG. 2) compared with levels of the housekeeping gene actin. Interestingly PTTH transcript numbers also showed a decrease in the control LacZ group. This may be due to a natural decline in PTTH after harvest of mites. Levels of PTTH were significantly different between the two groups (P<0.01)

Mortality experiments were carried out on four occasions. In three preliminary assays, mortality levels of up to 60% were observed, albeit with variation believed to be due to factors such as larvae age & quality and fungal growth within the relatively small sample size (<10 mites per assay).

In a larger, more rigorously controlled assay were soaked as above in either dsRNA-PTTH (n=30) or dsRNA-LacZ (n=42). After treatment each treatment group was split into four petri dishes and monitored for mortality and signs of morbidity over 72 h post-treatment. Mites were fed on developing bee larvae (replaced every 24 h) and maintained at 30° C. and 85% RH.

Mites treated with dsRNA-PTTH showed significantly higher mortality compared to controls from 24 h onwards, with 30% survival after 72 h (FIG. 3). Subsequent assays indicate the lethal effect of PITH knockdown may depend on the developmental stage of the *Varroa* mite, with higher lethality if *Varroa* are undergoing metamorphosis or growth.

The level of gene knockdown for CHH was ~60%, with variability in knockdown level observed. Mortality levels for CHH were not significantly different to controls, although a "shaking" phenotype was observed in some mites.

The lethality of PTTH demonstrates that dsRNA is able to penetrate the haemolymph/synganglion barrier, demonstrating the susceptibility of neural targets to dsRNA mediated knockdown.

Example 3: Suppression of Other Targets

Further genes were considered that are either known targets of pesticides or common genes known to be of critical importance to basic physiology.

An initial list of targets was selected and candidates searched for in the available *Varroa* databases. Some targets were discarded at this stage due to a lack of hits in the databases.

Of the list, seven additional targets remained which had sequences in *Varroa* databases that show homology to other arachnid species and with sufficiently long reads for dsRNA delivery (>500 bp). The targets investigated were acetylcholinesterase (AChE), monoamine oxidase (MOA), v-ATPase subunit C (vATPc), chitin synthase (CHS), pyruvate kinase (PyK), GABA receptor (GABA) and α-tubulin (α-TUB).

i) Acetylcholinesterase (AChE)

AChE is the target site for both organophosphate and carbamate insecticides. Both classes of pesticide irreversibly inhibit AChE, fatally disrupting nerve function.

Knockdown was measured initially by direct microinjection of mites with 20 nl of 1 ug/ul dsRNA-AChE and dsRNA-LacZ as control. Mites were injected then maintained on bee larvae for 48 h prior to removal and detection of knockdown by PCR. After 48 h AChE transcripts were 75% lower in treated vs control mites. AChE knockdown was confirmed in mites at various timepoints post-soaking in a separate assay.

For mortality assays mites were soaked in either dsRNA-AChE (n=41) or dsRNA-LacZ (n=44). After treatment each treatment group was split into four petri dishes and monitored for mortality and signs of morbidity over 72 h post-treatment. Mites were fed on developing bee larvae (replaced every 24 h) and maintained at 30° C. and 85% RH.

Mites treated with dsRNA-AChE showed significantly higher mortality compared to controls with ~65% mortality after 72 h (FIG. 4). This experiment was repeated on multiple occasions and similar mortalities were observed.

ii) Monoamine Oxidase (MOA)

MOA catalyzes the degradation of the neurotransmitters dopamine, norepinephrine and serotonin. Thus, reduction in MOA levels may disrupt nervous function.

It is noted that the sequences available on the initial *Varroa* genome deposited in Genbank were not suitable as a basis for developing functional ds RNA constructs. Using a revised sequence, dsRNA was generated and tested as described above. Mortality was ~65% in both soaked and injected individuals after 72 h (FIG. 5).

iii) V-ATPase Subunit C

The V-ATPase enzyme complex consists of a number of subunits and accessory proteins that are all necessary for the enzyme to be active. Subunits H and C were targeted.

dsRNA against subunit H showed knockdown of gene expression, but no lethal effect or observable phenotype (data not shown).

dsRNA that targeted subunit C showed a significant effect. When injected the mortality of mites was ~40% after only 48 hr. At a similar timepoint after soaking the mites the mortality was over 60% (FIG. 6).

iv) Chitin Synthase (CHS)

Chitin synthase is involved in the production of exoskeletal and structural chitin.

Mites assayed with CHS-dsRNA showed increased mortality compared to controls. CHS demonstrated a modest effect with mortality at 45% after 96 hr post-soaking (FIG. 7). This experiment was repeated multiple times and was extremely consistent.

v) Pyruvate Kinase (PyK)

No significant mortality was observed in mites soaked in PyK-dsRNA in small initial experiments. In a larger scale trial, mortality of ~40% was observed after 24 hours (see FIG. 8).

vi) GABA Receptor (GABA)

GABA receptor is vital for regulating neural synapse response. GABA is a target for the Phenylprazole class of insecticide.

The dsRNA construct created for GABA did not cause a significant reduction in mite survival (FIG. 9). The available sequence for GABA in existing genomic databases is restrictive in designing an alternative dsRNA construct and so it is unlikely that a different construct could be trialled until new sequence data becomes available.

vii) α-Tubulin (αTUB)

αTUB-dsRNA did not significantly reduce the amount of target transcript, when assayed by PCR (data not shown).

Example 4: Parallel Suppression of Targets

The assays described above demonstrate that the AChE, MOA and vATPc constructs lead to consistent and significant knockdown of gene expression and mite mortality.

In order to investigate possible cumulative effects of knockdowns so as to increase mortality levels, simultaneous knockdown with vATPc and MOA was performed ("dual knockdown"). Simultaneous knockdown of vATPc, MOA and AChE was also performed ("triple knockdown"). In addition an experiment was carried out to determine if increasing the concentration of total or individual construct dsRNA during the assay would significantly increase mortality.

i) Dual knockdown of vATPc and MOA×2 with same total dsRNA concentration across treatments of 1.25 μg/μl (FIGS. 10 & 11).

ii) Dual knockdown of vATPc and MOA with same individual dsRNA concentrations of 1.25 μg/μl. (FIG. 12)

iii) Triple knockdown of vATPc, MOA and AChE with same individual dsRNA concentration of 1.25 μg/μl (FIG. 13)

Examples: Tricatemer

Example 5: Assessing Tricatemer's Ability to Cause Gene Knockdown of all Three Targets Treatment of Mites:

21 adult *Varroa* mites were removed from capped brood cells, maintained in humidity and temperature controlled environmental boxes in Petri dishes and with bee larvae to assess health. Active mites (18) were randomly divided into two groups and placed in 1.5 ml Eppendorf tubes containing either 40 μl of 1.25 μg/μl dsRNA-GFP control in 0.9% NaCl or 1.25 μg/μl dsRNA-tricatemer in 0.9% saline. Mites were soaked at 4° C. overnight before being removed, dried and placed in Petri dishes. Mites were fed on similar aged developing bee larvae (replaced every 24 h) and maintained at 30° C. and 85% RH. Mites were harvested after 72 h and stored in RNAlater at −80° C. for qPCR analysis.

Measuring Gene Knockdown of dsRNA-Tricatemer Targets Using qPCR:

Mites were sampled 72 hours after treatment with either dsRNA-GFP or dsRNA-tricatemer, placed in 100 μl RNAse-Later and kept at −80° C. until use. Mites removed from RNAse later, washed briefly in cold PBS and homogenised with plastic pestles under 800 μl RNA lysis buffer. Samples were further homogenised by repeatedly passing debris and tissue through 23 gauge needles attached to 1 ml syringes. Mites were then processed according to ZR Tissue & Insect RNA MicroPrep Kit (Zymogen), DNAse-treated with RQ1 (Promega) and eluted in 10 μl RNAse-free water.

RNA concentration of targets was measured by Nanodrop ND-1000 and 0.25 μg RNA for each sample was used in reverse transcription reactions with oligo-dt and Bioscript (Bioline). Resultant cDNA was again measured by Nanodrop-100.

Relative expression qPCR was carried out on an Opticon 2 Engine (Biorad) by Sybr-green detection using reaction mix of 12.5 μl Immolase DNA polymerase (Bioline), 10.5 μl water, 1 μl (1 ng/μl) of template cDNA and 1 μl (2 mM) of the respective target or actin, used as a normalising reference gene. Primers (Table 3) were designed to hybridise to sequences of the cDNA that were external to the region of the dsRNA, thereby amplifying cDNAs derived from *varroa* mRNA but not amplifying the dsRNA itself. The following cycling conditions were used: 1 cycle of 15 min at 94° C., followed by 35 cycles of 45 s at 94° C., 45 s at 56° C. and 45 s at 72° C. Melting curve analysis was carried out to confirm specificity of the reaction products. Ct values were extracted by manual adjustment from sample reaction curves in the linear phase. Knockdown was assessed by the $2^{-\Delta\Delta C_T}$ method [11].

TABLE 3 qPCR primers for determining knockdown of targets

| | | |
|---|---|---|
| MOA Exf1: | ggacgacttcccacacttct | SEQ ID NO: 42 |
| MOA Exr1: | tgccaccccttcatcttcatt | SEQ ID NO: 43 |
| vATPc exf1: | tccttacttgtgcgcaatct | SEQ ID NO: 44 |
| vATPc exr1: | ccggtagtccatagcgaagt | SEQ ID NO: 45 |
| AChE exf1: | aattagttgctcgccacgat | SEQ ID NO: 46 |
| AChE Exr2: | gaaaatagcccctttggcaag | SEQ ID NO: 47 |
| Actin qPCR f1: | catcaccattggtaacgag | SEQ ID NO: 48 |
| Actin qPCR r1: | cgatccagacggaatactt | SEQ ID NO: 49 |

Results:

Compared to mites soaked in GFP dsRNA, the mites soaked 11.25 μg/μl tricatemer dsRNA demonstrated a dramatic decrease (>98%) in their content of amplicons of all three targets, namely MOA, vATPc, and AChE 72 hours after treatment (Table 5). It was noteworthy, that very similar levels of knockdown was observed for all three targets. This indicates that equal absolute amounts or, at least equal efficacy amounts, of dsRNA were generated for each of the gene targets using the 5' and 3' T7-flanked construct within the L440 plasmid. This is most notable for vATPc which sits in the centre of the construct (5'-T7-MOA-vATPc-AChE-T7-3') and might have been expected to have been generated in lower amounts.

TABLE 5

Knockdown for each individual gene target by the dsRNA tricatemer compared with dsRNA-GFP controls

| Gene knockdown vs dsRNA-GFP control | % reduction | Upper limit | Lower limit |
|---|---|---|---|
| vATPc | 98.1 | 99.6 | 92.0 |
| MOA | 99.7 | 99.8 | 99.5 |
| AChE | 98.2 | 98.9 | 97.1 |

Example 5: Assessing Tricatemer's Ability to Kill Mites and its Effectiveness Relative to MOA, AChE and vATPc Singly or in Combination 300 adult *Varroa* mites were removed from capped brood cells and then maintained in Petri dishes within humidity and temperature controlled environmental boxes with bee larvae to assess health. Active mites (270) were randomly assigned into groups of 10 and placed in 1.5 ml eppendorf tubes containing 40 μl 0.9% NaCl and treatments, as detailed in Table 6, giving 3 replicates of 10 mites per treatment. Mites were soaked at 4° C. overnight before being removed, dried and placed in Petri dishes. Mites were fed on similar aged developing bee larvae (replaced every 24 h) and maintained at 30° C. and 85% RH. Mites were monitored for mortality over the subsequent 5 days. Overall treatment effect was assessed by oneway-ANOVA and, if there was significant effect detected, then pairwise comparisons were performed by Fisher's least significant difference method. Statistical analysis was performed using Minitab Vers 16.0.

TABLE 6

Single target vs. tricatemer dsRNA treatments

| Treatment | dsRNA Concentration ($\mu g\ \mu l^{-1}$) |
|---|---|
| 0.9% NaCl control | 0 |
| dsRNA-GFP (1.25 µg/µl) | 1.25 |
| dsRNA-GFP (3.75 µg/µl) | 3.75 |
| dsRNA MOA (1.25 µg/µl) | 1.25 |
| dsRNA vATPc (1.25 µg/µl) | 1.25 |
| dsRNA AChE (1.25 µg/µl) | 1.25 |
| dsRNA MOA + vATPc + AChE (1.25 µg/µl each) | 3.75 |
| dsRNA-tricatemer (1.25 µg/µl) | 1.25 |
| dsRNA-tricatemer (3.75 µg/µl) | 3.75 |

Results

Over the entire 4.5 days post-treatment period, there was a steady increase in the number of mites dying with any of the treatments involving dsRNA designed against any mite gene (FIG. 14). In contrast, little mortality was observed over the 4.5 day period in mites treated with either 1.25 or 3.75 µg/µl dsGFP, indicating that the high mortality of mites treated with mite gene-targeted dsRNA was a specific effect brought about by careful selection of the targets.

At time point 4.5 days post-treatment, a significant effect was detected of treatment upon mite mortality (P<0.0001, F=16.75, df 8/18). All the mite gene-specific dsRNAs caused significantly (P<0.05) more mite mortality than either the saline or the dsGFP (1.25 and 3.75 µg/µl) treatments (FIG. 15).

The tricatemer proved to be particularly effective at both 1.25 and 3.75 µg/µl concentrations. The tricatemer at 3.75 µg/µl resulted in very high mite mortality with low variation. Variation for the tricatemer at 1.25 µg/µl also showed very high mite mortality, but with much higher variation due to a restriction on the number of replicates which could be performed (limited mite numbers). It is anticipated that subsequent replicates will reduce the observed variation. Even without additional replicates, the tricatemer led to significant mite mortality, as described in more detail below.

At 3.75 µg/µl, the tricatemer was significantly more effective than the singly targeted AChE and vATPc dsRNAs (ds RNAs at 1.25 µg/µl; P<0.05); at 3.75 µg/µl the tricatemer was also significantly more effective than the singly targeted MOA dsRNA (ds RNA at 1.25 µg/µl; P<0.07).

Surprisingly, the tricatemer at 3.75 µg/µl was significantly more effective than the 3.75 µg/µl mixture of MOA+AChE+vATPc (P<0.05; FIG. 15). Consistent with the increased potency of the tricatemer versus a mixture of dsRNAs, the 3.75 µg/µl mixture of MOA+AChE+vATPc is not significantly better than the tricatemer at 1.25 µg/µl, despite having a three-fold higher dsRNA concentration. Indeed, the tricatemer at 1.25 µg/µl causes significantly more lethality than the 3.75 µg/µl mixture of MOA+AChE+vATPc (P<0.125).

Comparison to Earlier *V.destructor* dsRNA Studies

As noted in the introduction, previous studies of the transfer of dsRNA from *A.mellifera* hosts to *V.destructor* mites have been reported a decrease in mite population in tested mini-hives of up to 61% [9].

The reported 61% reduction in mite population was recorded at the end of a 60-day trial period during which mites were exposed to a dsRNA mix containing 14 *V.destructor* sequences. The 60-day trial period allowed for two reproductive cycles of *V.destructor*, and the authors of [9] did not directly measure *V.destructor* mite mortality; thus, the 61% figure represents the combined effects of mortality and reduced fecundity over two generations of *V.destructor* mite.

In comparison, the results obtained using the nucleic acid agents of the present invention (see FIG. 14) show that for each of the single gene dsRNA treatments of MOA, AChE, and vATPc a mite mortality of ~52% was recorded. This figure was directly recorded mortality (i.e. mite death) on a single mite generation. Repeated over two generations, this level of mite death would result in a reduction in mite numbers of at least $(1-0.48^2)=77\%$.

For the MOA/AChE/vATPc tricatemer, a mortality of 71% was recorded. Repeated over two generations, this level of mite death would result in a reduction in mite numbers of $(1-0.29^2)=92\%$ (Both this figure and the above figure of 77% considers only direct mite mortality: an even greater reduction would be seen if the likely reduction in mite fecundity was also accounted for).

In addition to increased potency, the ability to achieve high levels of mite mortality using a single, or a small number, of dsRNA sequences (as opposed to 14 different sequences) results in a range of handling and safety advantages. For example, fewer targets means a lower likelihood of "off target" gene silencing (that is, silencing genes other than the intended target(s)), and also reduces production costs and complexity.

REFERENCES

[1] Klein A-, Vaissière B E, Cane J H, Steffan-Dewenter I, Cunningham S A, Kremen C, Tscharntke T: Importance of pollinators in changing landscapes for world crops. Proceedings of the Royal Society B: Biological Sciences 2007, 274:303-313.

[2] van Engelsdorp D, Meixner M D: A historical review of managed honey bee populations in Europe and the United States and the factors that may affect them. J Invertebr Pathol 2010, 103(SUPPL. 1):580-595.

[3] Martin S J: The role of *varroa* and viral pathogens in the collapse of honey bee colonies: A modelling approach. J Appl Ecol 2001, 38:1082-1093.

[4] Winston M L: The honey bee colony: Life history. The hive and the honey bee Hamilton Ill.: Dadant & Sons-Graham JM, 10 1992.

[5] Martin S J: Acaricide (pyrethroid) resistance in *Varroa destructor*. Bee World 2004, 85:67-69.

[6] Whyard S, Singh A D, Wong S: Ingested double-stranded RNAs can act as species-specific insecticides. Insect Biochem Mol Biol 2009, 39:824-832.

[7] Campbell et al.: Gene-knockdown in the honey bee mite *Varroa destructor* by a non-invasive approach: studies on a glutathione S-transferase. Parasites & Vectors 2010 3:73.

[8] US2012/0258646

[9] Garbain Y et al., Bidirectional Transfer of RNAi between Honey Bee and *Varroa destructor: Varroa* Gene Silencing Reduces *Varroa* Population., PLoS Pathogens, December 2012, vol. 8, Iss. 12, e1003035, pages 1-9

[10] Standifer, et al 1977: Supplemental Feeding of Honey Bee Colonies. USDA, Agriculture Information Bulletin No. 413.

[11] Livak K J, Schmittgen T D. Analysis of relative gene expression data using real-time quantitative PCR and the 2(−Delta Delta C(T)) method. Methods. 2001, 25:402-8.

[12] WO2011/045796A1

SEQUENCES: target genes and constructs
GENE               →Acetylcholinesterase (AChE)
Database details   →GenBank accession number ADDG01069748.1
Target sequence    →SEQ ID NO. 1
GGAATTAGTTGCTCGCCACGATATCATTGTGGTAATAATAAACTACCGCCTGTCTGTAATGGGTTTCC

TTTTTTAAACAATACGGAAGCTCCGGGCAATCAGGGACTGCATGATATTCTTTTAGCCGTAAAATTCG

TAAAGGAGAATGCGCGAGCTTTAAATGGAGATCCAGATAAGTTCACCCTATGGGGCCAGTCTGCTGGG

CGTTTGCCGTCGGCTTCCTTATGGGAAGTCCTCTTGCCAAAGGGCTATTTTC

GENE               →Monoamine Oxidase (MOA)
Database details   →GenBank accession number ADDG01053234.1
Target sequence    →SEQ ID NO. 2
ATTCAGGGCAAGCGATACCAGCACCCGGCGGACGACTTCCCACACTTCTGGAACCCACTAGCCGAAAT

GGACGTCAACAATTTTTTCCGAACTTTAGACGATATGGGCAAAGAAATTCCGGCGGAGGCCCCGTGGA

ACGCTCCTCATGCCGAGGAATGGGACCAAATGTTCTTCATTCAGATCAACGTCACCTCGGAGCCCTAC

GAGTCCTCCCTTCTTTGGTTTCTTTGGTACATCAAACAATGTGGTGGCGTTAAGCGAATCGTTTCTAT

TAAGCGAATCGTTTCTATTAAGGGTGGAGGTCAAGAAATGAAGATGAAGGGTGGCATGCAACAGCTCA

GCGAGTCAAT

GENE               →vATPase subunit C (vATPc)
Database details   →GenBank accession number ADDG01035752.1
Target sequence    →SEQ ID NO. 3
GAAAATCTCAAGTCGTACGAGCGCAAGCAAACAGGGTCCTTACTTGTGCGCAATCTGGGAGATCTCGT

ACGAAAGGAGCATTTTGTGCTTGGTTCCGAGTATCTGGTAACGCTCCTTGTCGTTGTCCCCAAAGCGT

TGTTTAAGGCATGGATGGAGAACTATGCAACGCTGACAACTATGGTCGTCCCAAGAACTACGCAGCTT

GTACACGAAGACCAAGATCACGGATTATTCACCGTAACACTTTTCCGCAAAGTTGTCGATGAGTTTAA

GACTCAGGCTCGAGCAAACAAATTCATTGTTCGTGATTTCGAATATAACGAACAAAGCATTCAATCAG

GCAAAGATGAGCGTGGTCGAATGGAAACAGAAAAGAAACGCCAGCTTGCGCTACTCATTCGCTGGTTA

AAGAACAACTTCAGTGAGGCTTTTATCGCTTGGATTCACACTAAGGCACTGCGTCTCTTTGTCGAGTC

GGTACTTCGCTATGGACTACCGGTTAATTTCCAGGGTATGCTACTTCATCCTCAAAAGCGTTGTATGC

GCAGGCTGAGAGACGTGCTGAACCAGTTGTACAGCCATTTGGATAACAGTGCTGCA

GENE               →GABA-receptor alpha subunit (GABA-Rα)
Database details   →GenBank accession number ADDG01060981.1
Target sequence    →SEQ ID NO. 4
CAATATGAACGTTGGCCTATCAGTTATGAACACACTCCCTTCCTATTGCGCCTCCTTTCTATCTTTCT

TTCCTGCTACTTTGACCAATATCTTTGCAGTCGGCTATACAATGAGCGATATCCGCTACAAATGGAAG

GACGGACCCAACTCGATTGGAATCTCGAAAGAAGTCGAGCTCCCTCAATTCAAGGTGCTCGGCCACGT

GCAGAAAATCTCTGAGGTGTCATTGTCGACGGGCAACTATTCACGTCTAATCTGTGAAGTCCGCTTTG

TGAGGTCCATGGGCTACTACCTCATTCAGATCTACATCCCAGCCTCACTCATTGTCGTCATCTCGTGG

GTGTCCTTCTGGCTGCACCGAAACGCAACCCCGGCACGGGTGTCTCTGGGAGTGATGACCGTGCTGAC

AATGACCACCCTAATGTCCAGCACTAACTCCCAATTGCCCAAAATATCCTACGTCAAATCCATCGACG

TTTTCCTAGGAACATGCTTCGTCATGGTAAGAATTCGTCGCCCGAACTTCAAAACGATCACTTCTAAT

CTTCATTCACTCGCCTTTTTTCGAAGGTAGCACAAACGCAAA

GENE               →Chitin Synthase 1 (CHS-1)
Database details   →GenBank accession number ADDG01037469.1
Target sequence    →SEQ ID NO. 5
GGCCATTTCTCGTTGAGAGTGAACGAGTCTGGACGATTCCCGTATCCTGTTTGCTCGTGTCATGTCGC

TGGTGGGAGAACTACGTAGACAAACGATCTCCGTTCGGATTCATCGCTAAACTCGGCGCCATGAAGGA

TGATTTACGTAGGTCGAGGTATTTTCTCTATATTTTCATCGCATCATGGAAGGTTCTGCTGATATTCT

GCTCGATGCTGCTAGTGAATACAATCACTATGGAAAATGTCGTGGATCTGCTTAGATCGTTCGGAAAG

GCTTTCCGTAGCCACAAAATCATGATCGTACAGGTATATCAGCGTGTCTTTGACCATCTGCCGGCCGA

```
TATTCCGACTGCTTCACCCTTAGACGATGACATTTCACTTCTGACGTTCGAGTGGACGCCGCTCATCG

TTGCCCTCATCCAAATCTGTGCCGCGCATCTCTGCTATGTCACATCGAAGTTTGCCTGTAAAATCTGC

ATTCAAGGCTTCAGCTTCGCCTTCCCCATATCCCTCACTATCCCCGTATGCATCTCGTTATTGATTGC

CTCGTGTGGCATACGTTTTGAGGATGTCTGCTTTTTCGAGGGTTGGTTACCGAAATACCTCTTCTGGA

AGTGTCCTCCCGGAGATTTCTTTCAGATCATCGCAGAAATAGATAACGGCAAGTATAGTAGGAAGGGG

GCAAATCCAGTTCAGTTCGA

GENE                →Pyruvate Kinase (PyK)
Database details    →GenBank accession number ADDG01095321.1
Target sequence     →SEQ ID NO. 6
AGCCATTTGTTGCGAAGCGGAAGCCGCGTTTTTCCAGAAAGATGTTTTCCGTCACCTCTCAGAAATAA

CGCCTGTGCCCACTGACTCGACGCATACCGTTGCCATTGCCGCCGTAGCTGCCTCCGTCAAATGTTTG

GCCGGTGCCATTATTGTCGTAACGACCACAGGACGAACGGCTCACCTGGTTGCCCGCTACAAGCCCCG

TTGTCCTATCATTGCAGTGTCGCGCTCGGAGCAGACCGTCCGTCAGGCCCATCTCTACCGCGGCATCC

TGCCGCTTGCCTACGGTGGGGACCGACTACCTGACTGGCCGCAGGACGTCGACAAGCGTATTGAGTTT

GCTATTAGTATTGGCAAGACTCGCGGTTTCCTCAAAAAGAACGACTCAGTGATCGTGGTTACGGGTTG

GCGAAAAGGAGCCGGCGCATCCAACACCCTGCGTGTCGTCGCTGTACCTTAAGGTCGCTGTGCAAAAT

G

GENE                →alpha Tubulin (αTUB)
Database details    →GenBank accession number ADDG01073340.1
Target sequence     →SEQ ID NO. 7
CATTTCGGTATGTACTTTTACCTTTTTCAGGCAGCATTCACCCCGAGCAGCTAATCACTGGAAAGGAA

GATGCGGCCAACAATTATGCCCGTGGCCACTACACGATTGGCAAAGAACTCATTGACCTAGTTCTCGA

TCGTATCCGCAAACTGGCTGACCAGTGCACCGGTCTTCAGGGCTTCCTTATTTTTCACTCATTCGGAG

GAGGAACCGGATCTGGTTTTACCTCTCTCCTCATGGAGCGTTTGTCTGTAGATTATGGCAAGAAATCG

AAGCTAGAATTTGCCGTCTATCCTGCTCCTCAAGTATCGACTGCCGTTGTTGAGCCCTACAACTCGAT

TTTGACTACTCACACAACTCTTGAGCACTCTGACTGCGCCTTCATGGTTGACAACGAGGCTATCTACG

ACATTTGTCGCCGCAATCTCGACATCGAACGTCCAACGTACACCAATCTCAACCGTCTTATCGGCCAA

ATTGTCTCCTCGATTACGGCTTCTCTTCGTTTTGATGGCGCTCTGAACGTAGATCTCACTGAGTTCCA

GACCAACTTGGTGCCATACCCCCGTATCCACTTCCCGCTGGTTACCTACGCGCCTGTCATTTCGGCCG

AGAAGGCCTACCACGAGCAGCACACCGTTGCTGAGATACACCAACGCATGTTTTGAGCCAGCTAATCAG

ATGGTGAAATGCGATCCCCGTCATGGCAAATACATGGCTTGCTGCCTTCTCTATCGTGGCGACGTCGT

GCCAAAGGACGTGAATGCAGCTATTGCTGCAATCAAAACTAAGCGTACTATTCAATTCGTCGATTGGT

GCCCTACTGGTTTCAAGGTCGGTATAAACTACCAGCCGCCAACCGTTGTCCCGGGCGGTGACACTGCC

AAGGTTCCCCGTGCCGTGTGCATGCTGTCCAATACCACCGCTATTGCTGAAGCCTGGGCTCGCCTTGA

CCACAAATTTGATCTGATGTACGCTAAGCGTGCCTTTGTGCACTGGTACGTTGGCGAGGGCATGGAGG

AAGGCGAATTCTCCGAAGCCCGCGAAGATCTAGCCGCCCTCGAAAAGGATTACGAGGAGGTTGGCATC

GACTCTAATGAAGGGGGAGCCGAAGATGACGGCGGCGACGAGTTCTAAGAAAACATCCCAAGAAAGGA

ATTGTGCCACTTCGAAACATTTAAATCGTAATGCTCGGTGTCCACTGAGGTTAAACGGAGATGACAAA

AAATAATTTGAACAGTATTAAAATTATTTGAACCGGAAGAATCCCTTGATGTATTAGGCTTACGGTGG

AACTAGTAAATTTTCCTAATTTGTAGCGCTTGTGTAACAATTATCTGCGTTTTGTTTTCATTTTCAAA

TTATTCGAAGCTTCAATTGAAGAAGCATTACNGGTCATTGAAGTAGTGACATGAACACATGGGATCAC

AATATCGAGAGCTTTCCATTTTAAGTAATCCTAACCTACATGATCAATCACG
```

-continued

GENE →Prothoracicostatic peptide precursor (PTTH)
Database details →GenBank accession number ADDG01000788.1
Target sequence →SEQ ID NO. 8

GCACCGCCAATAACATCAACACGAACTGCAGCGGAGCGATGAGTACCGCGCTGTTGACGGTTGCCCTA

GTCATTGCAGTATGCGCGGTAGGTACTTTCGGAAAGTTTGACGCGGAATCACCGCCCAGCGCACCATC

TCCAGTTGAGTACCCTCCCCAATACTTCGATGCGCCCCTTGAAGCANAGTATGTTCTTCTCAAAAAAG

CTGACGTACCTCCAGCGCCTTGGAACCGCTTGTACGATGATTGGGGTAAAAGGGCTGATAACTGGAAG

AATCTAAATCACCTGTGGGGCAAACGGTCAGCTACACTTCCGACCCGGTGGGACAAACGCCCTCAGCC

GCAGTGGAACGAGCTATCCGGTTATTGGGGAAAGCGTTCGGCCCAGTAA

GENE →Crustacean hyperglycaemic hormone (CHH)
Database details →GenBank accession number ADDG01078386.1
Target sequence →SEQ ID NO. 9

CGCTCGTATAAGAAATTATCGGCATGGCCTTTGCTAGTGGCGCTTGTTGCATCCTCTCAGCTTCGGGG

TGTACGAACGCAAAGTCTTGCCGGATTCGAACCTCTGGGTGGTTTCGCTGGCGCCACGGGCACCATGG

TCCTGCATAAGCGTCTATTTCTCGATGCAGATTGTCGGGGCCCATATGCCCCGCACTTCTACGGCTAC

CTAAACCGAATGCACAACATCTGTAAGGAGTGCGCCGATATGTACCCCGGCATGCGGGATTTCATTAG

CCGCAATTGCACCTCAGAATGCTTCCGTAATCGCGTGTTCCAAGATTGCGTTTCGGCGACGATGCAAC

TCCATCAGCTCGATGAGATCTCCAATATGATCGGTCAGCT

GENE →Glutathione transferase mu1 (GSTμ1)
Database details →GenBank accession number ADDG01001667.1
Target sequence →SEQ ID NO. 10

CGGCGTTACACTACTATTGCCGCTTCTGATTTCGATAAATCAGAATGGGCCCTAGAGAAGGCAAATAA

CAAGTTAAATCTTGCGTTTCCCAACTTACCGTATCTAGTCGATGGCAGTGTCAAACTAAGTCAGAGTC

ATGCTATTATGAGATACTTGGGACGTAAGTTTAATCTAATTGGCACAACCGAGATTGAGCTAGCTCAC

TGTGAGCTCGTTGAACAACAGATTGCTGACTTACGCACAGCCTTCATGAAATTGTGTTACAGTCCAAG

TTTCGAGCGACTTCAGGAGGGTACATGCTCAAAGGCGGACTGCCTTGGAGTTCTCAATGGCGGATTTA

TCGATCGCTTTGCACATATGCTTCAAGAGATTTCGGCATTTCTCGGCGAAAGGAAATGGTTCCTAAAT

GAAAAGTTAACTTACGTTGACTTTCTTGCTTACGAACTTCTTTTTCAAATGTATGTCTGGAATTCATC

AGTATTCAAAAATGTGACGAATCTAACAGATTTTATCACCCGGTTCGAGGCACTTCCGCAAATATCAG

CATACATGAAGACGGACAGCTATATTAAGTGGCCGTTCAACAATATTATGGCATCATATGGTTCCCGA

CONSTRUCT →Tricatemer (MOA, V-ATPase, AChE targets)
Sequence identifier →SEQ ID NO. 11
Notes →L4440 vector is shown in normal text
MOA target sequence is shown in BOLD text
V-ATPase tar-
get sequence is shown in ITALIC text
AChE target sequence is shown in UNDER-
LINED text

GAGCGTGACACCACGATGCCTGTAGCAATGGCAACAACGTTGCGCAAACTATTAACTGGCGAACTACT

TACTCTAGCTTCCCGGCAACAATTAATAGACTGGATGGAGGCGGATAAAGTTGCAGGACCACTTCTGC

GCTCGGCCCTTCCGGCTGGCTGGTTTATTGCTGATAAATCTGGAGCCGGTGAGCGTGGGTCTCGCGGT

ATCATTGCAGCACTGGGGCCAGATGGTAAGCCCTCCCGTATCGTAGTTATCTACACGACGGGGAGTCA

GGCAACTATGGATGAACGAAATAGACAGATCGCTGAGATAGGTGCCTCACTGATTAAGCATTGGTAAC

TGTCAGACCAAGTTTACTCATATATACTTTAGATTGATTTAAAACTTCATTTTTAATTTAAAAGGATC

TAGGTGAAGATCCTTTTTGATAATCTCATGACCAAAATCCCTTAACGTGAGTTTTCGTTCCACTGAGC

GTCAGACCCCGTAGAAAAGATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAAGAGCTACCAACTCTTTTT

CCGAAGGTAACTGGCTTCAGCAGAGCGCAGATACCAAATACTGTCCTTCTAGTGTAGCCGTAGTTAGG

CCACCACTTCAAGAACTCTGTAGCACCGCCTACATACCTCGCTCTGCTAATCCTGTTACCAGTGGCTG

-continued

CTGCCAGTGGCGATAAGTCGTGTCTTACCGGGTTGGACTCAAGACGATAGTTACCGGATAAGGCGCAG

CGGTCGGGCTGAACGGGGGGTTCGTGCACACAGCCCAGCTTGGAGCGAACGACCTACACCGAACTGAG

ATACCTACAGCGTGAGCTATGAGAAAGCGCCACGCTTCCCGAAGGGAGAAAGGCGGACAGGTATCCGG

TAAGCGGCAGGGTCGGAACAGGAGAGCGCACGAGGGAGCTTCCAGGGGGAAACGCCTGGTATCTTTAT

AGTCCTGTCGGGTTTCGCCACCTCTGACTTGAGCGTCGATTTTTGTGATGCTCGTCAGGGGGCGGAG

CCTATGGAAAAACGCCAGCAACGCGGCCTTTTTACGGTTCCTGGCCTTTTGCTGGCCTTTTGCTCACA

TGTTCTTTCCTGCGTTATCCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGCAACCTGGCTTATCGAAAT

TAATACGACTCACTATAGGGAGACCGGCAGATCTGATATCATCGATGAATTCGAGCTCCACCGCGGTG

GCGGCCGCTCTAGAACTAGTGGATCCACCGGTTCGAACCCACTAGCCGAAATGGACGTCAACAATTTT

TTCCGAACTTTAGACGATATGGGCAAAGAAATTCCGGCGGAGGCCCCGTGGAACGCTCCTCATGCCGA

GGAATGGGACCAAATGACATGTAGGGAGTTCGTCAACAAAACGTGTTGGACCAAAGAGGGTCGCGAAT

TCGCAGAGTTCTTCATTCAGATCAACGTCACCTCGGAGCCCTACGAGTCCTCCCTTCTTTGGTTTCTT

TGGTACATCAAACAATGTGGTGGCGTTAAGCGAATCGTTTCTATTAAGCGAATCGTTTCTATTAAGGG

TGGAGGTCA_CGAAAGGAGCATTTTGTGCTTGGTTCCGAGTATCTGGTAACGCTCCTTGTCGTTGTCCC_

_CAAAGCGTTGTTTAAGGCATGGATGGAGAACTATGCAACGCTGACAACTATGGTCGTCCCAAGAACTA_

_CGCAGCTTGTACACGAAGACCAAGATCACGGATTATTCACCGTAACACTTTTCCGCAAAGTTGTCGAT_

_GAGTTTAAGACTCAGGCTCGAGCAAACAAATTCATTGTTCGTGATTTCGAATATAACGAACAAAGCAT_

_TCAATCAGGCAAAGATGAGCGTGGTCGAATGGAAACAGAAAAGAAACGCCAGCTTGCGCTACTCATTC_

_GCTGGTTAAAGAACAACTTCAGTGAGGCTTTTATCGCTTGGATTCACACTAAGGCACTGCGTCTCTTT_

_GTCGAG_<u>AATTAGTTGCTCGCCACGATATCATTGTGGTAATAATAAACTACCGCCTGTCTGTAATGGGT</u>

<u>TTCCTTTTTTAAACAATACGGAAGCTCCGGGCAATCAGGGACTGCATGATATTCTTTTAGCCGTAAAA</u>

<u>TTCGTAAAGGAGAATGCGCGAGCTTTAAATGGAGATCCAGATAAGTTCACCCTATGGGCCAGTCTGC</u>

<u>TGGGCGTTTGCCGTCGGCTTCCTTATGGGAAGTCCTCTTGCCA</u>GCTAGCCACGTGACGCGTGGATCCC

CCGGGCTGCAGGAATTCGATATCAAGCTTATCGATACCGTCGACCTCGAGGGGGGGCCCGGTACCCAA

TTCGCCCTATAGTGAGTCGTATTACGCGCGCTCACTGGCCGTCGTTTTACAACGTCGTGACTGGGAAA

ACCCTGGCGTTACCCAACTTAATCGCCTTGCAGCACATCCCCCTTTCGCCAGCTGGCGTAATAGCGAA

GAGGCCCGCACCGATCGCCCTTCCCAACAGTTGCGCAGCCTGAATGGCGAATGGGACGCGCCCTGTAG

CGGCGCATTAAGCGCGGCGGGTGTGGTGGTTACGCGCAGCGTGACCGCTACACTTGCCAGCGCCCTAG

CGCCCGCTCCTTTCGCTTTCTTCCCTTCCTTTCTCGCCACGTTCGCCGGCTTTCCCCGTCAAGCTCTA

AATCGGGGGCTCCCTTTAGGGTTCCGATTTAGTGCTTTACGGCACCTCGACCCCAAAAAACTTGATTA

GGGTGATGGTTCACGTAGTGGGCCATCGCCCTGATAGACGGTTTTTCGCCCTTTGACGTTGGAGTCCA

CGTTCTTTAATAGTGGACTCTTGTTCCAAACTGGAACAACACTCAACCCTATCTCGGTCTATTCTTTT

GATTTATAAGGGATTTTGCCGATTTCGGCCTATTGGTTAAAAAATGAGCTGATTTAACAAAAATTTAA

CGCGAATTTTAACAAAATATTAACGCTTACAATTTAGGTGGCACTTTTCGGGGAAATGTGCGCGGAAC

CCCTATTTGTTTATTTTTCTAAATACATTCAAATATGTATCCGCTCATGAGACAATAACCCTGATAAA

TGCTTCAATAATATTGAAAAAGGAAGAGTATGAGTATTCAACATTTCCGTGTCGCCCTTATTCCCTTT

TTTGCGGCATTTTGCCTTCCTGTTTTTGCTCACCCAGAAACGCTGGTGAAAGTAAAAGATGCTGAAGA

TCAGTTGGGTGCACGAGTGGGTTACATCGAACTGGATCTCAACAGCGGTAAGATCCTTGAGAGTTTTC

GCCCCGAAGAACGTTTTCCAATGATGAGCACTTTTAAAGTTCTGCTATGTGGCGCGGTATTATCCCGT

ATTGACGCCGGGCAAGAGCAACTCGGTCGCCGCATACACTATTCTCAGAATGACTTGGTTGAGTACTC

-continued

ACCAGTCACAGAAAAGCATCTTACGGATGGCATGACAGTAAGAGAATTATGCAGTGCTGCCATAACCA

TGAGTGATAACACTGCGGCCAACTTACTTCTGACAACGATCGGAGGACCGAAGGAGCTAACCGCTTTT

TTGCACAACATGGGGATCATGTAACTCGCCTTGATCGTTGGGAACCGGAGCTGAATGAAGCCATACC

AAACGAC

Sequence identifier →SEQ ID NO. 12
Notes              →MOA target sequence
GAACCCACTAGCCGAAATGGACGTCAACAATTTTTTCCGAACTTTAGACGATATGGGCAAAGAAATTC

CGGCGGAGGCCCCGTGGAACGCTCCTCATGCCGAGGAATGGGACCAAATGACATGTAGGGAGTTCGTC

AACAAAACGTGTTGGACCAAAGAGGGTCGCGAATTCGCAGAGTTCTTCATTCAGATCAACGTCACCTC

GGAGCCCTACGAGTCCTCCCTTCTTTGGTTTCTTTGGTACATCAAACAATGTGGTGGCGTTAAGCGAA

TCGTTTCTATTAAGCGAATCGTTTCTATTAAGGGTGGAGGTCA

Sequence identifier →SEQ ID NO. 13
Notes              →V-ATPase target sequence
CGAAAGGAGCATTTTGTGCTTGGTTCCGAGTATCTGGTAACGCTCCTTGTCGTTGTCCCCAAAGCGTT

GTTTAAGGCATGGATGGAGAACTATGCAACGCTGACAACTATGGTCGTCCCAAGAACTACGCAGCTTG

TACACGAAGACCAAGATCACGGATTATTCACCGTAACACTTTTCCGCAAAGTTGTCGATGAGTTTAAG

ACTCAGGCTCGAGCAAACAAATTCATTGTTCGTGATTTCGAATATAACGAACAAAGCATTCAATCAGG

CAAAGATGAGCGTGGTCGAATGGAAACAGAAAAGAAACGCCAGCTTGCGCTACTCATTCGCTGGTTAA

AGAACAACTTCAGTGAGGCTTTTATCGCTTGGATTCACACTAAGGCACTGCGTCTCTTTGTCGAG

Sequence identifier →SEQ ID NO. 14
Notes              →AChE target sequence
AATTAGTTGCTCGCCACGATATCATTGTGGTAATAATAAACTACCGCCTGTCTGTAATGGGTTTCCTT

TTTTAAACAATACGGAAGCTCCGGGCAATCAGGGACTGCATGATATTCTTTTAGCCGTAAAATTCGTA

AAGGAGAATGCGCGAGCTTTAAATGGAGATCCAGATAAGTTCACCCTATGGGGCCAGTCTGCTGGGCG

TTTGCCGTCGGCTTCCTTATGGGAAGTCCTCTTGCCA

---

The invention claimed is:

1. An isolated nucleic acid agent comprising a nucleic acid sequence that is capable of downregulating the expression of a gene of the *Varroa destructor* mite, wherein the gene encodes Monoamine Oxidase (MOA; GenBank accession number ADDG01053234.1) (SEQ ID NO: 15), Acetylcholinesterase (AChE; GenBank accession number ADDG01069748.1) (SEQ ID NO: 16), vATPase subunit C (vATPc; GenBank accession number ADDG01035752.1) SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), Prothoracicostatic peptide precursor (PTTH; GenBank accession number ADDG01000788.1) (SEQ ID NO: 22), or Crustacean hyperglycaemic hormone (CHH; GenBank accession number ADDG01078386.1) (SEQ ID NO: 23), wherein the nucleic acid agent is selected from the group consisting of a double-stranded RNA (dsRNA), an antisense RNA, a ribozyme, and an isolated nucleic acid concatemer.

2. The isolated nucleic acid agent according claim 1, wherein the agent is less than 500 bases long.

3. The isolated nucleic acid agent according to claim 1, wherein the isolated nucleic comprises a sequence having 100% sequence identity to at least 21 contiguous nucleotides encoded by SEQ ID NO.2, SEQ ID NO.1, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

4. The isolated nucleic acid agent according to claim 3, wherein the isolated nucleic comprises a sequence having 100% sequence identity to at least 50 contiguous nucleotides encoded by SEQ ID NO.2, SEQ ID NO.1, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

5. The isolated nucleic acid agent according to claim 4, wherein the isolated nucleic comprises a sequence having 100% sequence identity to at least 200 contiguous nucleotides encoded by SEQ ID NO.2, SEQ ID NO.1, SEQ ID NO.3, SEQ ID NO.4, SEQ ID NO.5, SEQ ID NO.6, SEQ ID NO.7, SEQ ID NO.8, SEQ ID NO.9, or SEQ ID NO.10.

6. A nucleic acid composition comprising at least two isolated nucleic acid agents according to claim 1, wherein the at least two isolated nucleic acid agents are capable of downregulating the expression of at least two different genes from *Varroa destructor*.

7. A nucleic acid composition comprising three isolated nucleic acid agents according to claim 1, wherein the at three nucleic acid agents are capable of downregulating the expression of three different genes from *Varroa destructor*.

8. The nucleic acid composition according to claim 6, wherein the two genes are selected from the genes encoding for Monoamine Oxidase (MOA; GenBank accession number ADDG01053234.1) (SEQ ID NO: 15), Acetylcholinesterase (AChE; GenBank accession number ADDG01069748.1) (SEQ ID NO: 16), and vATPase subunit C (vATPc; GenBank accession number ADDG01035752.1) SEQ ID NO: 17).

9. The nucleic acid composition according to claim 6, wherein the two isolated nucleic acid agents are selected from: (i) a nucleic acid agent comprising a sequence having 100% sequence identity to at least 21 contiguous nucleotides encoded by SEQ ID NO.2; (ii) a nucleic acid agent comprising a sequence having 100% sequence identity to at least 21 contiguous nucleotides encoded by SEQ ID NO.1; and (iii) a nucleic acid agent comprising a sequence having 100% sequence identity to at least 21 contiguous nucleotides encoded by SEQ ID NO.3.

10. An isolated nucleic acid concatemer comprising at least a first nucleic acid sequence and a second nucleic acid sequence;
wherein the first nucleic acid sequence is capable of down-regulating the expression of a first gene of the *Varroa destructor* mite, and the second nucleic acid sequence is capable of down-regulating the expression of a second gene of the *Varroa destructor* mite; wherein the concatemer optionally further comprises a third nucleic acid sequence, wherein the third nucleic acid sequence is capable of down-regulating the expression of a third gene of the *Varroa destructor* mite.

11. The isolated nucleic acid concatemer according to claim 10, wherein the first, second, and/or third gene, if present, is selected from the group consisting of the genes which encode:
Monoamine Oxidase (MOA; GenBank accession number ADDG01053234.1) (SEQ ID NO: 15), Acetylcholinesterase (AChE; GenBank accession number ADDG01069748.1) (SEQ ID NO: 16), vATPase subunit C (vATPc; GenBank accession number ADDG01035752.1) (SEQ ID NO: 17), GABA-receptor alpha subunit (GABA-Rα; GenBank accession number ADDG01060981.1) (SEQ ID NO: 18), Chitin Synthase 1 (CHS-1; GenBank accession number ADDG01037469.1) (SEQ ID NO: 19), Pyruvate Kinase (PyK; GenBank accession number ADDG01095321.1) (SEQ ID NO: 20), alpha Tubulin (αTUB; GenBank accession number ADDG01073340.1) (SEQ ID NO: 21), Prothoracicostatic peptide precursor (PTTH; GenBank accession number ADDG01000788.1) (SEQ ID NO: 22), Crustacean hyperglycaemic hormone (CHH; GenBank accession number ADDG01078386.1) (SEQ ID NO: 23), and Glutathione transferase mu1 (GSTµ1; GenBank accession number ADDG01001667.1) (SEQ ID NO: 24).

12. The isolated nucleic acid concatemer according to claim 10, wherein the first, second, and/or third gene, if present, is selected from the group consisting of the genes which encode:
Monoamine Oxidase (MOA; GenBank accession number ADDG01053234.1) (SEQ ID NO: 15), Acetylcholinesterase (AChE; GenBank accession number ADDG01069748.1) (SEQ ID NO: 16), and vATPase subunit C (vATPc; GenBank accession number ADDG01035752.1) (SEQ ID NO: 17).

13. The isolated nucleic acid concatemer according to claim 10, wherein the first, second, and/or third nucleic acid sequence, if present, comprise a nucleic acid sequence that has 100% sequence identity to at least 21 contiguous nucleotides encoded by a sequence selected from the group consisting of SEQ ID NO.2, SEQ ID NO.1, SEQ ID NO.3, SEQ ID NO.4, SEQ ID NO.5, SEQ ID NO.6, SEQ ID NO.7, SEQ ID NO.8, SEQ ID NO.9, and SEQ ID NO.10.

14. The isolated nucleic acid concatemer according to claim 10, wherein the first, second, and/or third nucleic acid sequence, if present, comprise a nucleic acid sequence that has 100% sequence identity to at least 21 contiguous nucleotides encoded by a sequence selected from the group consisting of SEQ ID NO.2, SEQ ID NO.1, and SEQ ID NO.3.

15. An isolated nucleic acid concatemer according to claim 10, wherein the concatemer comprises the sequences of SEQ ID NOs: 12, 13 and 14.

16. The isolated nucleic acid concatemer according to claim 10, wherein the total length of the concatemer agent is less than 1000 bases.

17. The isolated nucleic acid agent according to claim 1, wherein mRNA levels of the targeted genes in treated *Varroa destructor* mites are 98% lower 72 hours after exposure to the agent, composition or concatemer.

18. The isolated nucleic acid agent according to claim 1, wherein the agent, composition or concatemer causes greater than 60% mite mortality, as measured 108 hours after a 12 hour soaking of the mite in a 1.25 µg/µl solution of the nucleic acid agent, composition, or concatemer.

19. The isolated nucleic acid agent according to claim 1, wherein the nucleic acid agent or concatemer is a dsRNA, antisense RNA, or a ribozyme.

20. The isolated nucleic acid agent according to claim 19 wherein the dsRNA is an siRNA, shRNA or miRNA.

21. A nucleic acid construct encoding the isolated nucleic acid agent according to claim 1.

22. The nucleic acid construct of claim 21 having the sequence set out in SEQ ID NO.11.

23. A composition for feeding to bees comprising an isolated nucleic acid agent according to claim 1.

24. A method of:
(i) treating or preventing a *Varroa destructor* mite infestation of a beehive;
(ii) treating or preventing a viral infection in a honeybee; or
(iii) treating or preventing Colony Collapse Disorder (CCD) in honeybees;
the method comprising administering to a member of the beehive an isolated nucleic acid agent according to claim 1.

* * * * *

SEQUENCE LISTING

<160> NUMBER OF SEQ ID NOS: 49

<210> SEQ ID NO 1
<211> LENGTH: 256
<212> TYPE: DNA
<213> ORGANISM: Varroa destructor

<400> SEQUENCE: 1
ggaattagtt gctcgccacg atatcattgt ggtaataata aactaccgcc tgtctgtaat    60
gggtttcctt ttttaaacaa tacgaagct ccgggcaatc agggactgca tgatattctt   120
ttagccgtaa aattcgtaaa ggagaatgcg cgagctttaa atggagatcc agataagttc   180
accctatggg gccagtctgc tgggcgtttg ccgtcggctt ccttatggga agtcctcttg   240
ccaaagggct attttc                                                  256

<210> SEQ ID NO 2
<211> LENGTH: 350
<212> TYPE: DNA
<213> ORGANISM: Varroa destructor

<400> SEQUENCE: 2
attcagggca agcgatacca gcacccggcg gacgacttcc cacacttctg gaacccacta    60
gccgaaatgg acgtcaacaa tttttttccga actttagacg atatgggcaa agaaattccg   120

```
gcggaggccc cgtggaacgc tcctcatgcc gaggaatggg accaaatgtt cttcattcag    180
atcaacgtca cctcggagcc ctacgagtcc tcccttcttt ggtttctttg gtacatcaaa    240
caatgtggtg gcgttaagcg aatcgtttct attaagcgaa tcgtttctat taagggtgga    300
ggtcaagaaa tgaagatgaa gggtggcatg caacagctca gcgagtcaat              350
```

<210> SEQ ID NO 3
<211> LENGTH: 600
<212> TYPE: DNA
<213> ORGANISM: Varroa destructor

<400> SEQUENCE: 3

```
gaaaatctca gtcgtacga gcgcaagcaa acagggtcct tacttgtgcg caatctggga     60
gatctcgtac gaaaggagca ttttgtgctt ggttccgagt atctggtaac gctccttgtc   120
gttgtcccca agcgttgtt taaggcatgg atggagaact atgcaacgct gacaactatg    180
gtcgtcccaa gaactacgca gcttgtacac gaagaccaag atcacggatt attcaccgta   240 acactttcc gcaaagttgt cgatgagttt aagactcagg ctcgagcaaa caaattcatt    300
gttcgtgatt tcgaatataa cgaacaaagc attcaatcag gcaaagatga gcgtggtcga   360
atggaaacag aaaagaaacg ccagcttgcg ctactcattc gctggtaaa gaacaacttc    420 agtgaggctt ttatcgcttg gattcacact aaggcactgc gtctctttgt cgagtcggta   480
cttcgctatg gactaccggt taatttccag ggtatgctac ttcatcctca aaagcgttgt   540
atgcgcaggc tgagagacgt gctgaaccag ttgtacagcc atttggataa cagtgctgca   600
```

<210> SEQ ID NO 4
<211> LENGTH: 586
<212> TYPE: DNA
<213> ORGANISM: Varroa destructor

<400> SEQUENCE: 4

```
caatatgaac gttggcctat cagttatgaa cacactccct tcctattgcg cctcctttct     60
atctttcttt cctgctactt tgaccaatat ctttgcagtc ggctatacaa tgagcgatat    120
ccgctacaaa tggaaggacg acccaactc gattggaatc tcgaaagaag tcgagctccc    180
tcaattcaag gtgctcggcc acgtgcagaa aatctctgag gtgtcattgt cgacgggcaa    240
ctattcacgt ctaatctgtg aagtccgctt tgtgaggtcc atgggctact acctcattca    300
gatctacatc ccagcctcac tcattgtcgt catctcgtgg gtgtccttct ggctgcaccg    360
aaacgcaacc ccggcacggg tgtctctggg agtgatgacc gtgctgacaa tgaccaccct    420
aatgtccagc actaactccc aattgcccaa aatatcctac gtcaaatcca tcgacgtttt    480
cctaggaaca tgcttcgtca tggtaagaat tcgtcgcccg aacttcaaaa cgatcacttc    540
taatcttcat tcactcgcct tttttcgaag gtagcacaaa cgcaaa                 586
```

<210> SEQ ID NO 5
<211> LENGTH: 700
<212> TYPE: DNA
<213> ORGANISM: Varroa destructor

<400> SEQUENCE: 5

```
ggccatttct cgttgagagt gaacgagtct ggacgattcc cgtatcctgt ttgctcgtgt     60
catgtcgctg gtgggagaac tacgtagaca acgatctcc gttcggattc atcgctaaac    120
tcggcgccat gaaggatgat ttacgtaggt cgaggtattt tctctatatt ttcatcgcat    180
```

```
catggaaggt tctgctgata ttctgctcga tgctgctagt gaatacaatc actatggaaa    240
atgtcgtgga tctgcttaga tcgttcggaa aggctttccg tagccacaaa atcatgatcg    300
tacaggtata tcagcgtgtc tttgaccatc tgccggccga tattccgact gcttcaccct    360
tagacgatga catttcactt ctgacgttcg agtggacgcc gctcatcgtt gccctcatcc    420
aaatctgtgc cgcgcatctc tgctatgtca catcgaagtt tgcctgtaaa atctgcattc    480
aaggcttcag cttcgccttc cccatatccc tcactatccc cgtatgcatc tcgttattga    540
ttgcctcgtg tggcatacgt tttgaggatg tctgcttttt cgagggttgg ttaccgaaat    600
acctcttctg gaagtgtcct cccggagatt tctttcagat catcgcagaa atagataacg    660
gcaagtatag taggaagggg gcaaatccag ttcagttcga                          700
```

<210> SEQ ID NO 6
<211> LENGTH: 477
<212> TYPE: DNA
<213> ORGANISM: Varroa destructor

<400> SEQUENCE: 6

```
agccatttgt tgcgaagcgg aagccgcgtt tttccagaaa gatgttttcc gtcacctctc     60
agaaataacg cctgtgccca ctgactcgac gcataccgtt gccattgccg ccgtagctgc    120
ctccgtcaaa tgtttggccg gtgccattat tgtcgtaacg accacaggac gaacggctca    180
cctggttgcc cgctacaagc cccgttgtcc tatcattgca gtgtcgcgct cggagcagac    240
cgtccgtcag gcccatctct accgcggcat cctgccgctt gcctacggtg gggaccgact    300
acctgactgg ccgcaggacg tcgacaagcg tattgagttt gctattagta ttggcaagac    360
tcgcggtttc ctcaaaaaga cgactcagt gatcgtggtt acgggttggc gaaaaggagc    420
cggcgcatcc aacaccctgc gtgtcgtcgc tgtaccttaa ggtcgctgtg caaaatg       477
```

<210> SEQ ID NO 7
<211> LENGTH: 1480
<212> TYPE: DNA
<213> ORGANISM: Varroa destructor
<220> FEATURE:
<221> NAME/KEY: misc_feature
<222> LOCATION: (1392)..(1392)
<223> OTHER INFORMATION: n is a, c, g, or t

<400> SEQUENCE: 7

```
catttcggta tgtactttta ccttttttcag gcagcattca ccccgagcag ctaatcactg     60
gaaaggaaga tgcggccaac aattatgccc gtggccacta cacgattggc aaagaactca    120
ttgacctagt tctcgatcgt atccgcaaac tggctgacca gtgcaccggt cttcagggct    180
tccttatttt tcactcattc ggaggaggaa ccggatctgg ttttacctct ctcctcatgg    240
agcgtttgtc tgtagattat ggcaagaaat cgaagctaga atttgccgtc tatcctgctc    300
ctcaagtatc gactgccgtt gttgagccct acaactcgat tttgactact cacacaactc    360
ttgagcactc tgactgcgcc ttcatggttg acaacgagga tatctacgac atttgtcgcc    420
gcaatctcga catcgaacgt ccaacgtaca ccaatctcaa ccgtcttatc ggccaaattg    480
tctcctcgat tacggcttct cttcgttttg atggcgctct gaacgtagat ctcactgagt    540
tccagaccaa cttggtgcca tacccccgta tccacttccc gctggttacc tacgcgcctg    600
tcatttcggc cgagaaggcc taccacgagc agcacaccgt tgctgagatc accaacgcat    660
gttttgagcc agctaatcag atggtgaaat gcgatcccg tcatggcaaa tacatggctt    720
gctgccttct ctatcgtggc gacgtcgtgc caaaggacgt gaatgcagct attgctgcaa    780
```

```
tcaaaactaa gcgtactatt caattcgtcg attggtgccc tactggtttc aaggtcggta      840
taaactacca gccgccaacc gttgtcccgg gcggtgacac tgccaaggtt ccccgtgccg      900
tgtgcatgct gtccaatacc accgctattg ctgaagcctg gctcgccctt gaccacaaat      960
ttgatctgat gtacgctaag cgtgcctttg tgcactggta cgttggcgag gcatggagg      1020 aaggcgaatt ctccgaagcc cgcgaagatc tagccgccct cgaaaaggat tacgaggagg      1080
ttggcatcga ctctaatgaa gggggagccg aagatgacgg cggcgacgag ttctaagaaa      1140
acatcccaag aaaggaattg tgccacttca gaacatttaa atcgtaatgc tcggtgtcca      1200
ctgaggttaa acgagatgca caaaaaataa tttgaacagt attaaaatta tttgaaccgg      1260
aagaatccct tgatgtatta ggcttacggt ggaactagta aattttccta atttgtagcg      1320
cttgtgtaac aattatctgc gttttgtttt cattttcaaa ttattcgaag cttcaattga      1380
agaagcatta cnggtcattg aagtagtgac atgaacacat gggatcacaa tatcgagagc      1440
tttccatttt aagtaatcct aacctacatg atcaatcacg                             1480

<210> SEQ ID NO 8
<211> LENGTH: 389
<212> TYPE: DNA
<213> ORGANISM: Varroa destructor
<220> FEATURE:
<221> NAME/KEY: misc_feature
<222> LOCATION: (183)..(183)
<223> OTHER INFORMATION: n is a, c, g, or t

<400> SEQUENCE: 8
gcaccgccaa taacatcaac acgaactgca gcggagcgat gagtaccgcg ctgttgacgg       60
ttgccctagt cattgcagta tgcgcggtag gtactttcgg aaagtttgac gcggaatcac      120
cgcccagcgc accatctcca gttgagtacc ctccccaata cttcgatgcg ccccttgaag      180
canagtatgt tcttctcaaa aaagctgacg tacctccagc gccttggaac cgcttgtacg      240
atgattgggg taaaagggct gataactgga agaatctaaa tcacctgtgg ggcaaacggt      300
cagctacact tccgacccgg tgggacaaac gccctcagcc gcagtggaac gagctatccg      360
gttattgggg aaagcgttcg gcccagtaa                                         389

<210> SEQ ID NO 9
<211> LENGTH: 380
<212> TYPE: DNA
<213> ORGANISM: Varroa destructor

<400> SEQUENCE: 9
cgctcgtata agaaattatc ggcatggcct ttgctagtgg cgcttgttgc atcctctcag       60
cttcggggtg tacgaacgca aagtcttgcc ggattcgaac ctctgggtgg tttcgctggc      120
gccacgggca ccatggtcct gcataagcgt ctatttctcg atgcagattg tcgggcccca      180
tatgccccgc acttctacgg ctacctaaac cgaatgcaca acatctgtaa ggagtgcgcc      240
gatatgtacc ccggcatgcg ggatttcatt agccgcaatt gcacctcaga atgcttccgt      300
aatcgcgtgt tccaagattg cgtttcggcg acgatgcaac tccatcagct cgatgagatc      360
tccaatatga tcggtcagct                                                   380

<210> SEQ ID NO 10
<211> LENGTH: 612
<212> TYPE: DNA
<213> ORGANISM: Varroa destructor
```

<400> SEQUENCE: 10

| | | | | | |
|---|---|---|---|---|---|
| cggcgttaca | ctactattgc | cgcttctgat | ttcgataaat | cagaatgggc | cctagagaag | 60 |
| gcaaataaca | agttaaatct | tgcgtttccc | aacttaccgt | atcagtcga | tggcagtgtc | 120 |
| aaactaagtc | agagtcatgc | tattatgaga | tacttgggac | gtaagtttaa | tctaattggc | 180 |
| acaaccgaga | ttgagctagc | tcactgtgag | ctcgttgaac | aacagattgc | tgacttacgc | 240 |
| acagccttca | tgaaattgtg | ttacagtcca | agtttcgagc | gacttcagga | gggtacatgc | 300 |
| tcaaaggcgg | actgccttgg | agttctcaat | ggcggattta | tcgatcgctt | tgcacatatg | 360 |
| cttcaagaga | tttcggcatt | tctcggcgaa | aggaaatggt | tcctaaatga | aaagttaact | 420 |
| tacgttgact | tcttgctta | cgaacttctt | tttcaaatgt | atgtctggaa | ttcatcagta | 480 |
| ttcaaaaatg | tgacgaatct | aacagatttt | atcacccggt | tcgaggcact | tccgcaaata | 540 |
| tcagcataca | tgaagacgga | cagctatatt | aagtggccgt | tcaacaatat | tatggcatca | 600 |
| tatggttccc | ga | | | | | 612 |

<210> SEQ ID NO 11
<211> LENGTH: 3747
<212> TYPE: DNA
<213> ORGANISM: Artificial sequence
<220> FEATURE:
<223> OTHER INFORMATION: Synthetic construct

<400> SEQUENCE: 11

| | | | | | |
|---|---|---|---|---|---|
| gagcgtgaca | ccacgatgcc | tgtagcaatg | caacaacgt | tgcgcaaact | attaactggc | 60 |
| gaactactta | ctctagcttc | ccggcaacaa | ttaatagact | ggatggaggc | ggataaagtt | 120 |
| gcaggaccac | ttctgcgctc | ggcccttccg | gctggctggt | ttattgctga | taaatctgga | 180 |
| gccggtgagc | gtgggtctcg | cggtatcatt | gcagcactgg | ggccagatgg | taagccctcc | 240 |
| cgtatcgtag | ttatctacac | gacggggagt | caggcaacta | tggatgaacg | aaatagacag | 300 |
| atcgctgaga | taggtgcctc | actgattaag | cattggtaac | tgtcagacca | agtttactca | 360 |
| tatatacttt | agattgattt | aaaacttcat | ttttaattta | aaaggatcta | ggtgaagatc | 420 |
| cttttgata | atctcatgac | caaaatccct | taacgtgagt | tttcgttcca | ctgagcgtca | 480 |
| gaccccgtag | aaaagatcaa | aggatcttct | tgagatcctt | ttttctgcg | cgtaatctgc | 540 |
| tgcttgcaaa | caaaaaaacc | accgctacca | gcggtggttt | gtttgccgga | tcaagagcta | 600 |
| ccaactcttt | ttccgaaggt | aactggcttc | agcagagcgc | agataccaaa | tactgtcctt | 660 |
| ctagtgtagc | cgtagttagg | ccaccacttc | aagaactctg | tagcaccgcc | tacatacctc | 720 |
| gctctgctaa | tcctgttacc | agtggctgct | gccagtggcg | ataagtcgtg | tcttaccggg | 780 |
| ttggactcaa | gacgatagtt | accggataag | gcgcagcggt | cgggctgaac | ggggggttcg | 840 |
| tgcacacagc | ccagcttgga | gcgaacgacc | tacaccgaac | tgagatacct | acagcgtgag | 900 |
| ctatgagaaa | gcgccacgct | tcccgaaggg | agaaaggcgg | acaggtatcc | ggtaagcggc | 960 |
| agggtcggaa | caggagagcg | cacgagggag | cttccagggg | gaaacgcctg | gtatctttat | 1020 |
| agtcctgtcg | ggtttcgcca | cctctgactt | gagcgtcgat | ttttgtgatg | ctcgtcaggg | 1080 |
| gggcggagcc | tatggaaaaa | cgccagcaac | gcggcctttt | tacggttcct | ggccttttgc | 1140 |
| tggccttttg | ctcacatgtt | ctttcctgcg | ttatcccctg | attctgtgga | taaccgtatt | 1200 |
| accgcctttg | agtgagctga | taccgctcgc | cgcagccgaa | cgaccgagcg | cagcgagtca | 1260 |
| gtgagcgagg | aagcaacctg | gcttatcgaa | attaatacga | ctcactatag | ggagaccggc | 1320 |
| agatctgata | tcatcgatga | attcgagctc | caccgcggtg | gcggccgctc | tagaactagt | 1380 |

```
ggatccaccg gttcgaaccc actagccgaa atggacgtca acaattttt ccgaacttta      1440
gacgatatgg gcaaagaaat tccggcgag gccccgtgga acgctcctca tgccgaggaa      1500
tgggaccaaa tgacatgtag ggagttcgtc aacaaaacgt gttggaccaa agagggtcgc     1560
gaattcgcag agttcttcat tcagatcaac gtcacctcgg agcccctacga gtcctccctt    1620
ctttggtttc tttggtacat caaacaatgt ggtggcgtta agcgaatcgt ttctattaag     1680
cgaatcgttt ctattaaggg tggaggtcac gaaaggagca ttttgtgctt ggttccgagt     1740
atctggtaac gctccttgtc gttgtcccca aagcgttgtt taaggcatgg atggagaact     1800
atgcaacgct gacaactatg gtcgtcccaa gaactacgca gcttgtacac gaagaccaag     1860
atcacggatt attcaccgta acactttcc gcaaagttgt cgatgagttt aagactcagg      1920
ctcgagcaaa caaattcatt gttcgtgatt tcgaatataa cgaacaaagc attcaatcag     1980
gcaaagatga gcgtggtcga atggaaacag aaaagaaacg ccagcttgcg ctactcattc     2040
gctggtaaaa gaacaacttc agtgaggctt ttatcgcttg gattcacact aaggcactgc     2100
gtctctttgt cgagaattag ttgctcgcca cgatatcatt gtggtaataa taaactaccg     2160
cctgtctgta atgggtttcc tttttttaaac aatacgaag ctccgggcaa tcagggactg     2220
catgatattc ttttagccgt aaaattcgta aggagaatg cgcgagcttt aaatggagat      2280
ccagataagt tcaccctatg gggccagtct gctgggcgtt tgccgtcggc ttccttatgg     2340
gaagtcctct tgccagctag ccacgtgacg cgtggatccc ccgggctgca ggaattcgat    2400
atcaagctta tcgataccgt cgacctcgag ggggggcccg gtacccaatt cgccctatag    2460
tgagtcgtat tacgcgcgct cactggccgt cgttttacaa cgtcgtgact gggaaaaccc    2520
tggcgttacc caacttaatc gccttgcagc acatccccct ttcgccagct ggcgtaatag    2580
cgaagaggcc cgcaccgatc gcccttccca acagttgcgc agcctgaatg gcgaatggga    2640
cgcgccctgt agcggcgcat taagcgcggc gggtgtggtg gttacgcgca gcgtgaccgc    2700
tacacttgcc agcgccctag cgcccgctcc tttcgctttc ttcccttcct ttctcgccac    2760
gttcgccggc tttccccgtc aagctctaaa tcggggctc cctttagggt tccgatttag     2820
tgctttacgg cacctcgacc ccaaaaaact tgattagggt gatggttcac gtagtgggcc    2880
atcgccctga tagacggttt ttcgcccttt gacgttggag tccacgttct ttaatagtgg    2940
actcttgttc caaactggaa caacactcaa ccctatctcg gtctattctt tgatttata     3000
agggattttg ccgatttcgg cctattggtt aaaaaatgag ctgatttaac aaaaatttaa    3060
cgcgaatttt aacaaaatat taacgcttac aatttaggtg cacttttcg gggaaatgtg     3120
cgcggaaccc ctatttgttt attttctaa atacattcaa atatgtatcc gctcatgaga     3180
caataaccct gataaatgct tcaataatat tgaaaagga agagtatgag tattcaacat    3240
ttccgtgtcg cccttattcc cttttttgcg gcattttgcc ttcctgtttt tgctcaccca    3300
gaaacgctgg tgaaagtaaa agatgctgaa gatcagttgg gtgcacgagt gggttacatc    3360
gaactggatc tcaacagcgg taagatcctt gagagttttc gccccgaaga acgttttcca    3420
atgatgagca cttttaaagt tctgctatgt ggcgcggtat tatcccgtat tgacgccggg    3480
caagagcaac tcggtcgccg catacactat tctcagaatg acttggttga gtactcacca    3540
gtcacagaaa agcatcttac ggatggcatg acagtaagag aattatgcag tgctgccata    3600
accatgagtg ataacactgc ggccaactta cttctgacaa cgatcggagg accgaaggag    3660
ctaaccgctt ttttgcacaa catgggggat catgtaactc gccttgatcg ttgggaaccg    3720
```

```
gagctgaatg aagccatacc aaacgac                                        3747
```

<210> SEQ ID NO 12
<211> LENGTH: 315
<212> TYPE: DNA
<213> ORGANISM: Varroa destructor

<400> SEQUENCE: 12

```
gaacccacta gccgaaatgg acgtcaacaa ttttttccga actttagacg atatgggcaa     60
agaaattccg gcggaggccc cgtggaacgc tcctcatgcc gaggaatggg accaaatgac    120
atgtagggag ttcgtcaaca aaacgtgttg gaccaaagag ggtcgcgaat tcgcagagtt    180
cttcattcag atcaacgtca cctcggagcc ctacgagtcc tcccttcttt ggtttctttg    240
gtacatcaaa caatgtggtg gcgttaagcg aatcgtttct attaagcgaa tcgtttctat    300
taagggtgga ggtca                                                    315
```

<210> SEQ ID NO 13
<211> LENGTH: 405
<212> TYPE: DNA
<213> ORGANISM: Varroa destructor

<400> SEQUENCE: 13

```
cgaaaggagc attttgtgct tggttccgag tatctggtaa cgctccttgt cgttgtcccc     60
aaagcgttgt ttaaggcatg gatggagaac tatgcaacgc tgacaactat ggtcgtccca    120
agaactacgc agcttgtaca cgaagaccaa gatcacggat tattcaccgt aacactttc     180
cgcaaagttg tcgatgagtt taagactcag gctcgagcaa acaaattcat tgttcgtgat    240
ttcgaatata cgaacaaag cattcaatca ggcaaagatg agcgtggtcg aatggaaaca    300
gaaaagaaac gccagcttgc gctactcatt cgctggttaa agaacaactt cagtgaggct    360
tttatcgctt ggattcacac taaggcactg cgtctctttg tcgag                   405
```

<210> SEQ ID NO 14
<211> LENGTH: 241
<212> TYPE: DNA
<213> ORGANISM: Varroa destructor

<400> SEQUENCE: 14

```
aattagttgc tcgccacgat atcattgtgg taataataaa ctaccgcctg tctgtaatgg     60
gtttcctttt ttaaacaata cggaagctcc gggcaatcag ggactgcatg atattctttt    120
agccgtaaaa ttcgtaaagg agaatgcgcg agctttaaat ggagatccag ataagttcac    180
cctatggggc cagtctgctg ggcgtttgcc gtcggcttcc ttatgggaag tcctcttgcc    240
a                                                                   241
```

<210> SEQ ID NO 15
<211> LENGTH: 1909
<212> TYPE: DNA
<213> ORGANISM: Varroa destructor

<400> SEQUENCE: 15

```
acggatgtga gccatcgggc ttcgtgtcgt ctatcgtata gataacggga gcatacgtct     60
ctgatggagt agcgccgatg gcgccgctat agccgaggtc acgccaccaa gcatcctata    120
aatatttaac cataacccag gaacgattca tatgtaagca agcgtcacgt tgctgggtac    180
aattcgtgta cagtttgaaa cttgaaaaca ggattagttt attgttcata catattaaat    240
atttcggatt ttactttcga tactagacta gttgagcacg agctaacccc ttccagcacg    300
```

```
aagcgaggca ccagcggatt ctggcattac cccacctgcc cctacgttta tactactact      360
actactactg cacgattacg ggaactcgtt tttaatatcg gtatgtactg ttaccttata      420
ataaacctgg agtttccata cagatcccat cggcatacgt tgcgctagtt gagtacggag      480
cggaccaaga ctaggagaga atgaattttt catctgcatt ggaggagctg ttgccagaat      540
aatatgtgac ccctcaaatt tttcaccgtt tatacagcgt acgacgacgc cgccgttcga      600
gtgttccact gatactacag catgatttaa tttaactcgt tctaaaatat catagagaac      660
ataaaagtgg caacaataga actagatgtt gtatatcaca cctgacaaaa aaaggttcaa      720
aactctttct atttagagca ttgttgctta accataatga gttgatacgt atcttgccgt      780
aacgatcaat ttgttagtga ttcggttaaa atggtcgttt tagtaggaca aaaggtacct      840
atgtacgcgg ttcatatttg ctagggtaaa cgttggaaga atacttgatc gaatagacca      900
gccacagacc tccaagtgat ttgaacattg actcgctgag ctgttgcatg ccacccttca      960
tcttcatttc ttgacctcca ccctgaaatc aagttaaatc gtaaccgttt actcccgcac     1020
caagtgatta cagtttactg ttgaaaacgt acgtaatttt gtactacgtg tgcttcgtat     1080
aagcaaattg ggaggatcgc ataagtttcg agtaagcttt tttcgacata gactattttc     1140
acggactagc agtaccttaa tagaaacgat tcgcttaacg ccaccacatt gtttgatgta     1200
ccaaagaaac caaagaaggg aggactcgta gggctccgag gtgacgttga tctgaatgaa     1260
gaactctgcg aattcgcgac cctctctaga acgagagaac agaatgagaa caagtcaaat     1320
gtagcacaac ttcgaatgtt gtggcacatg ggcgtgctaa ctgcagttgc taacgatatt     1380
taaatttatt gtttgcttca tttccgggaa ataagaacta ccagtctcga aatgatcatg     1440
tctagattcg aaactggcaa aacggccagt ctcgctaagg tccgtgcaga cgtaaaatgt     1500
attcgtattt ggacgtgtta aactctcatc ctgattatcc tgcttgccca atactaactt     1560
ggtccaacac gttttgttga cgaactccct acatgtcatt tggtcccatt cctcggcatg     1620
aggagcgttc cacggggcct ccgccggaat ttctttgccc atatcgtcta aagttcggaa     1680
aaaattgttg acgtccattt cggctagtgg gttccagaag tgtgggaagt cgtccgccgg     1740
gtgctggtat cgcttgccct gaatgagcaa tagagttcaa ggtctactct gaagctaaac     1800
tgtttgttcc actgctctac atatttgcta aaaagcgttt tataaaaatc gtttacgcca     1860
cttaccattt tagactactt aagccggtgc tgacctggct agagttttt                 1909
```

<210> SEQ ID NO 16
<211> LENGTH: 1549
<212> TYPE: DNA
<213> ORGANISM: Varroa destructor

<400> SEQUENCE: 16

```
ttcgggccaa tagcttgtca aaggtcgctg gttccacacg tagcggtaaa cctagaaaga       60
agagtatgga tcctcagtgt aatcgtatta gttcctactc tgttatacta cttttatagt      120
ttcactatct gtagaagttt ggccattcga aaagccacgg cagtacgcac aggatttctt      180
gcattcacaa cgttatttt atgctttaaa gttctacgtt aaattttaa agtcgttcgg       240 gctttggcac ataggtttcg atatatcgtt gggtttaaaa tgtcttgcga tattgatgac      300
tggtcaatga caatttatta cagtcatgaa gccttctgcc gcgtccaacc aatgtaattt      360 atcccaatt tacgcacggc gacatacaac gttcgaagca tcaaaatttg gataaacaaa       420
tgattgttct tatgcgcatt acgtagttta cttagtatcg catatcatac aagctgatag      480
```

-continued

```
caatgctgta caacgcaagt tatgttgtta ttataagttg tccgagttac actggtaata      540
atgataaaca gaaatatgt accttgacac ccctattggc gaggaaagcg gaataaagat       600
cggttgggca ctcgaaaata agatctccaa atagacgccc catggcagag cgtagattat      660
ggccaacctg caacgtctgc gggatgtatg caatcgaact gtctcgtacg agctccacag      720
gtaaattgag aatgaccttc ataacgattc gcgcaagatc gatgtaatca tcagccgaag      780
acgtatcgtt gaattgaaaa cgttccagta ttccttcgat gaacaagcct ccctcgttgc      840
ttacggtact tgtaaacacc tccttaatgt cgtcgttgag gggcaccttt gactgatcag      900
tagggaatgg aaaatcgggc aggaggttgt cgataccata ttgtggttgg aaggttatcg      960
tataatgctc tcctaaacct cggttcactg cgtcaaacag cgtcttagcg tcaacattct     1020
ttatacaacg gccaatatct tctagttggt cttcaggttt tcgactcgaa tcgatgcaat     1080
tgacaacact ggcggcactt actgcgccgt ttatgctatt catcgaaaaa gatggagcag     1140
cactgacagg tgtaccgctc tgaagtatca ctcgcgaaaa tagcccttg gcaagaggac      1200 ttcccataag gaagccgacg gcaaacgccc agcagactgg ccccataggg tgaacttatc     1260
tggatctcca tttaaagctc gcgcattctc ctttacgaat tttacggcta aaagaatatc     1320
atgcagtccc tgattgcccg gagcttccgt attgtttaaa aaaggaaacc cattacagac     1380
aggcggtagt ttattattac cacaatgata tcgtggcgag caactaattc ctcaggatcg     1440
tagaggaata agccgttgaa gcctccaagg aagcttcctc catatacgta cacaacgaca     1500
ggggcatctg ttacacccctt cggcctatag atgttcacgt gtaagcaat               1549

<210> SEQ ID NO 17
<211> LENGTH: 2440
<212> TYPE: DNA
<213> ORGANISM: Varroa destructor

<400> SEQUENCE: 17
gcaaacatgt cagcacacat gggaaaacta aatgaagcaa taggtcgaga acagcttgca       60
acaaactaca aattcaatct gcctgatctt aaggtaactc gaatagaacg aaaaatatca      120
gtattcaccc ggcctgacct tagtaaacat attaaacgta ggttcaaagc ttgcatgaat      180
ttggaacaac tgtgtaatat tgtttcaaga agtatgattt gttcagtgca attttctgct      240
tcattagaaa tgcgagcttt aatttgtata ttaatacggt gggcaactaa atacaattag      300
tatacctagg gtgtctaata atgaaaatga atgtgcaata tcagccctgt cagcaattta      360
aaggttgttc atatgctaag tcagctaaat ggtaattaaa aaaattataa tatttgcaac      420
gttagaaaag ggctcattaa ttttaattct gttaactgta attcaatcat aattattcgc      480
acccttgata tctatttaac tccaaaaatg gccaataaag tatcaataaa tagaccacac      540
tttgggcatt gcttgttatt ggctctgtaa tactaatgtt aatttactcg atggttattt      600
ggtttaaagg ctatatcgct ttcgtatttc gagcacggtt cagatatatg catgtcaagc      660
atttctgatg taaacattct atgcgatctg aatgaaaaat aagacgaggt tcttttcaca      720
gaagcttgtt tcgttcacgt ataacaacca ttcgtttcat attgtttact ttttcaaagg      780
tgggaactct ggatcaacta gtttcgctat ctgatgaact gcagcgtgtg gaccagttta      840
cagagcaagt tactcgtaag attgcaaatt accttgcaga tgtgttcgag gatcagagag      900
ataaattcag cgaaaatctc aaggtaaaaa attgtttcga ttgttctcag atccttaacc      960
agttggaatg ttttaatata gtagagtgaa aaacctggtt tgtcagaaat acaaaatatc     1020
caaaatattt agttattact tccatacgtg tcattaagct cgatggacac caagagaata     1080
```

```
ttgccttgcg tagcataaat attgttctat aaaacaatgt tttcagccca ttactacaat    1140
ttattattcg tttcacaaga tttagacctc catttattcc atcagttagg tcctgttcag    1200
acaagcctca ctttatgaat tttcgtgttt gctgttgcgc aatctctacg atcggaatac    1260
cgatctaggc gaacggaacg gatttggtgc tttacgtcaa acggttcagc tgggacgtgg    1320
caaaatatcc aaagcatcag ccgctgcccg cgctaaccca aatgattaac aagcagttgg    1380
ggatgatcga cagtgagctc aagacacgct cggtcaggga tacgcacgc taaaatccaa     1440 tattcagtcg tacgagcgca agcaaacagg gtccttactt gtgcgcaatc tgggagatct    1500
cgtacgaaag gagcattttg tgcttggttc cgagtatctg gtaacgctcc ttgtcgttgt    1560
ccccaaagcg ttgtttaagg catggatgga gaactatgca acgctgacaa ctatggtcgt    1620
cccaagaact acgcagcttg tacacgaaga ccaagatcac ggattattca ccgtaacact    1680
tttccgcaaa gttgtcgatg agtttaagac tcaggctcga gcaaacaaat tcattgttcg    1740
tgatttcgaa tataacgaac aaagcattca atcaggcaaa gatgagcgtg gtcgaatgga    1800
aacagaaaag aaacgccagc ttgcgctact cattcgctgg ttaaagaaca acttcagtga    1860
ggcttttatc gcttggattc acactaaggc actgcgtctc tttgtcgagt cggtacttcg    1920
ctatggacta ccggttaatt tccaggtaaa ctaatcacct tcatatactt tccgaaaggg    1980
ctctgactcg atggcatgat tcgatttatc aattcatatt gacttcacgg aaaataagta    2040 gttatttat ttatggtata ttcacattta atttgctatt atttacgcat acaaatatta      2100
tattatatat ttttaaatat attattatat aaaatcaaat atatagggag ataatatttg    2160
tggtctgcag ggttaactat ttcttcttat agggcttaga acttcggaga ttttacagt     2220 acaattatgt acataaacta catgggaact ttacagtacg tttgcatatg taatcttatt    2280
ttcatctatt acttaataat ttatttatta ctaatctcgt ttcaacttta tttttattgc    2340
agggtatgct acttcatcct caaaagcgtt gtatgcgcag gctgagagac gtgctgaacc    2400
agttgtacag ccatttggat aacagtgctg cagtagggcc                          2440
```

<210> SEQ ID NO 18
<211> LENGTH: 1726
<212> TYPE: DNA
<213> ORGANISM: Varroa destructor

<400> SEQUENCE: 18

```
tgggtgccag atacgttttt gctaatgaga agactgccta ttttcatgtg gctacgacgc     60
ccaacacttt ccttcgaatt agctcggaag acaggtctca cagaagtatt cggtgcgtac    120
ctctcacatg gacgcattat taattagtag aaattaccta gacatgaaaa ctttgaatcg    180
acattctaac aaatgtttta agtttttacgt ccaagtctgg tgctattgct atcaagaact    240
gttactttag atggctgata atccgttcta acgcaaaatg aaatacgttt ggagtaggtt    300
tcgaacctga cgacctcgt cagatattcc tgtctttagc agcaaaaaca ttagttatat     360
tggcctgata cgaggcttaa tttcaggccg tgctgtctgc atactttaca tgagaaaaaa    420
atcgctgtac gcgtaacgcc aatgcgctaa agcgagcatt gacaacatac ataattagga    480
gaactatttg ggaagttgac aaaaacaaag tctactgcga gttcgtcacg aatcttgcaa    540
tagatcgtat cgaaagtacc tacaaatcgt taatggaagc aaataagcca agcatcgatg    600
cccttgacgc gatacgaccg ccataatttc tttgacgtct ttacacgtag gcagtattat    660
aggttatgtt tgtgtttctt ctgccttcat accccgtttc agattgacag tgacagccag    720
```

| | |
|---|---|
| ctgtccgatg gatcttcgat tcttcccaat ggacagacaa tcatgtacta ttgaagtcga | 780 |
| aagttgtgag tatctatatc aaacactttt tgttacacag atagttcttt tggtatgcct | 840 |
| cattaacgtt aacacatata acaaggaagt attatttag caaactagaa attaccctaa | 900 |
| ttatgaagac agtatgcgaa tagcaaatga taatatttgta tgctaaatac gcaggacgca | 960 |
| atcaacggac ggtgttgagc aatctggtct atttaatttc tctgttgcta tcttatacca | 1020 |
| ttgttgttag gggcatgata gtcaaaacca tgcatatgtt attcaataat gatcgccact | 1080 |
| caaaaatac aatatgaacg ttggcctatc agttatgaac acactcccctt cctattgcgc | 1140 |
| ctcctttcta tctttctttc ctgctacttt gaccaatatc tttgcagtcg gctatacaat | 1200 |
| gagcgatatc cgctacaaat ggaaggacgg acccaactcg attggaatct cgaaagaagt | 1260 |
| cgagctccct caattcaagg tgctcggcca cgtgcagaaa atctctgagg tgtcattgtc | 1320 |
| gacgggcaac tattcacgtc taatctgtga agtccgcttt gtgaggtcca tgggctacta | 1380 |
| cctcattcag atctacatcc cagcctcact cattgtcgtc atctcgtggg tgtccttctg | 1440 |
| gctgcaccga aacgcaaccc cggcacgggt gtctctggga gtgatgaccg tgctgacaat | 1500 |
| gaccacccta atgtccagca ctaactccca attgcccaaa atatcctacg tcaaatccat | 1560 |
| cgacgttttc ctaggaacat gcttcgtcat ggtaagaatt cgtcgcccga acttcaaaac | 1620 |
| gatcacttct aatcttcatt cactcgcctt ttttcgaagg tagcacaaac gcaaatactg | 1680 |
| catctgtgct caacgaatca gtgggagatc ttgaatgagg cttaac | 1726 |

<210> SEQ ID NO 19
<211> LENGTH: 2378
<212> TYPE: DNA
<213> ORGANISM: Varroa destructor

<400> SEQUENCE: 19

| | |
|---|---|
| aaagccgggt aaattaggct gaaaatttg taaaatttaa atcgataaca attgtgaaaa | 60 |
| ggcacacctc tctgccggtt tcccagtttc aaaattttg aataagaatc caacgaataa | 120 |
| tatgtcaagc atgggcctaa aggcattttt tggaattagt atcccgagtg caataaata | 180 |
| gccatcgcca cgtcaactga tagtatcgaa acttctgtcc aagaaagccc ttcttgtca | 240 |
| tctttctact tactataaat tataagttaa acgtaattca taaaattta tttgttttga | 300 |
| cgtattataa cctttaaaca attttatttta gtttttattt attaagtatt tataaaaatt | 360 |
| gatactaaga ataacaaata ttgccccttgc aggttttttt aatggagtcg ttccatgtgt | 420 |
| tcggattagt tctcctcgta tttgtagttc tcccggagtt ggatgtcgtc aaagcggcta | 480 |
| tgctcaccaa ctgcatgtgc ttcttaccgg catttttggt atgctatcac actatcaggg | 540 |
| tgaagagaaa cgagcgttaa gaactctgct ggattttcct gtttgtgcgc ccaagcgatg | 600 |
| ggttttgtcg tgtggccatt tctcgttgag agtgaacgag tctggacgat tcccgtatcc | 660 |
| tgtttgctcg tgtcatgtcg ctggtgggag aactacgtag acaaacgatc tccgttcgga | 720 |
| ttcatcgcta aactcggcgc catgaaggat gatttacgta ggtcgaggta ttttctctat | 780 |
| attttcatcg catcatggaa ggttctgctg atattctgct cgatgctgct agtgaataca | 840 |
| atcactatgg aaaatgtcgt ggatctgctt agatcgttcg gaaaggcttt ccgtagccac | 900 |
| aaaatcatga tcgtacaggt aagtcgttag caatgtggca cattgatgtt tgtaaacgtc | 960 |
| catatatgca tacgggttaa aaaaaacaac tttaagagac cgcgtcgtgg tttcctactt | 1020 |
| agctgaggtc acgtcacgtc gcgaaactag tttttaccgt ttagcacaac gaacagatcc | 1080 |
| gcgttatcat tttacatatt attaccattt aactattaat atatttattt gttttcacc | 1140 |

```
gatgtttcat gcatattttg aactttgatc ttcaacgtac attggtgccg gacgcaattc   1200
ttcgtgggtc cgtcttgccc tcgttttcgt aaaagtaaga cgagctttt  atgtttatct   1260 taatttcaca ggtatatcag cgtgtctttg accatctgcc ggccgatatt ccgactgctt   1320
caccgttaga cgatgacatt tcacttctga cgttcgagtg gacgccgctc atcgttgccc   1380
tcatccaaat ctgtgccgcg catctctgct atgtcacatc gaagtttgcc tgtaaaatct   1440
gcattcaagg cttcagcttc gccttcccca tatccctcac tatccccgta tgcatctcgt   1500
tattgattgc ctcgtgtggc atacgttttg aggatgtctg cttttcgag  ggttggttac    1560 cgaaatacct cttctggaag tgtcctcccg gagatttctt tcaggtttgt tatctgataa   1620
agttgcgagt cgtagttaag gagcacaaaa gtagggaatt gcaattatat caaaacaaca   1680
ttagtaggca aggtgaaagc actagtatga actttgaat  gtaaatagat catcgcagaa   1740
atagataacg gcaagtatag taggaagggg gcaaatccag ttcagttcga acccaatgtc   1800
tcccaaaaag gaccccccatt cctgctgcga ttatagacca agatatccac tactgttcag   1860
gccattcgta tcatttagtt tccactcaaa acaatcctct aagtccctgt cagggaagtc   1920
aggctttacc taactaaagc ccaatcagct tttctacaag ggtggggcaa gcggtcccaa   1980
gacagtgtga cgatctatcg tcggactagc atagccaagg tagacctttc ctcgaatagc   2040
agtagaaaaa aatgaagctc aacagcatcg atgagtctcg ccgttaatat caactctata   2100
aataagatcc acgtcaacaa gagtaacgct gcgtctcgct actgctgcca tacgttttc    2160 atccaggccg gatggtttag aactgtgtgt gtgtgtgggt ggccgaactc cctttcgatt   2220
gagtaggtat ggttagttgg tcagccaatt cttcgtaggt ctttacagcg aagccgcttc   2280
tcccgtcaaa gctccacacg gcaaagagga acctttcgtt actgttagcc accggttttc   2340
ctgacccatt cactgttctg tgggactgtt ttaacctt                           2378

<210> SEQ ID NO 20
<211> LENGTH: 1135
<212> TYPE: DNA
<213> ORGANISM: Varroa destructor

<400> SEQUENCE: 20
ctccatgttc attgattttt tcatttttg  tcttgattct catccggtct ctgtctaaac     60
gtcctgcaac tcgctacttg acactcatcg aaataagtaa tcatcacgtg aggatcttcc    120
ttaatcgcgt ttgttctgca tgcgctgata ttaactgatg taacttactc tacagattat    180
gtatgaacta accctaatag tgaaacagaa catggaagcg acctgctgta atcacaggaa    240
caacaaattc gataatggca atgatgatct gcattcacaa cgagctcctg taagacgcgg    300
tcatcgggac agagcgttag tttgctacaa aagattcttc ttatagatac ttactctagt    360
gtgtccgctt cggtcgccct attactaatt ataatactta accgtcctca atacccgttg    420
atcgtgttgg cgtgaatgcg acagcacagt tactcccaat attttacatt ttagtatttt    480
attggtgttg tttcttactt ttcgattagg tcattatttt cccttggttt tacaggtttc    540
tccttcgctt tctctctctg tccagtgatt ttcttttccc gtctcgctgt taactgaacg    600
ttgattttcg tgggtctttg tgctcctttt gcttctgctg gaggttgttt ttctccatt    660 tgcacagcga ccttaaggta cagcgacgac acgcagggtg ttggatgcgc cggctccttt    720
tcgccaaccc gtaaccacga tcactgagtc gttcttttg  aggaaaccgc gagtcttgcc    780
aatactaata gcaaactcaa tacgcttgtc gacgtcctgc ggccagtcag gtagtcggtc    840
```

```
cccaccgtag gcaagcggca ggatgccgcg gtagagatgg gcctgacgga cggtctgctc      900
cgagcgcgac actgcaatga taggacaacg gggcttgtag cgggcaacca ggtgagccgt      960
tcgtcctgtg gtcgttacga caataatggc accggccaaa catttgacgg aggcagctac     1020
ggcggcaatg gcaacggtat gcgtcgagtc agtgggcaca ggcgttattt ctgagaggtg     1080
acggaaaaca tctttctgga aaacgcggc ttccgcttcg aacaaatgg ctgac            1135
```

<210> SEQ ID NO 21
<211> LENGTH: 1480
<212> TYPE: DNA
<213> ORGANISM: Varroa destructor
<220> FEATURE:
<221> NAME/KEY: misc_feature
<222> LOCATION: (1392)..(1392)
<223> OTHER INFORMATION: n is a, c, g, or t

<400> SEQUENCE: 21

```
catttcggta tgtacttta cctttttcag gcagcattca ccccgagcag ctaatcactg       60
gaaaggaaga tgcggccaac aattatgccc gtggccacta cacgattggc aaagaactca     120
ttgacctagt tctcgatcgt atccgcaaac tggctgacca gtgcaccggt cttcagggct     180
tccttatttt tcactcattc ggaggaggaa ccggatctgg ttttacctct ctcctcatgg     240
agcgtttgtc tgtagattat ggcaagaaat cgaagctaga atttgccgtc tatcctgctc     300
ctcaagtatc gactgccgtt gttgagccct acaactcgat tttgactact cacacaactc     360
ttgagcactc tgactgcgcc ttcatggttg acaacgaggc tatctacgac atttgtcgcc     420
gcaatctcga catcgaacgt ccaacgtaca ccaatctcaa ccgtcttatc ggccaaattg     480
tctcctcgat tacggcttct cttcgttttg atggcgctct gaacgtagat ctcactgagt     540
tccagaccaa cttggtgcca taccccgta tccacttccc gctggttacc tacgcgcctg     600
tcatttcggc cgagaaggcc taccacgagc agcacaccgt tgctgagatc accaacgcat     660
gttttgagcc agctaatcag atggtgaaat gcgatcccg tcatggcaaa tacatggctt     720
gctgccttct ctatcgtggc gacgtcgtgc caaaggacgt gaatgcagct attgctgcaa     780
tcaaaactaa gcgtactatt caattcgtcg attggtgccc tactggtttc aaggtcggta     840
taaactacca gccgccaacc gttgtcccgg gcggtgacac tgccaaggtt ccccgtgccg     900
tgtgcatgct gtccaatacc accgctattg ctgaagcctg ggctcgcctt gaccacaaat     960
ttgatctgat gtacgctaag cgtgcctttg tgcactggta cgttggcgag ggcatggagg    1020
aaggcgaatt ctccgaagcc cgcgaagatc tagccgccct cgaaaaggat tacgaggagg    1080
ttggcatcga ctcaatgaa gggggagccg aagatgacgg cggcgacgag ttctaagaaa    1140
acatcccaag aaaggaattg tgccacttca gaacatttaa atcgtaatgc tcggtgtcca    1200
ctgaggttaa acggagatga caaaaaataa tttgaacagt attaaaatta tttgaaccgg    1260
aagaatccct tgatgtatta ggcttacggt ggaactagta aattttccta atttgtagcg    1320
cttgtgtaac aattatctgc gttttgtttt cattttcaaa ttattcgaag cttcaattga    1380
agaagcatta cnggtcattg aagtagtgac atgaacacat gggatcacaa tatcgagagc    1440
tttccatttt aagtaatcct aacctacatg atcaatcacg                            1480
```

<210> SEQ ID NO 22
<211> LENGTH: 7561
<212> TYPE: DNA
<213> ORGANISM: Varroa destructor

<400> SEQUENCE: 22

```
aaccttgtta gacatatttt tgtggaaata tgttacttat agaatttact tttattccag      60
caacaatttg aaactaagaa acagccagaa aattaggtcg gttaggatac aagaataggc     120
cacacttaga agaatcaact taccgacttt actattaaaa ggatacgtaa ggtacgaaac     180
atgctaatgt ctaacttctt tttgccactt tagtttgaaa aagatcacgc taatccttga     240
cgcagcgctg tcgacgaact ccgtaacgac tactgaagcg tcgtgatgtg ccgcaccgcc     300
aataacatca acacgaactg cagcggagcg atgagtaccg cgctgttgac ggttgcccta     360
gtcattgcag tatgcgcggt aggtactttc ggaaagttag acgcggaatc accgcccagc     420
gcaccatctc cagttgagta ccctccccaa tacttcggta agtgcgtcct acatgtgata     480
actgtagagc ccattagaac aatttgcgta aattatcctg cgacatcgtc tcaagtacac     540
agtaagatga gtacataatt attactgcca cacgtaagta gttttagtta tatccgctct     600
taatcaacga tatagcatgg ctgttatagc aacgaaaagt aattaaatct atgccacata     660
ccagaaacgt tttctagctt gaaaaaaaat tatatgtcta agccttccta ccggctctat     720
tggattcgcc actttaaagc taatctacaa gctagatcag tgattgccga aaggaaagc     780 aaggatgact aagcttcaca attcttcaga tgtctgttga atattttgct tcattgctga     840
caaaaactta tgtactcgca acggaaacaa ttatatataa atagttctat ttaatagatg     900
acattagcct gtactggtcg tcgttttaca tatagcatt acaaactggc gacccaacga     960
atttatgctt atggaaggtt ttgccagtat ttatgcagtt gaccgcggaa tcaatcgaca    1020
attgacctaa catctacaga tgtactgtct tgatagtcct gagtcagatt ttctggttga    1080
tctgtataat aatctccgac aggtatagct cgtccttccg ctcagaatta ttctcataga    1140
catgaaatgg attttgccag aagtctcagt tcatgaagat cttgatagtt taaagtacgc    1200
aaatgcaacc gatgcttatc aagaaaaatt gccgatgtcg caaagatgat gaggaattac    1260
cgtatcggat attctaacca aaacctactg gagaatgatt ggacatcaag acatgcttgt    1320
ttaaattgcg gatgacagta gaagccatgg tacgatagta acgaatagac atttaagtcc    1380
actaggtcta tttatagcat ttcaagtaaa tatatctcac agggtcttaa attattattg    1440
atgaaaccct ttttctgagt ctttccgctt cgtgtttttc attattactt aaccaccgg    1500 caaattaata caaggaacga ggatcacaaa caaatctttg attaaatgat attgaaaatc    1560
atagatagcg gtaagcgaaa agctgataga ctacctgcat attacgcctt tcgtcttctt    1620
tcctgcttaa gatgcgcccc ttgaagcaga gtatgttctt ctcaaaaaag ctgacgtacc    1680
tccagcgcct tggaaccgct tgtacaatga ttggggtaaa aggtgagtcc ttgatcgatg    1740
tatcatggat ctaattaaac ccctaaggca cgttctttag tttcaaatgc cttcaatata    1800
ctgtgtagtg cagttcataa tgcataggca tttacaagac cactaaaaac gagacaggag    1860
aatcctacaa atgtcttcct cgattcactc tatttggttc actcgattag ggctgataac    1920
tggaagaatc taaatcacct gtggggcaaa cggtcagcta cacttccgac ccggtgggac    1980
aaacgccctc agccgcagtg gaacgagcta tccggttatt ggggaaagcg ttcggcccag    2040
taaatgtacc gcctgaatag aagtaaacag aaatgtactg cagaagaagg ctagctctcg    2100
ttctcaccgc tatccgtaag tgaaaaggac ttcgaagacc aggtgtcacc atggggcagt    2160 cgatttagc agtaaccgga ttcgtaaagg agccggctgg aaacgatgga agcatacaa     2220 aaacatacat ttttggagg cctaaggcct ctgatggcaa aaattgttta ccgcacacat     2280
aatcaataaa aaatactaaa ggatatatcc agattcgatg acaacatcat actggtcata    2340
```

```
atgtctaatg attatagtct agcaaaggaa tataactcaa ctttatcaaa agaacgtgac    2400
tatgaaccta ttgaacagga ataccattgc gaagacgcta atatcttagc gataaataat    2460
aaatataagc agcttatttt ctagattaca acatataacg tacgcataag tcattaaaat    2520
aatgaaacaa atatggaaag ctaatgtcg aaacgaatgg aaacatagta ggttgaaaca    2580
agcaatgaca gcaccaaaaa catcaagtac tatttaacaa tcaattatat catttacgta    2640
agaagataca aatagggacg gcacgggtat tgcaaaaggc aaaagggtgc ttctcaaagc    2700
tctccgatca agttagtcct cttttccagga ccggatcggc gctctgcacg aaggtgcagg    2760 ccgtttttcta atttctttgc cacgccgtgt tgattatcat tagcaagaac tgaacaaccg    2820
tcacagccat tagttaacta gaacatatac acaaatatca ccttcacatg agaagaccaa    2880
acgttatttt aaaacgtttg ttcaattcat agcacgatcg agcctatgca tgacgaaacc    2940
tcagggaaaa caaagttctc gtatcaacag atcggacaga cgaggtaatg gatagtgaca    3000
agtaagcgga taatcggtca tcgcctcttc gaatgcgacc gtaatctccg tgtgtattgg    3060
cttaactgat ctcaatcatt aagacaatct atgcaaaat ctcatgattg aagacgcgtt    3120
actgtatggt gacatgccgc attgcacgga gtactaattt tctaggtctc aagattttca    3180
gctcacttgt taattcacta ctatgagacc atatttttat ctacatattg ttgttttgta    3240
tcatacagat gtccaaattc aagacgttaa cgctcacgct ttatgtagat gaggaaatta    3300
gatttacact ataggcaaga gctaagtccg ctagcttacc tactgaaata tgaagcatgt    3360
ttatatagcg acgattctgg tatttttttt gcatgtagag ctacaaacga cagtgtctag    3420
gattcatgct gcaaaaataa acattttttg atagatctca attctcctaa gcttcgttgt    3480
taccacagat ggagtgacaa catccacgag gccctggcac tgcgatttat tcgactttt    3540 cgggacgtat gttccaaacg ttttcggttc gttaagtatt cactcgcgac acggccgtat    3600
accagctttc gtgctccaca ctctgctcgt aaagtaaata acactactct atcgcttata    3660
acaaaaacca ccccactga gccacggaaa tgctaattcg aagctggaaa gagagaacaa    3720
ctaacgatca ataacatgtg actgataaag cttcaaaata gtgcataagc tatatacgag    3780
atagtaacca ggcaggacgc aaatgatacc acaccgtaac cactctcata gagtcattgg    3840
aaacacggct cttattctac tgacggtatt ctaacttgcg acttgttcta cgctacttaa    3900
tgcaatgaac gaaattgtaa ttcattttt aattttaca tatatatttc tttttatcac    3960
aaatgaataa taaacacat ttttcaacaa taaataacaa ttctgaatta aggaaaaatg    4020
aaaataccaa taactaagga ctgctgcgcg aagataccc tatggtaagt tcacgtcttc    4080
gtctgacgag aacaaaagta attgctaatc ccacagatct tcactaagag acccttgatt    4140
ctcccttcca gcaatattgg acccgaacgc agcaactaat atcaatgaca gggcggacaa    4200
taatatcacc aaaagcaagg agagagtctc aatagggaag agacgaccca tagattgtca    4260
aatataacaa ctacgtactt tagagacacg gcgataacaa tgcaatgcca taatgttgta    4320
aaagtaaaca tgcaaatgaa gagaaaaaag acaagtaaaa atcagaacgt cgacacacaa    4380
acgaatgaca gacacatact gagttataaa tggaagctaa taaacaatca gattaaaagc    4440
aagaaaaaca agcggcacga gtgtgaaacc caaaagaatt ccgtaaagat atttgtttac    4500
ataacgaagc agtcaagcaa gaaatatagc agtcgatcaa tgacggggta cttgctatca    4560
agccaaaaat gttgttatta tatgaaatct atatatagta gataaaaacg tataacataa    4620
gcacacgatt attatgctaa cgtacttaag atatgataat gataataata tgtgttatac    4680
atatatatga tgataaaaag atagatataa tggtacgaga aagtatttgt agattattat    4740
```

```
tatcaaacaa aaagaaaggg tgtggtaaca tcgagggaac gaaaactgcg agccaaagca    4800
cgttgcaaga ttaaaggcac accttcgaac ctgctaaaga aaggaagtaa cggaaaaaat    4860
gaaaaaaaaa agaaacaggc cacaagaaag agaacagagt actgctgata aaattgctga    4920
tgtctttttg ttcggccaat ctccaagtac tttgaagaag tgcacgattt atgactccgt    4980
tgattaagaa gtgcactttt attgaaaaaa aagaccttag aaatatatgg aactaatcgt    5040
ttctactagg actataatat cccgcagctt ataataatat aatccagcta aaagctcatc    5100
ttaggtactg ggattaggaa aaacattatt ctacgtctga tggaaagtgt attgatactg    5160
gcactaatca agcgtaaatt cagaggggac tgatataaat gttccaacta ataatacctg    5220
ataatgattt aatattgacg caaaggtctg gtgtaaaaaa gttaccaaaa tgacgaatta    5280
attcgtttaa ttttgttttg tagtcaatat ctcagtcagt gcgatcggat tgcaccttac    5340
ttacttaaat cttatctacc tttgtttatc tgtcagtata ataacggaat ttattttttta   5400 tcagacaaaa attgcacaaa cgttaaaata ataattaatt atgccattct caaagaaatt    5460
accacaatca tcgctaaatg aatcgactaa tgctcattat atagccttgc aattcttcct    5520
tccatagatt ttaagaaagg cctttactaa cctatgtgtg tttatatatt attgcaacca    5580
aattatgctg cgtttgaaaa tacaaagcct atgcttgtgg tctttccttc ataagcaaca    5640
ctttgtctat actagggagc cttatattag tatgttttcc agaacgacag caaaatttac    5700
tccacgtttc gtttccttcg gccccttgga aaaactcaaa tgcaatagca taaaggcagg    5760
taaaattttg ctttgaacca ttatttgagg tcttaacaac aattttatc tagttggatg     5820 ctttgcagtg ataattctag gcgcactttc gcatcatcta tgtgtagacc aatgccaaaa    5880
atcaagcgcg tattactgac ttgaatctat tgtgattcgt ccaaaacgaa tccgtgcgtg    5940
tatcactcta ttaaacaaaa ctttgttact tctatgaatc aatttaactg tagaagcaga    6000
ttgtaaaatt gccagataaa actgtacgaa agtttttatc cattgaccag cgtttaacct    6060
tccagctccg catatttaac ctcttgaata gtactactta ttctcagtca tctatagcag    6120
acttagagct tacctgctga aaggggaatt gcggtgtcta agtcataaag ggcactggaa    6180
atcttctgaa gaaaatatac tatgtcatag tgaaatcttt attagctaaa tatttatttt    6240
ccataaatac tgcaggtaga caaacacata cccaaacgag gtcaacatta aaccttgtat    6300
tttgttttta caatcgcccc catacagagc gaacggcttc gccttttata caatctgact    6360
aatgatcaac acttattaca attctcagca agattcctcc tgctgctgta caaaaatttc    6420 taacgttttct tttgctaatg gtataataag atattcaaca ccatcatgac ctttctttat    6480
tcgaaccatg tcatggtcaa cgaattcagt cagctgcgta cggagcgtaa ggtcggagtt    6540
gacgacgaac gcctcacgac acattcgata gcagtcttga aaggccatac cacgaaagct    6600
gctggcggac gaattggctg atgaacaacg ttccaaagta tagttagcta taatcataaa    6660
tacctgcaaa aacatactta gagataaaaa aaaatggcca cgtacagtgc gcctctgtgt    6720
tggcgatcgc attgttatgt attaatcatc caagtatata atttaattaa cagtagtgcc    6780
agttgctgcc tgtcgcctca ttggtactgc ttatgaagct gcttgctgtc aaatcgata     6840 ggaacatcag taagttttga gttgtttgaa acgatagca catattaatt aaaatgaaaa     6900
tctagtgtat ggaaactata tagctatcac cttttcactt gcatgtacgt atagtaataa    6960
acggcaccac acatgcgcgg catctgcccc tgccatttac aaacgcctat tcttatgcat    7020
ctattcaacc gggccttgca cgcgataagt actgcacatt tgtccacact atcctgatat    7080
```

```
ttgtactacc tgacctaaag caagctcaac ttgttagtaa atctgtgaat cccaatcata    7140
ttataaggtt ttaacaattc tgttatttgg ttgctttcat tcataataac tctgtgacct    7200
gttacaggta tcatattgcc ttgtatcaat tatattctgc tctctgctcg ccctcttcgt    7260
ggtattctgc tttctttaat aaagctaacc ttcactttca aaattccata taaattttag    7320
gctgtttaaa aaccagtcaa ctaagcaatg tgataaaatt aagttttttc agaaattcct    7380
aatttatttt tctagaaaag gcttcgtgtt taacttcagg gcggagagtg aaaaaaatcg    7440
atttctttag atcaaatatg aactttgtat agaacataaa aaacggacga ttttaacatt    7500
aaaatgttta acaaatactc aaccattatt tagtaaactg aacgaataga taattttccc    7560
t                                                                    7561

<210> SEQ ID NO 23
<211> LENGTH: 1392
<212> TYPE: DNA
<213> ORGANISM: Varroa destructor

<400> SEQUENCE: 23
aacgttatgt tgacacttta tttattcatt cattagcatt actcgacact tatttactgg      60
gagatcaaat agagtgtctt catcgtcctt cacagattca gcctttcaat tcatcttcga     120
tcgaaatccg ggctgagttc ccaagaagtt ttctcaagat gccattattt ccttctgccg     180
gacagctgac cgatcatatt ggagatctca tcgagctgat ggagttgcat cgtcgccgaa     240
acgcaatctt ggaacacgcg attacggaag cattctgagg tgcaattgcg gctaatgaaa     300
tcccgcatgc cggggtacat atcggcgcac tccttacaga tgttgtgcat tcggtttagg     360
tagccgtaga agtgcggggc atatgggccc cgacaatctg catcgagaaa tagacgctta     420
tgcaggacca tggtgcccgt ggcgccagcg aaaccaccca gaggttcgaa tccggcaaga     480 cttttgcgttc gtacaccccg aagctgagag gatgcaacaa gcgccactag caaaggccat     540
gccgataatt tcttatacga gcgccccatc tgtaaaataa cgaatagatt atttccaccc     600
ttccatcaat agacatgttc ttttgaacgt gagcagatgg cacggtgaag tttaagaaac     660
cgttgagggt tgaagatgat tttttcagca gcgcgtgact gttgttttca ctgaatggca     720
ttgtagcaca gttgactcga tataaacagc gcatcagtca atagacacta gacgcaaccg     780
aatgtctact aatattgtaa tacctaaata atgaagcaga acgacatctt aatcagttta     840
tattaataac ataaacaatg gttaatattg tgccgtttca caatggcagc aaggccgcca     900
agtacaggaa acccctaaa tataaacaac gacccgtgag agagcaactc gcatgaatat     960
gcacactatg ctgaggatga cttctttctc gagcaaatgg gtctaacgat aaccgggctt    1020
atcacggtaa cccagctctt cgtatatctt caaagtgatt cattcaaact ttcacatagg    1080
tgaactagtc aggtccaaag cgaacagtca gatttaaaac atttacaaat aatctatgta    1140
agagctgtat atctcatcga ttcgtctttg tagctgacta tagacgtgac atttgccatg    1200
caccactggt aacatcactt gccttaacac agtccacact ttgatatggc actaaatatc    1260
gagctagcga aagtgtagcc tcggtctctt ctctgattcg acttcatagc cgggcttata    1320
tatgcgaata catgatacgg tcagtcaatt ttagtcccgg tttggctata attgagaccc    1380
gggtcaatca tg                                                         1392

<210> SEQ ID NO 24
<211> LENGTH: 6553
<212> TYPE: DNA
<213> ORGANISM: Varroa destructor
```

<400> SEQUENCE: 24

```
tatatatata tatatatata tatatatata tatatatata tatatatata tatatatata      60
tatatatata tagggcttt cgtgtataat gattgacata ctaatttgat gcaagagcaa     120
ctctgacccg cccaacagcc ttagttcatc ataggcttga tatgcagccg attatgtctt     180
agaacgtagt agattagaag gggcacactt gatttcggga accatatgat gccataatat     240
tgttgaacgg ccacttaata tagctgtccg tcttcatgta tgctgatatt tgcggaagtg     300
cctcgaaccg ggtgataaaa tctgttagat tcgtcacatt tttgaatact gatgaattcc     360
agacatacat ttgaaaaaga agttcgtaag caagaaagtc aacgtaagtt aacttttcat     420
ttaggaacca tttcctttcg ccgagaaatg ccgaaatctc ttgaagcata tgtgcaaagc     480
gatcgataaa tccgccattg agaactccaa ggcagtccgc ctttgagcat gtaccctcct     540
gaagtcgctc gaaacttgga ctgtaacaca atttcatgaa ggctgtgcgt aagtcagcaa     600
tctgttgttc aacgagctca cagtgagcta gctcaatctc ggttgtgcca attagattaa     660
acttacgtcc caagtatctc ataatagcat gactctgact tagtttgaca ctgccatcga     720
ctagatacgg taagttggga aacgcaagat ttaacttgtt atttgccttc tctagggccc     780
attctgattt atcgaaatca gaagcggcaa tagtagtgta acgccgttct tcaaaatcag     840
cgccagcgta agctagcaac aaacggattg gctgggccag acctcgaatg tcccaatagc     900
ccagcagaat cttagatttc gatgacgaca taatgcgaaa ttttatttcg cgatatggct     960
tctaacttgt tctccgaacg aataacagct tgatctaaca ccaaaattat tccgctcaca    1020
aaaatagatt tttcttgttt ttttttaaat gtgactgtat aaacaacaga tgcaaaacaa    1080
cgatgatgat cgtcagcaga agacacagcg gccgaacaag cgccaaaaaa gagggggcctc    1140
cgcgcatgcg tcacggaaca aatttttaccg aacgttacga tctgattacg agcgaaggaa    1200
cgatgcggaa catacgaagt atctataaag gtagcgacaa atctaaatct aaagagtgat    1260
gttaccaaat ttaccgggat cgtccgtata tttaaaaata tatattgttc tccgtcacct    1320
tatcattatt atgccctcca gcatcgccat ttcatatatt gcactaaata tttatacaat    1380
aattgaattt ttaagaaagt tagccaaccc gttattgcca cgtttagtcg ctgcattcta    1440
caaaatgaca tgaaaagtta cgtaaaatgc ttttccccga tgcttgaacc ccatatagcc    1500
ggcctttaac gtaacgtagt gaaaccgggt taatgcggag cgggcatgtt gtgtatattt    1560
agataaagct cacagacgtg attggcttgc cctatatgta gcattaaacc gtaaataagt    1620
aaacgaccaa tatcgatata ttggggctgt agaaagggca ctggccgttt ttccagctag    1680
atggcgtgca agtcacatac cttgaatcgt gtcatcgctt catttacaaa tagaaattca    1740
gcagtagaac tgttcgagga catttgttca gacttaggat aaaatgactt gaaaatgaat    1800
ggaattttat tatactttac aattttacta cgatcaaggt gcatatgttg cccaggctca    1860
tacaaaatat gttctgttta tggtcaagat acgttatcgg agagatggct caaaaatggc    1920
ttcatcgtca atggaacgat ctggaacaat cgttatgaaa gatgctcccc gcaacgatcg    1980
aacaattact taattaatta attaattaga acaattaatt aatgtatagg aaattattgc    2040
agaagctaag tataggaact agatgaaaca gtttcaaatc atcaggaaaa atgttgcaac    2100
aagaagtttg atgatgttaa ttaaagtaat ttactgtatc gtatctgcga aactctacaa    2160
aaatgcaacg aaatccagcc ttcgattaca gccgatgaaa aatagatcac atacacatgt    2220
cccgtaaaat ctgtggcgaa gctcatactg acactggggt tcggtgggaa ttgaaaggca    2280
```

```
tcgtgcatta tagactgctg ccgtctggaa aaatgattca ttcatgcctc tattgtcaaa      2340
ccactggcaa gattgctaca agccaccttc cactataaaa gtgccagacc acagaaacag      2400
ttagctagtc agcttggatc gagaacttta acatttgctg ttaaactatt ctctgcttcg      2460
atatctgcaa acatcccgta gtggtgttca tttagtttca atagaagtat gcgaaatgat      2520
tttttgtccg aaaacctcaa aaggtatcca gtgatgaaat tcacgtaaca ctataaaatt      2580
ggcagaaggt cattcatcaa aatagcgcgt attagtttac cgatattgtt tgaaaatata      2640
gaagtatttg cttcaaattt tatttataaa cggctaatgg ttctctggga atccgataag      2700
ggcaagctgt tttgtggacg tcgcttatta tttgccactt gtattggtgt tctcaatcct      2760
gtcgcacatg cccttatacg aatgatccac taaagggatg cttcatataa ataggcactt      2820
tgccctcata caattcagtc gaggtatcgc aggcctaaac taatgtttag cttttaaatt      2880
taacgatgct agcctgccgt gaaactgtta ttcgctatac atagaattct cgttgagttt      2940
tcaaattatc ctaaaatgct ttatgttgat ataatggcat aatttatagta aatggctttg      3000 acggcactat cgcttcaccc attcgtcata cttatatgcc ttttccaaag caaggtagcg      3060
gatgtcaatt caaaatgtac agtaaagctt ctctcattat agcctaaagc gctataaacc      3120
taatggttta ttgcataaac aggacattgt acataacagt ggctcgtacg cttcgaaatag     3180 tcctttaacg gagacagtca tataggggg aggggagac gcgattacgt gagccaaaat       3240
ttattaaaca ctacgaaagg ataagataag tgctttgcca aggattcctc tatctcgttg      3300
caaaacggga accaataaat ggttagtcat tcctatcaaa ttgctctttg agcaactttc      3360
tatatccttc atttttacat tgacaacgtt caagtggttc ctgttgtcag gcgtcattaa      3420
caacgagcgc gtcattgtgt ttacagcggt gacgtgcaca aaatgtaaat aacggatgag      3480
gcacactctg taggactaat ctacgaccta aatgggcctt attctcacta gggtgtctgg      3540
aaagatttag attgttggcc ctccaagtag tggtatcctt gcaaacctgt ctttggcaaa      3600
taccagcacg gaccagccta gaatatgttt cacgccgtat atttctaatt ttctgcggtt      3660
ctaaccttta aagtactgta gcgctctata acagattttc tggatataaa ataatcacat      3720
agacgtacta taaactaaag ggaacttaaa aagatgcggg tggccagacg cagcgagatc      3780
gagtcaacgt caagtctagg ataacagaat tgtgctttta gttatatcca attgagcctg      3840
cctatcatag tcacgcacta gacatctgct gcgtacacgc ccgtaagacc taccatggtt      3900
ctgcctgcgg aacaagagct actaatgaaa cggatataaa tacaaattga cttagatgac      3960
atcagtcgct atgacatgta tccaagctgg cattaatcag tgagtgaaac attcgaggta      4020
gaccatcttg attactattt actattcagt cgcttttttcc cacaaagatg acagtcctat      4080
aacatgtttc gcaagcgtgt ggagcgttcg agattgcatg gatgaggtta ggttcgattg      4140
gcaatgaatt ttgacgatag agtgatgagt agcttttaca aagaggagaa aaggatttta      4200
acagtcagca ataatggat tgtggattcc tacagttccc ttgcagtgta tcaagcgttt       4260
gcttgagaca ctttcataca tagagtttca tgtaagtgcc agattagaat agcattaata      4320
attcagcatg catgattcct tcataaactc aaatagacga caaactgtct gttcttgcta      4380
gattcaaacc aatgataagg ttcagccatg caatataaag agccgtacca gccggatgca      4440
gctgttatta tctgtccatg gatgatgaag ttgattttgg cagtaagcct attatgttac      4500
tgtttattgg aattactttt gctgatagca tagtaacaag caaactaatc atgtagttcc      4560
tatgtagcaa tactttttct ggtccatctt gctttagtgt gctgtaactg tggtggtatc      4620
ctccgaaact tgggacatgc atgattccat ggcagatcaa gcgtctcctt tatcttagaa      4680
```

```
ccgctaggca atagcctatg gtttgttagc tctcaatcag taattttat gtacacacaa    4740 acgcattatg agtaaatgat ctgcggacac ggtataaaac acaagttcga atagacaccg    4800
tctggatctg ttacaatatt aatataagac aagcattgtt tatgttttat atgtacttat    4860
tattgaatta tttatgtttg ggagaaatag atgaatagaa gaaaaagca tgtgccatgt     4920 tattcgtatt gcgtagaaaa ctgtcctcat tctcacatat gtaaaacctt cttttccagt    4980 taaaatttt ggtctgccta gttgttttat tgtttactgt ttatggatta gcccaccta     5040 tataacctag tactgttgtt gatcccactg aaggattaat ttagcaattt aagagaaaag    5100
gcgaaagcac gtatgtatta tagaaaagga aaacaggttt taaaagtttg ttgtttgctt    5160
aagaagaatc gactgttata gttcttgatc taattcagca tatgagttcg acatcaaca    5220 cgacacgaag tgttttttgc tttctgctct ctacatatgt atactattta tttttttaca    5280
tttgaaaagc cattggatct gacagatgtt tcatactaat tcatagctgc gttttattaa    5340
gtcatgcagc ttcaatgctc aaagactaac ttgtggattc cggctactag aagatctcgc    5400
taaagatgga caacttttaa cgtttcgaac aaacaggtta cggatgcgtt ttgtgaggta    5460
caattagttc gtttgtgtta gtaagtagtc tttttcgaac atatgtcccc ccttcattt     5520 gtgttttcgc ggtgcaacgg cacggccgcg aagcctattt cacttctatg tatggtaacc    5580
cttctggctg ctcttcttt tactgtaagt tcctccagca agttcagaaa ctcttctaac      5640
cactggcaaa gcaccccac ctaccccga ggtactagtc aatgttttat tctctgatct      5700
tagaaaagcg tacagctggc ggcaaccaag taagtacgca aacagtgcag cgagagcaac    5760
ccgaacggat atccctgcgc atagatattt atgttaggtg gtactgcgat aaaggcaaga    5820
ggatgaagtt gaagcaagca aaagtagatt ggtaggaatt tagagaggtg aatttaacct    5880
ggtcggtccg aatccttcga tatgcttttc gctctggtta ccttgctgtt atagaggact    5940
attgcgcgcg agacagacgc acgcctgctt gttcacttga ctacgctgtg cgttggcaaa    6000
ggctgtttca gtcaaagcac gtcggatgat tggagtacct ctctgcgctc tttggctttc    6060
cgactgtaca cagtgttagc gtcgcatgct tgtagctcta acaaagcgtc tgcgttctgc    6120
cacaaggtga taaccattca ttagaagtag cttccctctt ccaaacaaca ggcacgcacg    6180
cgcacactta accgaccgat cgaccggcca actcatgccc tctttttcag tcgctttacg    6240
cctcacttct ttttcagta gcgttctcct catctgtgtt accttcagca tgtcgctaat    6300
cggacgtcgg catatacta cgtagatgac ggtcgtagtc gtggtcatat tcggcttcat    6360
gggtatcctg ctgctcttgc tcgcgctcag tgttcgtcgt tgccgctgtt tatctaccgg    6420
gaacacgagg acctgcaagt cgggggagct ggcacagcct tcaagctaag cttcaggaga    6480
tactagaaaa agcaacaccg ttcactgcag cggcaaacac cgaagaacag aaagatgcac    6540
actgtatagg gac                                                       6553
```

<210> SEQ ID NO 25
<211> LENGTH: 22
<212> TYPE: DNA
<213> ORGANISM: Artificial sequence
<220> FEATURE:
<223> OTHER INFORMATION: Synthetic primer
<400> SEQUENCE: 25
aagtactcta gcaattgtga gc                                             22

<210> SEQ ID NO 26

<211> LENGTH: 22
<212> TYPE: DNA
<213> ORGANISM: Artificial sequence
<220> FEATURE:
<223> OTHER INFORMATION: Synthetic primer

<400> SEQUENCE: 26
ctcttcgcta ttacgccagc tg                                          22

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
ctcgggaagc gcgccattgt                                             20

<210> SEQ ID NO 28
<211> LENGTH: 20
<212> TYPE: DNA
<213> ORGANISM: Artificial sequence
<220> FEATURE:
<223> OTHER INFORMATION: Synthetic primer

<400> SEQUENCE: 28
accagaagcg gtgccggaaa                                             20

<210> SEQ ID NO 29
<211> LENGTH: 19
<212> TYPE: DNA
<213> ORGANISM: Artificial sequence
<220> FEATURE:
<223> OTHER INFORMATION: Synthetic primer

<400> SEQUENCE: 29
ccacagcggt ggttcggat                                              19

<210> SEQ ID NO 30
<211> LENGTH: 37
<212> TYPE: DNA
<213> ORGANISM: Artificial sequence
<220> FEATURE:
<223> OTHER INFORMATION: Synthetic primer

<400> SEQUENCE: 30
tggatccacc ggttcgaacc cactagccga aatggac                          37

<210> SEQ ID NO 31
<211> LENGTH: 32
<212> TYPE: DNA
<213> ORGANISM: Artificial sequence
<220> FEATURE:
<223> OTHER INFORMATION: Synthetic primer

<400> SEQUENCE: 31
tcctttcgtg acctccaccc ttaatagaaa cg                               32

<210> SEQ ID NO 32
<211> LENGTH: 31
<212> TYPE: DNA
<213> ORGANISM: Artificial sequence
<220> FEATURE:
<223> OTHER INFORMATION: Synthetic primer

<400> SEQUENCE: 32
ggaggtcacg aaaggagcat tttgtgcttg g          31

<210> SEQ ID NO 33
<211> LENGTH: 31
<212> TYPE: DNA
<213> ORGANISM: Artificial sequence
<220> FEATURE:
<223> OTHER INFORMATION: Synthetic primer

<400> SEQUENCE: 33
gcaactaatt ctcgacaaag agacgcagtg c          31

<210> SEQ ID NO 34
<211> LENGTH: 35
<212> TYPE: DNA
<213> ORGANISM: Artificial sequence
<220> FEATURE:
<223> OTHER INFORMATION: Synthetic primer

<400> SEQUENCE: 34
ttgtcgagaa ttagttgctc gccacgatat cattg       35

<210> SEQ ID NO 35
<211> LENGTH: 37
<212> TYPE: DNA
<213> ORGANISM: Artificial sequence
<220> FEATURE:
<223> OTHER INFORMATION: Synthetic primer

<400> SEQUENCE: 35
cgtcacgtgg ctagctggca agaggacttc ccataag     37

<210> SEQ ID NO 36
<211> LENGTH: 27
<212> TYPE: DNA
<213> ORGANISM: Artificial sequence
<220> FEATURE:
<223> OTHER INFORMATION: Synthetic primer

<400> SEQUENCE: 36
atagatctga acccactagc cgaaatg               27

<210> SEQ ID NO 37
<211> LENGTH: 31
<212> TYPE: DNA
<213> ORGANISM: Artificial sequence
<220> FEATURE:
<223> OTHER INFORMATION: Synthetic primer

<400> SEQUENCE: 37
atagatcttg acctccaccc ttaatagaaa c          31

<210> SEQ ID NO 38
<211> LENGTH: 28
<212> TYPE: DNA
<213> ORGANISM: Artificial sequence
<220> FEATURE:
<223> OTHER INFORMATION: Synthetic primer

<400> SEQUENCE: 38
atagatctcg aaaggagcat tttgtgct              28

<210> SEQ ID NO 39
<211> LENGTH: 28
<212> TYPE: DNA

```
<213> ORGANISM: Artificial sequence
<220> FEATURE:
<223> OTHER INFORMATION: Synthetic primer

<400> SEQUENCE: 39
atagatctct cgacaaagag acgcagtg                                     28

<210> SEQ ID NO 40
<211> LENGTH: 28
<212> TYPE: DNA
<213> ORGANISM: Artificial sequence
<220> FEATURE:
<223> OTHER INFORMATION: Synthetic primer

<400> SEQUENCE: 40
atagatctaa ttagttgctc gccacgat                                     28

<210> SEQ ID NO 41
<211> LENGTH: 28
<212> TYPE: DNA
<213> ORGANISM: Artificial sequence
<220> FEATURE:
<223> OTHER INFORMATION: Synthetic primer

<400> SEQUENCE: 41
atagatcttg gcaagaggac ttcccata                                     28

<210> SEQ ID NO 42
<211> LENGTH: 20
<212> TYPE: DNA
<213> ORGANISM: Artificial sequence
<220> FEATURE:
<223> OTHER INFORMATION: Synthetic primer

<400> SEQUENCE: 42
ggacgacttc ccacacttct                                              20

<210> SEQ ID NO 43
<211> LENGTH: 20
<212> TYPE: DNA
<213> ORGANISM: Artificial sequence
<220> FEATURE:
<223> OTHER INFORMATION: Synthetic primer

<400> SEQUENCE: 43
tgccaccctt catcttcatt                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
tccttacttg tgcgcaatct                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic primer

<400> SEQUENCE: 45
ccggtagtcc atagcgaagt                                              20
```

```
<210> SEQ ID NO 46
<211> LENGTH: 20
<212> TYPE: DNA
<213> ORGANISM: Artificial sequence
<220> FEATURE:
<223> OTHER INFORMATION: Synthetic primer

<400> SEQUENCE: 46
aattagttgc tcgccacgat                                           20

<210> SEQ ID NO 47
<211> LENGTH: 20
<212> TYPE: DNA
<213> ORGANISM: Artificial sequence
<220> FEATURE:
<223> OTHER INFORMATION: Synthetic primer

<400> SEQUENCE: 47
gaaaatagcc ctttggcaag                                           20

<210> SEQ ID NO 48
<211> LENGTH: 19
<212> TYPE: DNA
<213> ORGANISM: Artificial sequence
<220> FEATURE:
<223> OTHER INFORMATION: Synthetic primer

<400> SEQUENCE: 48
catcaccatt ggtaacgag                                            19

<210> SEQ ID NO 49
<211> LENGTH: 19
<212> TYPE: DNA
<213> ORGANISM: Artificial sequence
<220> FEATURE:
<223> OTHER INFORMATION: Synthetic primer

<400> SEQUENCE: 49
cgatccagac ggaatactt                                            19
```